United States Patent
Houchen et al.

(10) Patent No.: US 9,663,585 B2
(45) Date of Patent: May 30, 2017

(54) ANTI-DCLK1 MONOCLONAL ANTIBODIES AND METHODS OF PRODUCTION AND USE THEREOF

(71) Applicant: The Board of Regents of the University of Oklahoma, Norman, OK (US)

(72) Inventors: Courtney Houchen, Edmond, OK (US); Sripathi M. Sureban, Oklahoma City, OK (US); Randal May, Oklahoma City, OK (US); Dongfeng Qu, Edmond, OK (US); Nathaniel Weygant, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 84 days.

(21) Appl. No.: 14/073,169

(22) Filed: Nov. 6, 2013

(65) Prior Publication Data
US 2014/0056972 A1 Feb. 27, 2014

Related U.S. Application Data

(63) Continuation-in-part of application No. 13/027,845, filed on Feb. 15, 2011, now Pat. No. 8,936,941, which is a continuation-in-part of application No. 12/454,355, filed on May 15, 2009, now Pat. No. 8,198,255.

(60) Provisional application No. 61/128,063, filed on May 16, 2008.

(51) Int. Cl.
| | |
|---|---|
| *A61K 6/00* | (2006.01) |
| *A61K 39/00* | (2006.01) |
| *A61K 39/395* | (2006.01) |
| *A61K 45/00* | (2006.01) |
| *A61K 45/06* | (2006.01) |
| *A61K 47/00* | (2006.01) |
| *A61K 47/48* | (2006.01) |
| *C07K 16/40* | (2006.01) |
| *A61K 9/127* | (2006.01) |
| *A61K 31/7088* | (2006.01) |
| *C12N 5/095* | (2010.01) |
| *C12N 15/113* | (2010.01) |
| *C07K 16/30* | (2006.01) |

(52) U.S. Cl.
CPC .............. *C07K 16/40* (2013.01); *A61K 9/127* (2013.01); *A61K 31/7088* (2013.01); *A61K 39/39558* (2013.01); *A61K 45/06* (2013.01); *A61K 47/48646* (2013.01); *C07K 16/30* (2013.01); *C12N 5/0695* (2013.01); *C12N 15/113* (2013.01); *A61K 2039/505* (2013.01); *C07K 2317/73* (2013.01); *C07K 2317/76* (2013.01); *C12N 2310/14* (2013.01); *C12N 2503/02* (2013.01); *C12N 2510/00* (2013.01); *G01N 2333/91215* (2013.01)

(58) Field of Classification Search
None
See application file for complete search history.

(56) References Cited

U.S. PATENT DOCUMENTS

| | | | |
|---|---|---|---|
| 7,345,027 B2 | 3/2008 | Tolentino et al. | |
| 7,511,025 B2 | 3/2009 | Wyatt et al. | |
| 7,511,132 B2 | 3/2009 | Khvorova et al. | |
| 2005/0255487 A1 | 11/2005 | Khvorova et al. | |

FOREIGN PATENT DOCUMENTS

| | | | |
|---|---|---|---|
| WO | WO 03/018816 A1 * | 3/2003 | |
| WO | WO 2004-048938 * | 6/2004 | |
| WO | WO 2007/086738 | 8/2007 | |

OTHER PUBLICATIONS

DCLK1 gene-genecards/dclk1 protein/dclk1 antibody, 12 pages, 2015.*
Harris, Marion. The Lancet, Oncology 5: 292-302, May 2004.*
May, et al., "DCAMKL-1 and LGR5 Mark Quiescent and Cycling Intestinal Stem Cells Respectively", Stem Cell, pp. 1-38 (2009).
Sureban et al., "Knockdown of RNA Binding Portein Musashi-1 Leads to Tumor Regression In Vivo", Gastroenterology 134:1448-1458, (2008).
Elbashir et al., "Analysis of Gene Function in Somatic Mammalian Cells Using Small Interfering RNAs", Methods, vol. 26:199-213 (2002).
Battelli et al., "The RNA-binding Protein Musashi-1 Regulates Neural Development Through the Transplant Repression of p21 $^{WAF-1}$", Mol. Cell. Neurosci., vol. 31:85-96 (2006).
Xi et al., "Differentially Regulated Micro-RNAs and Actively Translated Messenger RNA Transcripts by Tumor Suppressor p53 in Colon Cancer", Clin Cancer Research, vol. 12:2014-2024 (2006).
Smart et al., "Two Isoforms of the Cold-inducible mRNA-binding Protein RBM3 Localize to Dendrites and Promote Translation", J. Neurochem., vol. 101:1367-1379 (2007).
May et al., "Identification of a Novel Putative Pancreatic Stem/Progenitor Cell Marker DCAMKL-1 in Normal MousePancreas", Am. J. Physiol. Gastrointest Liver Physiol., vol. 299:G303-G310 (2010).
Mwangi et al., "DCAMKL-1: a New Horizon for Pancreatic Progenitor Identification", Am. J. Physiol. Gastrointest. Liver Physiol., vol. 299:G301-302 (2010).
Mukherji et al., "A Phosphoproteomic Analysis of the ErbB2 Receptor Tyrosine Kinase Signaling Pathways", Biochemistry, vol. 45:15529-15540 (2006).

(Continued)

*Primary Examiner* — Alana Harris Dent
(74) *Attorney, Agent, or Firm* — Dunlap Codding, P.C.

(57) ABSTRACT

Monoclonal antibodies against DCLK1 and conjugates containing these monoclonal antibodies are disclosed. Methods of producing and using these monoclonal antibodies are also disclosed.

14 Claims, 40 Drawing Sheets
(30 of 40 Drawing Sheet(s) Filed in Color)

(56) References Cited

OTHER PUBLICATIONS

Ratti et al., "A Role for the ELAV RNA-binding Proteins in Neural Stem Cells: Stabilization of *Msi1* mRNA", Journal of Cell Science, vol. 119:1442-1452 (2006).

Gerbe et al., "DCAMKL-1 Expression Identifies Tuft Cells Rather Than Stem Cells in the Adult Mouse Intestinal Epithelium" Gastroenterology 137:2179-2184 (2009).

* cited by examiner

Figure 10
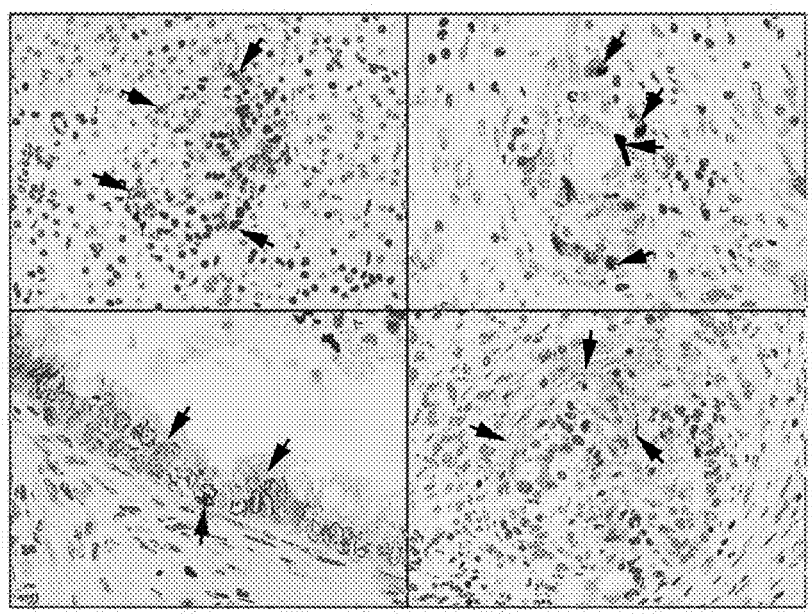
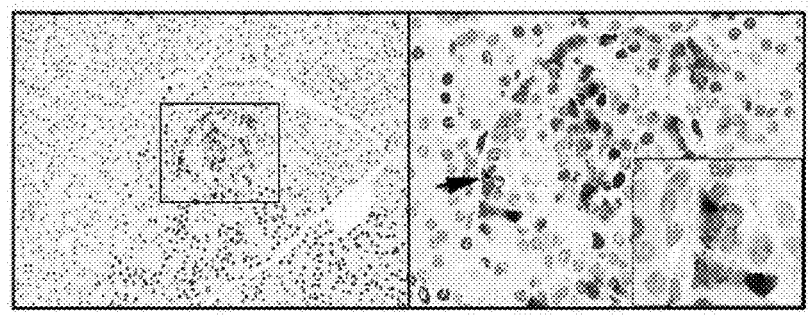
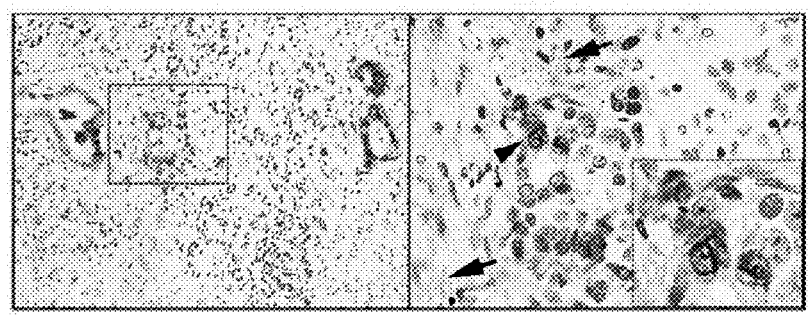
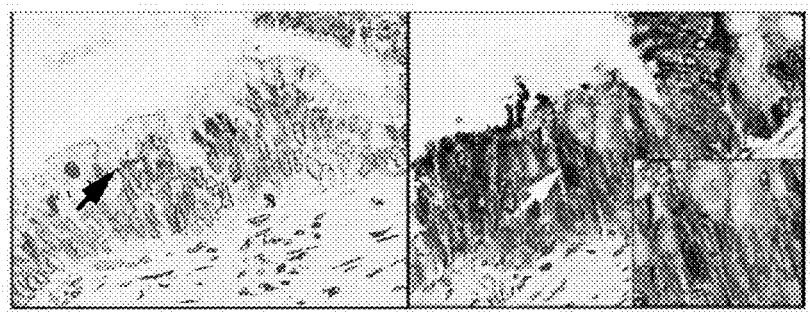

Figure 26
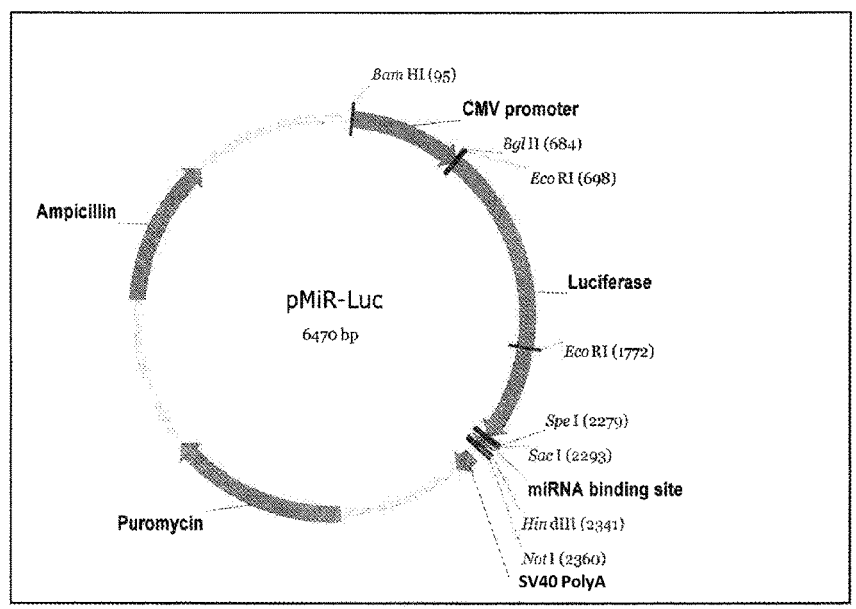
5' ---AGAAAAATCAGAGAGATCCTCATAA--AGGCCAAGAAGGGCGGAAAGTCCAAATTGCTCGAG
              Luciferase Gene
TGATGAAAGCTGCGCACTAGT-- AACTATACAACCTACTACCTCA--AAGCTTAATAAAGGAT
              (SpeI)     let7a Binding Site     (HindIII)
CTTTTATTTT CATTGGATCT GTGTGTTGGT TTTTTGTATG CGGCCGCTA--- 3'
                                                (NotI)
Signosis Figure 27
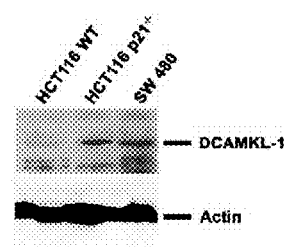
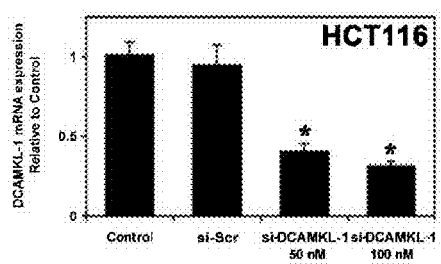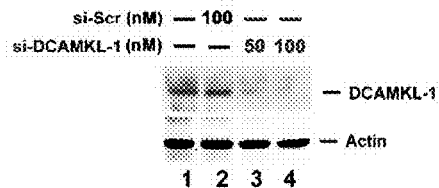
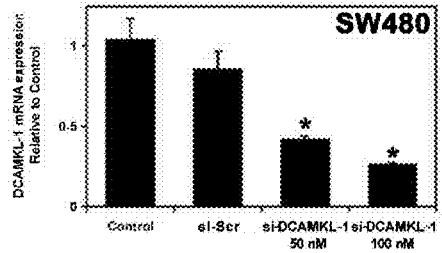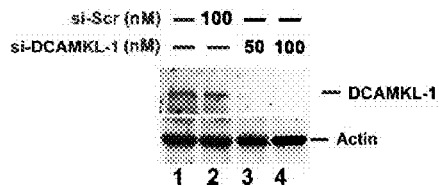

Figure 28
A
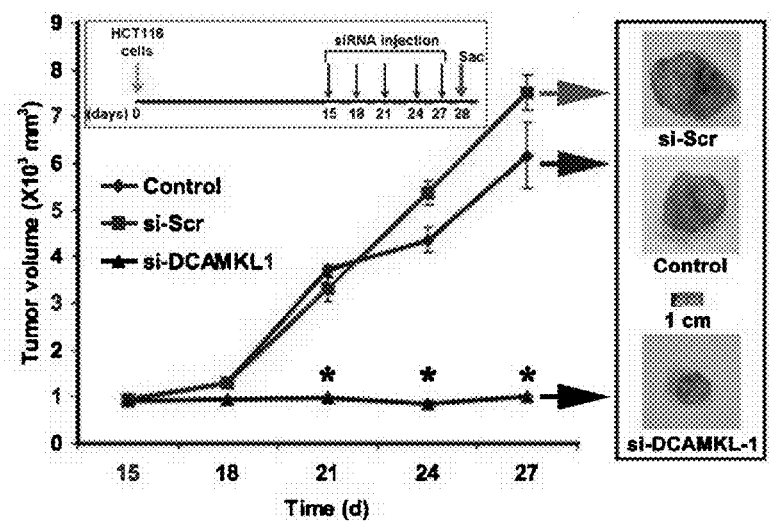
B
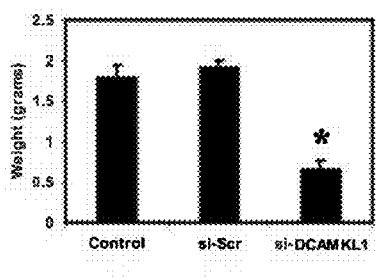
C
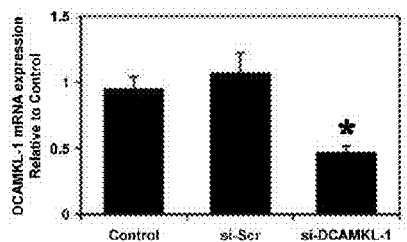
D
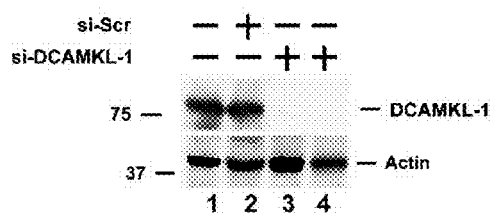

Figure 29
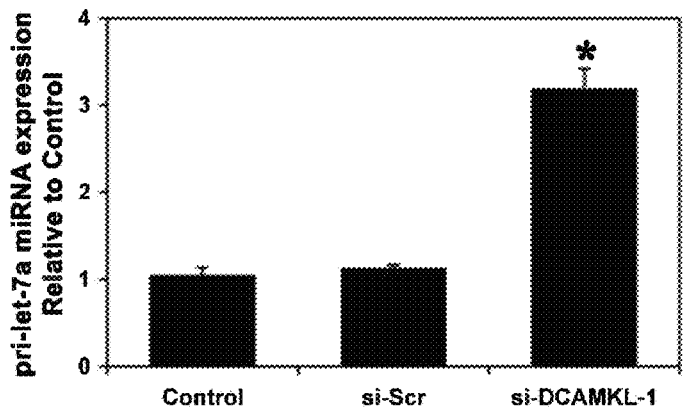
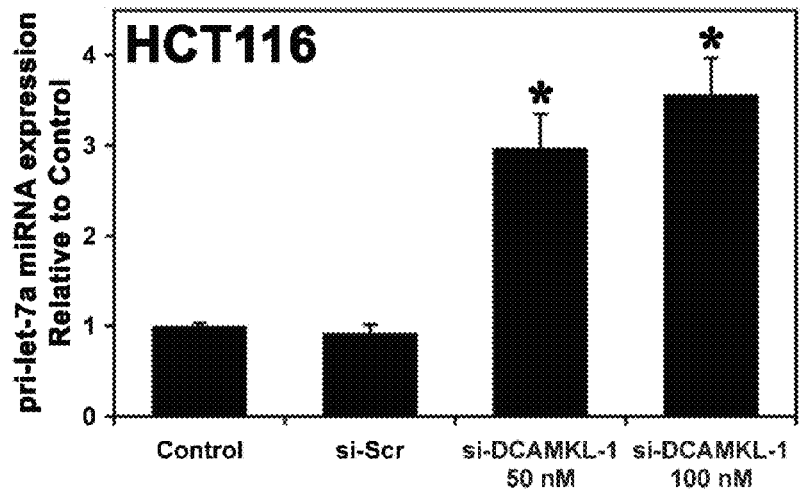
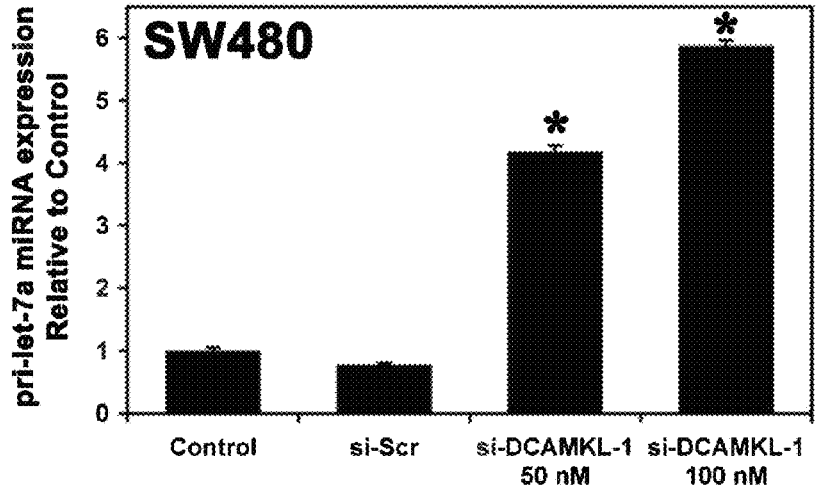

Figure 31
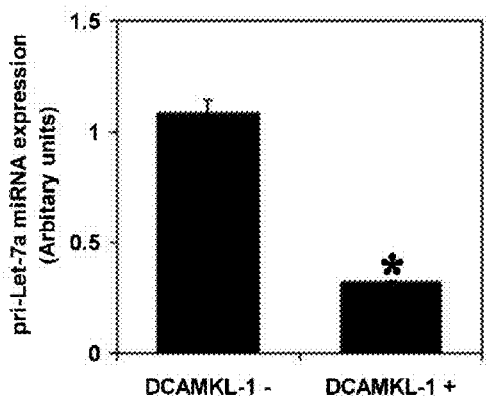
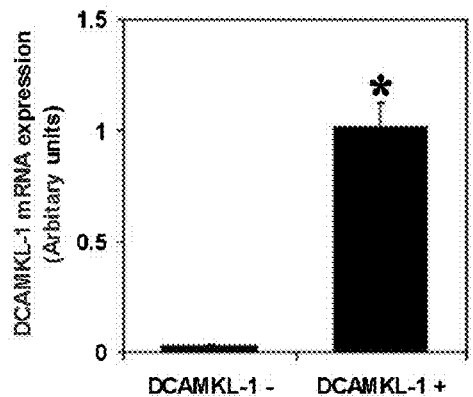
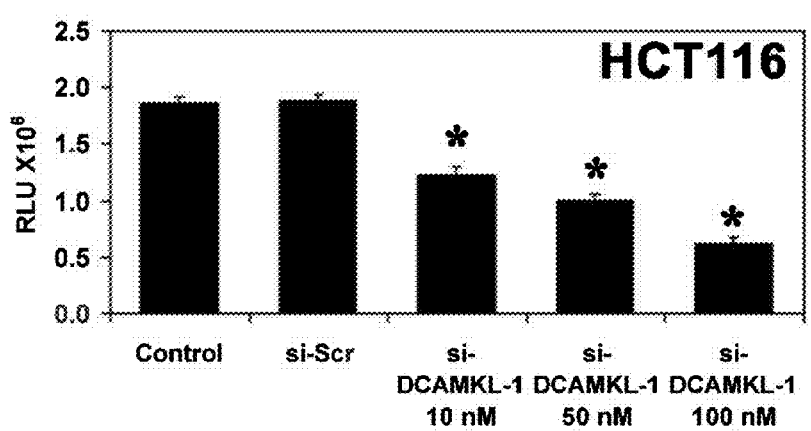
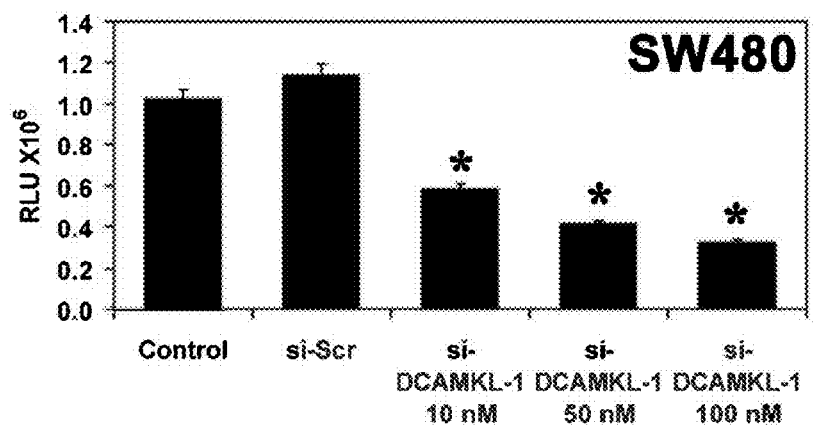

Figure 33
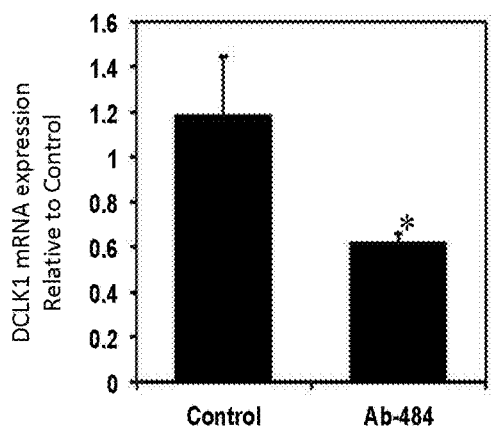
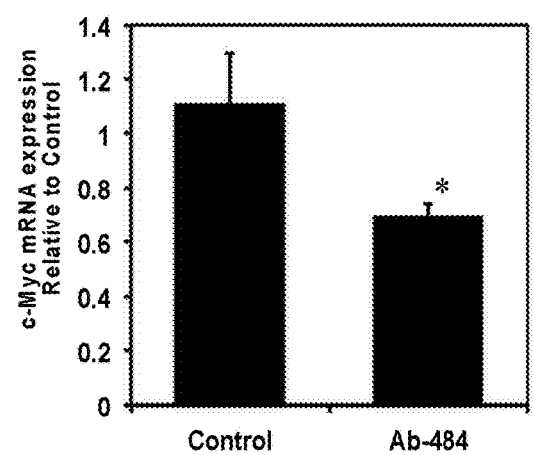
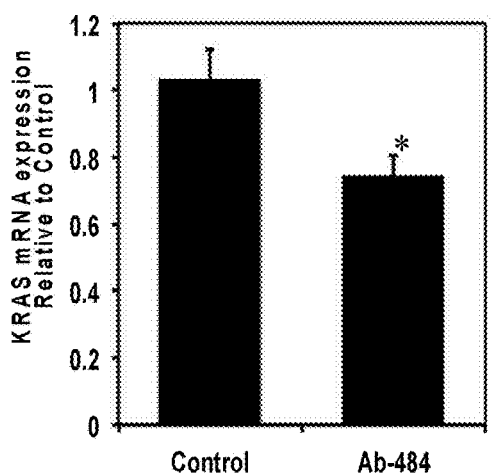
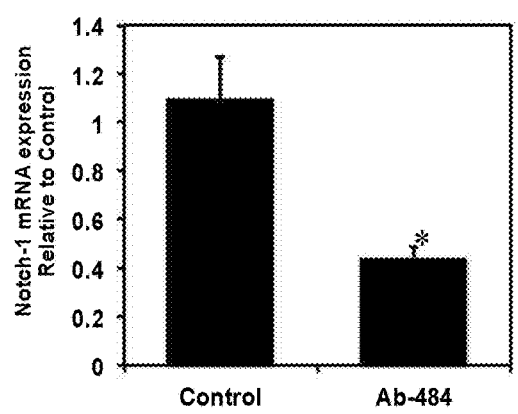

ANTI-DCLK1 MONOCLONAL ANTIBODIES AND METHODS OF PRODUCTION AND USE THEREOF

CROSS REFERENCE TO RELATED APPLICATIONS/INCORPORATION BY REFERENCE STATEMENT

This application is a continuation-in-part of U.S. Ser. No. 13/027,845, filed Feb. 15, 2011; which is a continuation-in-part of U.S. Ser. No. 12/454,355, filed May 15, 2009, now U.S. Pat. No. 8,198,255, issued Jun. 12, 2012; which claims benefit under 35 U.S.C. 119(e) of provisional application U.S. Ser. No. 61/128,063, filed May 16, 2008. The entire contents of the each of the above-referenced patents and patent applications are hereby expressly incorporated herein by reference.

STATEMENT REGARDING FEDERALLY SPONSORED RESEARCH OR DEVELOPMENT

Not Applicable.

BACKGROUND

Cancer of the colon is the second most frequently diagnosed malignancy in the United States, as well as the third leading cause of cancer death. Colon cancer is a highly treatable and often curable disease when localized to the bowel. Surgery is the primary treatment and results in cure in approximately 50% of patients. However, recurrence and metastases following surgery is a major problem and often is the ultimate cause of death.

Due to its proximity, cancer of the colon often metastasizes to the small intestine. The prognosis of the cancer spreading to the small intestine is related to the degree of penetration of the tumor through the bowel wall and the presence or absence of nodal involvement. These two characteristics form the basis for all staging systems developed for colon cancer. Various characteristics also assist in prognosticating colon cancer and its spread to the small intestines. For example, bowel obstruction and bowel perforation are indicators of poor prognosis. Elevated pretreatment serum levels of carcinoembryonic antigen (CEA) and of carbohydrate antigen 19-9 (CA 19-9) also have a negative prognostic significance. However, an age greater than 70 years at presentation is not a contraindication to standard therapies; acceptable morbidity and mortality, as well as long-term survival, are achieved in this patient population.

Cancer cells can also originate in the small intestine. However, this is a much rarer type of cancer. Symptoms of cancer of the small intestine typically include pain or cramps in the middle of the abdomen, weight loss without dieting, a lump in the abdomen, or blood in the stool.

Cancer of the stomach, also referred to as gastric cancer, also frequently metastasizes to the small intestine due to its proximity. This cancer is often difficult to diagnose in early stages and can be in the stomach for a long time, growing to a large size before symptoms arise. In the early stages of cancer of the stomach, an individual may experience indigestion and stomach discomfort, a bloated feeling after eating, mild nausea, loss of appetite or heartburn. In more advanced stages of stomach cancer, there may be blood in the stool, vomiting, weight loss or more severe pain.

Because of the frequency of these types of cancer (approximately 160,000 new cases of colon and rectal cancer per year alone), the identification of high-risk groups, the demonstrated slow growth of primary lesions, and the better survival of early-stage lesions, screening for gastrointestinal cancers should be a part of routine care for all adults starting at age 50, especially those with first-degree relatives with colorectal cancer.

Procedures used for detecting, diagnosing, monitoring, treating and preventing cancer of the colon, small intestine and/or stomach are of critical importance to the outcome of the patient. Patients diagnosed with early stage cancer generally have a much greater five-year survival rate as compared to the survival rate for patients diagnosed with distant metastasized cancers. New diagnostic methods which are more sensitive and specific for detecting early cancer of the stomach, small intestine and colon are clearly needed.

Patients with gastrointestinal cancers are closely monitored following initial therapy and during adjuvant therapy to determine response to therapy and to detect persistent or recurrent disease of metastasis. There is clearly a need for a cancer marker which is more sensitive and specific in detecting recurrence of these types of cancer.

Defining the mechanisms that regulate stem cell fate is critical in increasing our understanding of the neoplastic process. Tumorigenesis in the gut arises specifically in the stem cell (Clarke, 2005; de Lau, 2007; and He, 2007) population located at or near the base of the intestinal and colonic crypts, while transit cell populations originating from the stem cell zone become fully differentiated and are eventually sloughed into the lumen. The short life span of transit cells, whether they are mutated or not, limits their deleterious influence in the intestinal or colonic crypt (Potten, 2003; and Booth, 2002). Because no specific gut stem cell markers have been identified definitively (Bjerknes, 2005; and Kayahara, 2003), recognizing and assaying resident intestinal stem cells is quite difficult and has raised contentious argument; however, the microcolony assay following γ-irradiation is by definition a functional evaluation of intestinal stem cell fate (Withers, 1970) and can provide a mechanism for examining the early events of tumorigenesis. Because homeostatic mechanisms of stem cell proliferation are the same processes that become dysregulated in carcinogenesis (Sancho, 2003), a complete examination of these proliferation mechanisms holds medical significance in targeting future cancer treatments; therefore, a more detailed understanding of the pathways that regulate stem cell behavior is essential.

Recently, Msi-1 (Musashi-1) has been identified as a putative stem cell marker (Potten et al., 2003). Musashi-1 was identified as an RNA binding protein that is a translational repressor of p21. Musashi-1 regulates asymmetric division in neural precursor cells, and is expressed in intestinal crypts in the stem cell zone. Its increased expression has also been observed in tumors in APC/Min mice. However, it has not been shown to be a reliable intestinal stem cell marker.

Pancreatic adenocarcinoma has the worst prognosis of any major malignancy with a 3% 5-year survival (Hoyer et al., 2006). Major obstacles in treating pancreatic cancer include extensive local tumor invasion and early metastasis. Recently, it has been proposed that pancreatic tumors arise specifically in the stem cell population located in these tissues. There is increasing evidence that a small subset of cells termed cancer stem cells (CSCs) or cancer initiating cells (CICs) are capable of initiating and sustaining tumor growth in transplantation assays (Diehn and Clarke, 2006). CSCs share unique properties with normal adult stem cells, including the ability to self-renew and differentiate. CSCs are often refractory to current standard chemotherapeutic agents and radiation therapies, as they are designed to eradicate actively cycling cells, not slowly cycling cancer stem cells. Thus novel therapies that specifically target the cancer stem cell population, either alone or in conjunction with current strategies, may be more effective in obliterating solid tumors.

The existence of CSCs was first demonstrated in acute myelogenous leukemia (Bonnet, 1997) and subsequently verified in breast (Al-Hajj et al., 2003), pancreatic (Li et al., 2007) and brain tumors (Singh et al., 2004a; Singh et al., 2003; Singh et al., 2004b). The CD133+ subpopulations from brain tumors could initiate clonally derived neurospheres in vitro showing self-renewal, differentiation, and proliferative characteristics similar to normal brain stem cells (Singh et al., 2004a; Singh et al., 2003; Singh et al., 2004b). Furthermore, transplantation of CD133+, but not CD133−, cells into NOD/SCID mice was sufficient to induce tumor growth in vivo. In a recent study, primary human pancreatic adenocarcinomas were implanted in immuno-compromised mice to assess the ability of specific cell surface markers to identify a subpopulation of pancreatic cancer cells with enhanced tumorigenic potential (Li et al., 2007). A subpopulation of CD44+CD24+ESA+ cells was identified as putative pancreatic cancer stem cells.

Tumor cell heterogeneity present in most solid tumors creates an enormous challenge for cancer eradication. Current strategies for inducing cell death generally target only the most rapidly proliferating cells within a tumor. Indeed, radiation therapy targets proliferating cells, which are the most sensitive to ionizing radiation (Cohn et al., 1997; Houchen et al., 2000; Riehl et al., 2000; Tessner et al., 1998); however, it is clear that effective tumor-eradication strategies must address the potential survival mechanisms unique to each particular cell type within the malignant population (i.e., quiescent stem cells). Currently, most traditional cancer therapies are based on their ability to kill most of the tumor population (i.e., log kill assays), but these treatments often fail to destroy cancer stem cells, which have been shown in several tumor types to be more resistant to standard chemotherapeutic agents (Li et al., 2007). This may explain why standard chemotherapy is effective in causing tumor shrinkage but often fails to prevent tumor recurrence, possibly due to the surviving cancer stem cell's ability to regenerate the tumor even after chemotherapeutic insult. This is not an unreasonable inference when one considers the gastrointestinal tract, where a single surviving intestinal stem cell is able to reconstitute an entire gastrointestinal crypt following severe genotoxic or cytotoxic injury (Bach et al., 2000).

Characterization of stem cells from the hematopoietic system, neural stem cells from the central nervous system and neural crest stem cells have emphasized the importance of specific cell surface antigens that permit the isolation of stem cells by fluorescence activated cell sorting (FACS). A candidate pancreatic stem cell, which is characterized by its expression of the neural stem-cell marker nestin and lack of established islet- and duct-cell markers, has been described in published reports (Abraham et al., 2004; Lechner et al., 2002; Zulewski et al., 2001). Furthermore, the basic helix-loop-helix transcription factor neurogenin 3 (NGN3) controls endocrine cell fate specification in uncommitted pancreatic progenitor cells. In the pancreas, NGN3-positive cells co-express neither insulin nor glucagon, demonstrating that NGN3 marks early precursors of pancreatic endocrine cells. Moreover, NGN3-deficient mice do not develop any islet cells and are diabetic. These data taken together demonstrate that NGN-3 and nestin are critical components of the pancreatic stem/progenitor cell compartment. A convincing recent study demonstrates that the adult mouse pancreas contains islet cell progenitors and that expansion of the β cell mass following injury induced by ligation of the pancreatic duct results in NGN3 gene expression and the ensuing differentiation of endogenous progenitor cells in a cell-autonomous, fusion-independent manner (Xu et al., 2008). These data demonstrate that functional islet progenitor cells can be induced in pancreatic ducts following injury.

Therefore, there is a need in the art for new and improved methods for detecting, diagnosing, monitoring, staging, prognosticating, imaging and treating gastrointestinal and pancreatic cancers. The presently disclosed and claimed inventive concept(s) overcomes the disadvantages and defects of the prior art by providing such methods via a newly identified gastrointestinal and pancreatic stem cell marker.

BRIEF DESCRIPTIONS OF THE DRAWINGS

This patent or application file contains at least one drawing executed in color. Copies of this patent or patent application publication with color drawing(s) will be provided by the Office upon request and payment of the necessary fee.

FIG. 1 illustrates the expression pattern of DCLK1 in normal mouse small intestine. (A) Immunohistochemical staining of normal small intestine for DCLK1, arrow indicates the cell positive for DCLK1 in the stem cell zone. (B) Pre-incubation with blocking peptide completely abolishes DCLK1 immunoreactivity. (C) Immunohistochemical staining of normal small intestine for DCLK1, brown color indicates the cells positive for DCLK1 (indicated by the arrows).

FIG. 2 illustrates co-localization of Musashi-1 and DCLK1 in mouse intestine. (A) Immunohistochemical staining of normal small intestine for DCLK1 (brown color indicated by the arrow). (B) Immunohistochemical staining of normal small intestine for Musashi-1, brown color indicates the cells positive for Musashi-1 at the base of the crypts. (C) The cell positive for DCLK1 stained red (indicated by the arrow) appears at the base of the crypt. (D) Intestinal section stained for Musashi-1 green. (E) Co-localization of DCLK1 and Musashi-1 (yellow indicated by the arrow). The magnified inset image represents the single cell positive for both DCLK1 and Musashi-1. (F) Co-staining of DCMAKL-1 (red color indicated by the arrow) with nuclear Hoechst 33342 (blue) staining. (G) Co-staining of Musashi-1 (green) with nuclear Hoechst 33342 (blue) staining. (H) Colocalization of DCLK1 and Musashi-1 (yellow indicated by the arrow), co-stained with nuclear Hoechst 33342 (blue) staining. The magnified inset image represents the single cell positive for both DCLK1 and Musashi-1 (yellow color).

FIG. 3 illustrates the fate of DCLK1 positive cell following ionizing radiation (IR). (A) 6 hours after whole body 6 Gy IR, morphologically appearing apoptotic cells were observed in the lower third of the intestinal crypt, but apoptosis is not observed in any of the DCAMKL-1 positive cells indicated by the arrow. (B) The small intestine stained for DCLK1 (red) and TUNEL (green) to demonstrate apoptosis in the crypts 6 hours following radiation. (C) Small intestine of unirradiated mice demonstrating no staining for phospho-H2AX. The crypt area is magnified in the inset. (D) 6 hours post IR; small intestine demonstrates DNA damage by positive phospho-H2AX staining (DAB brown). The crypt area is magnified in the inset. (E) 6 h post IR; small intestine demonstrates DNA damage in the DCLK1 positive cell indicated by the arrow. The magnified inset image represents the single cell positive for both DCLK1 and phospho-H2AX. (F) After 24 hours after IR, the appearance of multiple DCLK1 immunoreactive mitotic figures indicated by 'M' was noted adjacent to morphologically appearing apoptotic cells indicated by arrows that were also expressing DCLK1.

FIG. 4 illustrates DCLK1 expression in the regenerative crypts post IR. (A) 84 hours following IR, no DCLK1 expression could be detected in regenerative crypts. (B) Staining at 144 hours after IR demonstrates restoration of DCLK1 expression in the intestinal crypt indicated by arrows.

FIG. 5 illustrates the histological evaluation of small intestine of APC/min mice. (A) Scattered single cells were immunoreactive for DCLK1 in the intestinal crypts (arrow) and a trend towards increased expression on villi (arrow head). (B) DCLK1 staining within adenomas of APC/min mice indicated by the arrows. DCLK1 was also immunoreactive in the cells within the villus epithelium surrounding the adenoma (arrow head). (C) APC/min intestinal adenoma immunostained with anti-PCNA (red) and co-stained with DCLK1 (brown). The cells immunoreactive for DCLK1 are indicated by the arrows. (D) Portion of (A) magnified to demonstrate the cell positive for DCLK1 is not immunoreactive for PCNA. (E) Double staining of PCNA and DCLK1 in putative stem cell zone of wild-type mouse demonstrates the quiescent state of the DCLK1 expression cell indicated by the arrow.

FIG. 6 illustrates β-Catenin expression in the small intestine of APC/min mice localized with DCLK1. (A) Normal appearing APC/min mice intestine immunostained for membrane β-Catenin (brown) and cytoplasmic DCLK1 (red) co-immunostaining indicated by arrow. (B) Magnified image of (A) demonstrating the cell positive for DCLK1 and β-Catenin indicated by arrow. (C) DCLK1 expressing cell (arrow) along with other cells demonstrating nuclear translocation of β-Catenin within an APC/min adenoma indicated by the arrow, just adjacent to normal membrane β-Catenin staining epithelium. (D) Magnified image of (C) demonstrating the DCLK1 positive cell indicated by the arrow.

FIG. 7 illustrates the colonic distribution of DCLK1 and structure of cell positive for DCLK1. (A) The cell positive for DCLK1 appears at the midpoint of the colonic crypt in the proximal colon. (B) In distal colon, the distribution of DCLK1 expression appears at the base of the colonic crypt. (C) The close views of DCLK1 expressing cells within the colon and distal jejunum (D) demonstrates the axonal-like process.

FIG. 8 illustrates pancreatic DCLK1 expression and specific islet cell type differentiation in adult mice. (A-C) DCLK1 expression (brown) in the main pancreatic duct (A—arrows) and in the periphery of pancreatic islets (B—arrows). No DCLK1 expression was observed in acinar cells or accessory ducts (C). (D-F) Immunofluorescence demonstrating DCLK1 (red) and somatostatin (green) staining of pancreatic islets. Co-localization is demonstrated with arrows in the merged image. (G-I) DCLK1 (red) and glucagon (green) immunofluorescence staining of pancreatic islets. No colocalization is observed in the merged image. (J-L) Immunofluorescence demonstrating DCLK1 (red) and insulin (green) staining of pancreatic islets. No co-localization is observed in the merged image. In the immunofluorescence staining: Nuclei were stained blue with Hoechst in the merged images.

FIG. 9 illustrates DCLK1 (referred to as "DCAMKL-1" therein) and other putative pancreatic stem cell markers. (A-B) The pancreatic tissue of newborn mice shows distinct DCLK1 staining (A—arrows) and NGN3 (B—arrows). (C-E) Immunofluorescence staining for DCLK1 (red) and NGN3 (green) are indicated with arrows in the pancreas of newborn mice. Merged image reveals distinct co-localization of DCLK1 and NGN3. Representative cells are indicated by arrows and nuclei are stained blue with Hoechst dye. (F-H) Adult mouse pancreatic tissue serial sections stained with DCLK1 (F—arrows), NGN3 (G—arrows) and nestin (H—arrows). (I-K) Immunoperoxidase staining for DCLK1 (purple) and nestin (brown) in pancreatic islet of an adult mouse (I). Magnified images of FIG. 9I show distinctly separate staining for DCLK1 (red arrow) and nestin (black arrow) (J), and co-localization of DCLK1 and nestin (K), as indicated by the arrow.

FIG. 10 illustrates DCLK1 and 14-3-3 σ expression in human pancreatic adenocarcinoma. (A) DCLK1 expression (brown) in histologically normal appearing tissue from pancreatic cancer resection specimen (top left). Spindle-shaped cytoplasmic staining of DCLK1 in neoplastic pancreatic islet tissue (top right). DCLK1 expression in ductal epithelial cells of pancreatic adenocarcinoma (bottom left). Intervening stromal elements demonstrate fibrillar DCLK1 immunoreactivity (bottom right). Representative cells are indicated by arrows. (B) Staining for 14-3-3 σ (purple) and DCLK1 (brown) at the islet periphery in normal appearing pancreatic tissue (left). In a magnified portion of the left image, a representative cell demonstrating the cytoplasmic expression of 14-3-3 σ is indicated with arrow (right). (C) 14-3-3 σ (purple) and DCLK1 (brown) expression in pancreatic adenocarcinoma (left). In a magnified portion of the left image, nuclear localized 14-3-3 σ (purple) in individual cells co-localized with cytoplasmic DCLK1 (brown) indicated by arrowhead (right). Fibrillar DCLK1 staining in the intervening stroma is indicated by arrows. (D) Left image demonstrates DCLK1 (brown) expression in ductal epithelium of a PanIN type lesion, a representative cell is indicated by arrow. Image on the right demonstrates intense cytoplasmic and nuclear staining of 14-3-3 σ (purple) and cytoplasmic DCLK1 (brown) in a PanIN lesion. Representative cell demonstrating nuclear 14-3-3 σ co-localized with DCLK1 is indicated by arrow. Insets in the images on the right in the panel B, C and D are magnified images.

FIG. 11 illustrates DCLK1 (referred to as "DCAMKL-1" therein) and vimentin expression in human pancreatic adenocarcinoma. (A) Arrow indicates a single slender DCLK1 expressing cell in a PanIN type lesion. (B) A single elongated vimentin expressing cell in the ductal epithelium of a PanIN type lesion as indicated by arrow. (C-D) Immunofluorescence staining for DCLK1 (red; C) and vimentin (green; D) in a PanIN lesion. (E-F) Merged images reveal distinct co-localization of DCLK1 and vimentin as indicated by arrows with nuclei stained blue with Hoechst dye. (G-H) Immunofluorescence staining for DCLK1 (red) and vimentin (green) in stromal compartment of pancreatic adenocarcinoma. (I-J) Merged images demonstrate immunolocalization of DCLK1 and vimentin with nuclei stained blue with Hoechst dye.

FIG. 12 illustrates DCLK1 expression in Pdx48$^{Cre}$-activated KRAS$^{G12D}$ pancreatic cancer mouse model. Pancreatic tissues from 5-month-old WT littermate (A) and from 5-month-old (B) Pdx48$^{Cre}$ activated KRAS$^{G12D}$ mouse were immunostained for DCLK1. (C) A magnified portion of the image (B) demonstrating cells positive for DCLK1 in the pancreatic duct. (D) A magnified portion of the image (B)

demonstrating cells positive for DCLK1 in the islets. Brown colored cells (arrows) indicate cells positive for DCLK1. These data demonstrate an increased expression of DCLK1 correlated with progressive neoplastic changes.

FIG. 13 illustrates FACS-based isolation of DCLK1 cells from mouse pancreas. FACS-based isolation of cells from mouse pancreas using anti-DCLK1 antibody. FACS plot of sorted cells. (A) side scatter oval gate R1. (B) Polygon gate R2 represents sorted fluorescent cells from gate R1 (0.36% of total cells). (C) Single cells following FACS with brightfield overlay.

FIG. 14 illustrates that DCLK1 sorted cells demonstrate growth in vitro and in vivo. (A) FACS isolated DCLK1 cells in suspension culture at day 1 (left) and demonstrating spheroid formation at day 21 (right). (B) Athymic nude mice 4 weeks after subcutaneous injection with either MATRIGEL® alone (left) or spheroid with MATRIGEL®, arrow indicates nodular growth (right). (C) Image demonstrates a tan grey soft tissue outgrowth with blood vessel formation under the skin of the DCLK1 spheroid-injected mouse as indicated by the arrows. (D) Image on the left demonstrates soft tissue from DCLK1 spheroid injection stained with H&E for histological evaluation. Cells which appeared to be epithelial in nature formed early islet-like structures, as indicated by arrows. Image on the right demonstrates groups of cells, which lined up around central spaces and appeared to be poorly formed glands (arrow). (E) Cells around the central spaces were positive for cytokeratin-14, indicating glandular epithelial origin (top left—arrow) and PDX-1, a marker of early pancreatic development (top right—arrow). Islet formations expressed the endocrine markers somatostatin (bottom left—arrow) and secretin (bottom right—arrow).

FIG. 15 illustrates a schematic representation of cell surface expression of DCLK1 (referred to as "DCAMKL-1" therein). The C-terminus of DCLK1 is predicted to be outside the cell surface and thus allows for recognition with antibody directed to this domain, which facilitates the isolation of DCLK1 cells by FACS.

FIG. 16 illustrates the expression of DCLK1 (referred to as "DCAMKL-1" therein) in the mouse small intestine. (A): Brown indicates DCLK1+ cells (arrows). (B): Quantitative representation of DCLK1 expressing cells as measured by cell position in intestinal crypts. (C): Co-immunofluorescence staining for DCLK1 (red—arrow, left panel) and ChrA (green—arrow head, middle panel) in crypts. No co-localization was observed in the merged image (right panel). (D): DCLK1 (red—arrow, left panel) and pPTEN (green—arrow head, middle panel) in crypts. No co-localization was observed in the merged image (right panel). (E): DCLK1 (red—arrow, left panel) and pAKT (green—arrow head, middle panel) in crypts. No co-localization was observed in the merged image (right panel). (F): DCLK1 (red—arrow, left panel) and somatostatin (green—arrow head, middle panel) in crypts. No co-localization was observed in the merged image (right panel). (G): DCLK1 (red—arrow, left panel) and secretin (green—arrow head, middle panel) on villus. No co-localization was observed in the merged image (right panel). * Nuclei in all merged images are stained blue with Hoechst 33342 DNA dye.

FIG. 17 illustrates LGR5 and DCLK1 in the mouse small intestine. (A): Brown indicates LGR5+ cells (arrowheads). (B): Brown indicates DCLK1+ cell (arrow). (C and D): Co-immunostaining for LGR5 (purple—arrowhead) and DCLK1 (brown—arrow). No co-localization of LGR5 and DCLK1 was observed in the putative stem cell zone (C) or CBC cells (D). Black box in (C) demonstrates a cell negative for both LGR5 and DCLK1. (E-H): Co-immunofluorescence staining for LGR5 (green) (E) and DCLK1 (red—arrow) (F). No co-localization of LGR5 and DCLK1 was observed in merged images (G) and (H). * Nuclei in merged image (H) are stained blue with Hoechst 33342 DNA dye.

FIG. 18 illustrates that LGR5 and DCLK1 mark proliferative and non-proliferative cells respectively in the mouse small intestine. Co-immunofluorescence staining for PCNA (green) (A) and LGR5 (red—arrowheads) (B). PCNA+ LGR5+ cells are indicated with arrowheads in the merged image (C). PCNA (green) (D) and DCLK1 (red—arrow) (E). A PCNA-DCLK1+ cell is indicated by the arrow in the merged image (F). * Nuclei in all merged images (C and F) are stained blue with Hoechst 33342 DNA dye.

FIG. 19 illustrates that DCLK1 identifies the quiescent anchored stem cell. Following mLRA, mouse intestines (distal jejunum) were immunostained for BrdUrd (brown) at day 7 (A) magnified in (B) and at day 10 (C) magnified in (D). (E-F): Mouse intestines 10 days post 8 Gy IR were co-immunostained for DCLK1 (brown) and BrdUrd (purple) or PCNA (purple). (E): Arrow indicates a BrdUrd+ (label retaining) and DCLK1+ cell. (F): Arrow indicates a PCNA- (quiescent) and DCLK1+ cell.

FIG. 20 illustrates the isolation of intestinal stem cells using DCLK1 (referred to as "DCAMKL-1" therein) based FACS. (A): Schematic diagram depicting the predicted cell surface expression and extracellular C-terminal domain of DCLK1. (B): Western blot analyses demonstrating cell surface expression of DCLK1 following biotinylation (Pierce Cell Surface Protein Isolation Kit, Pierce Biotechnology Inc., Rockford, Ill.). Biotinylated cell surface protein extract from intact cells (see FIG. 21) demonstrated the presence of DCLK1 (Lane B), but not in the unbound non-biotinylated intracellular protein extract fraction (Lane N). As a positive control, EGFR a known cell surface expressing protein was detected only in the bound fraction. (C): A representative ALEXA FLUOR® 568 (Life Technologies Corp., Grand Island, N.Y.) conjugated DCLK1+ cell following FACS (red); nucleus is stained blue with Hoechst 33342 DNA dye post-sorting. (D): A single DCLK1 sorted cell in suspension culture at day 0. (E): A spheroid containing 50-100 cells at day 21. Isotransplantation assays: (F): MATRIGEL® alone injected control mouse, (G): spheroid injected mouse demonstrating nodular growth on the flank (arrow), H&E staining of excised nodules from (H) control mouse and (I) spheroid injected mouse (arrow indicates glandular formation). Spheroid injected nodule stained for (J): cytokeratin-14, (K): Msi-1, (l): Math1 and (M): L-FABP, with representative cells indicated by arrows.

FIG. 21 illustrates confocal imaging of biotinylated extracellular membrane proteins in SW480 cells. Biotinylation of intact SW480 cells (used to isolate cell surface proteins) as demonstrated by incubation with streptavidin conjugated Cy3 (red) (A) and co-localized with the transmembrane protein E-cadherin (FITC—green) (B). Merged images with Hoechst DNA stain (blue) demonstrate that biotinylation is restricted to the extracellular membrane surface (C). Control cells without biotinylation reagent do not show staining for streptavidin conjugated Cy3 (red) (D), but do exhibit staining for E-cadherin (green) and Hoechst (blue) (E and F).

FIG. 22 illustrates FACS-based isolation of DCLK1 cells from the mouse intestine. (A): FACS plot of side scatter (chosen based on previous sorting experiments) of cells stained with ALEXA FLUOR® 568 (Life Technologies Corp., Grand Island, N.Y.) conjugated DCLK1 antibody. Gate R1 indicates localization of the DCLK1+ fluorescing cell population. (B): These cells were further gated through R2 based on fluorescence intensity. (C): FACS plot of side scatter of unstained control cells. (D): No cells were detected within gate R2.

Figure 25:
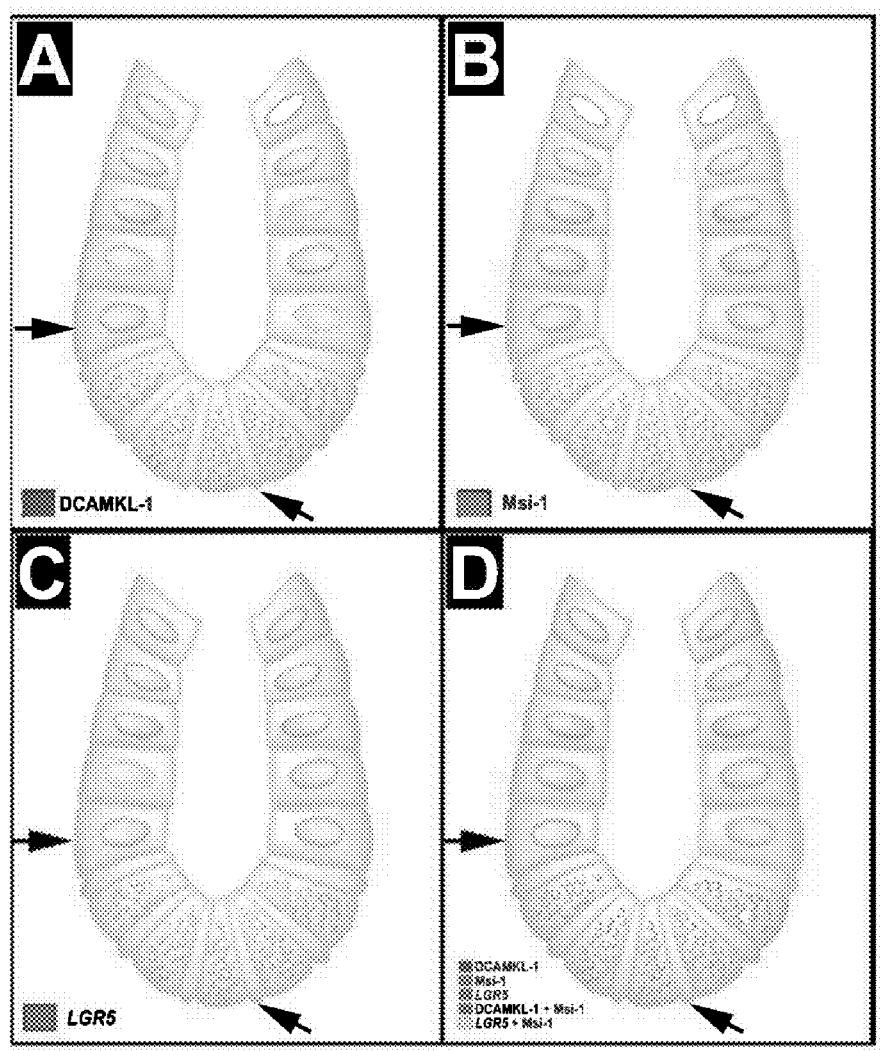

FIG. 25 provides a schematic illustration of the location of putative stem and progenitor cell markers in the mouse small intestine. (A): DCLK1 (red, referred to as "DCAMKL-1" therein), (B): Msi-1 (green), and (C): LGR5 (blue). (D): Merged image represents areas of predicted co-localization. Arrows indicate the position of DCLK1 expressing cells.

FIG. 26 graphically illustrates a map of pLet7a-Luc Reporter Vector (LR-0037) (Signosis, Inc., Santa Clara, Calif.) demonstrating the presence of the let7a binding site at the UTR of Luciferase gene. The nucleotide sequence depicted has been assigned SEQ ID NO:22.

FIG. 27 illustrates that DCLK1 (referred to as "DCAMKL-1" therein) is overexpressed in colorectal cancer. (A) Immunohistochemistry for DCLK1 (brown) in normal (left panel) and two different colon cancer tissues (middle and right panels). Black arrow indicates representative epithelial cells positive for DCLK1. Blue arrow head indicates the presence of DCLK1 in the stromal compartment. (B) Western blot demonstrating the expression of DCLK1 in three different colon cancer cell lines. Actin serves as control. (C) DCLK1 specific siRNA (si-DCLK1) decreases DCLK1 mRNA (left panel) and protein expression (right panel) in HCT116 colon cancer cells compared to controls. (D) Similar decrease in DCLK1 mRNA (left panel) and protein (right panel) observed following si-DCLK1 transfection in SW480 colon cancer cells. For C and D, values in the bar graphs are given as average±SEM and * denote statistically significant differences (*p<0.01) compared to control. All the experiments were performed in triplicates and were repeated 3 times.

FIG. 28 illustrates that DCLK1 (referred to as "DCAMKL-1" therein) is essential for tumor growth. (A) HCT116 cells were injected into the flanks of athymic nude mice (n=5 per group) to generate tumors. At day 15 siRNAs (si-DCLK1 and si-Scr) were injected directly into the tumors and followed by injections every third day (inset). After 5 injections, tumors were excised at day 28 and are represented above. Tumor sizes with standard error are shown from data collected at the time of every injection. (B) si-DCLK1 treatment resulted in significantly decreased tumor weight when compared to controls. (C) The expression of DCLK1 mRNA in the tumors quantitated by real-time RT-PCR. (D) Western blot analysis for DCLK1 was performed on tumors samples as indicated. For A-C, values are given as average±SEM and * denote statistically significant differences (*p<0.01) compared to control.

FIG. 29 illustrates that knockdown of DCLK1 (referred to as "DCAMKL-1" therein) induces pri-let-7a miRNA. (A) Quantitative real-time RT-PCR analysis for pri-let-7a miRNA in tumor xenografts. siRNA mediated knockdown of DCLK1 results in increased expression of pri-let-7a miRNA. (B) si-DCLK1 treated HCT116 cells demonstrate increased expression of pri-let-7a miRNA. (C) Similar induction of pri-let-7a miRNA was observed in SW480 cells. For A-C, values are given as average±SEM and * denote statistically significant differences (*p<0.01) compared to control.

Figure 30:
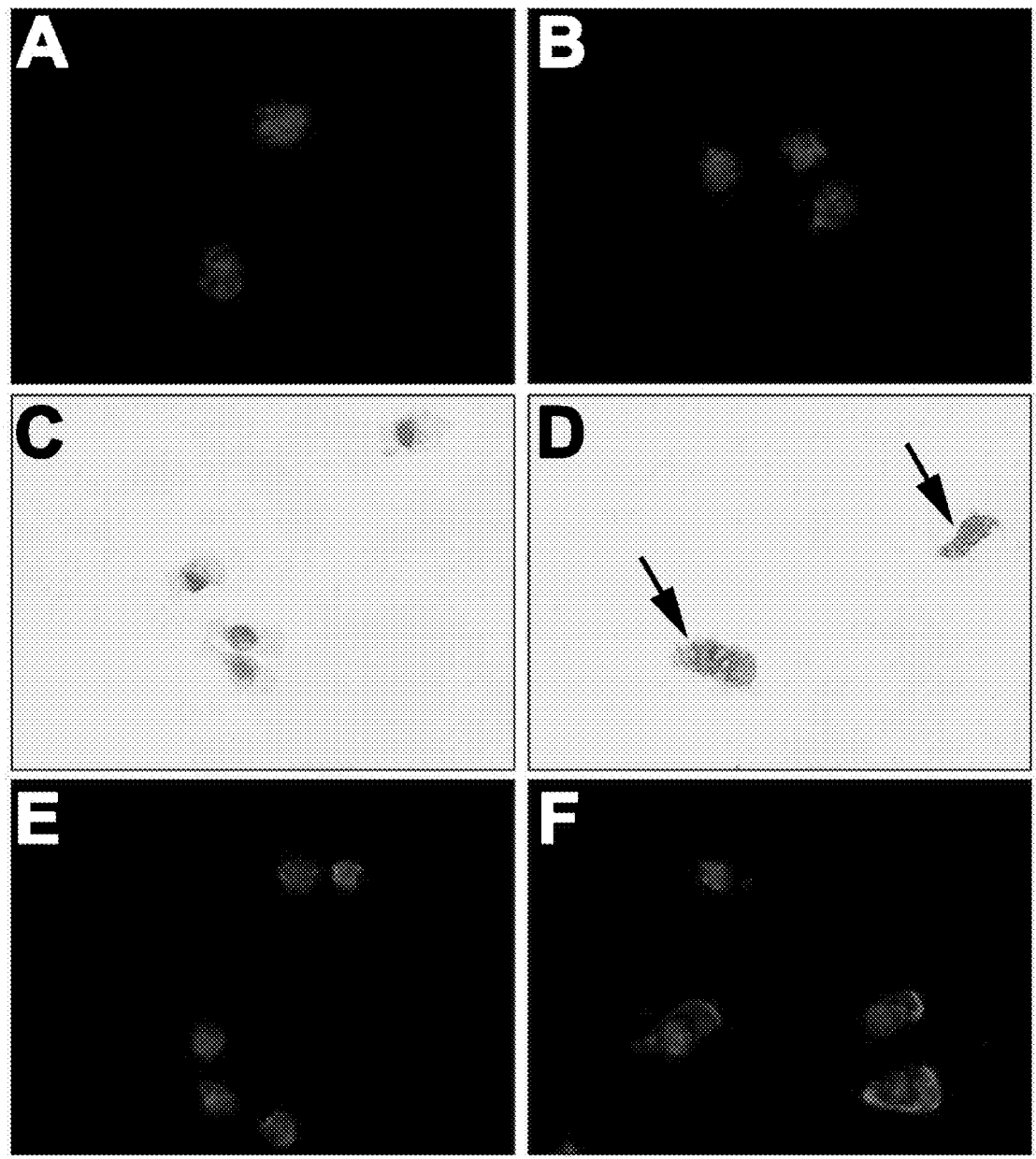

FIG. 30 illustrates that DCLK1 positive cells are less differentiated. A representative image of ALEXA FLUOR® 568 (Life Technologies Corp., Grand Island, N.Y.) conjugated DCLK1 positively sorted cells (A) (red) and negatively sorted cells (B) following FACS. (C) Brightfield image of L-FABP immunostaining. DCLK1 positive cells do not express L-FABP. (D) DCLK1 negative cells express L-FABP (brown—arrows). (E) Fluorescent image of L-FABP immunostaining. DCLK1 positive cells do not express L-FABP. (F) L-FABP was found in DCLK1 negative cells (green). Nuclei in A, B, E and F are stained blue with Hoechst 33342 DNA dye post-sorting.

FIG. 31 illustrates that DCLK1 (referred to as "DCAMKL-1" therein) inhibits let-7a miRNA. (A) Intestinal stem cells (DCLK1+) isolated from normal mouse intestine demonstrate decreased pri-let-7a compared to more differentiated cells (DCLK1-). (B) Real-time RT-PCR data demonstrate an increased expression of DCLK1 mRNA in DCLK1+ sorted stem cells compared to more differentiated (DCLK1-) cells. siRNA mediated knockdown of DCLK1 decreases luciferase activity (Relative Luciferase Units—RLU) following transfection with plasmid encoding luciferase containing let-7a binding site in HCT116 (C) and SW480 cells (D). For A-D, values are given as average±SEM and * denote statistically significant differences (*p<0.01) compared to control.

Figure 32:
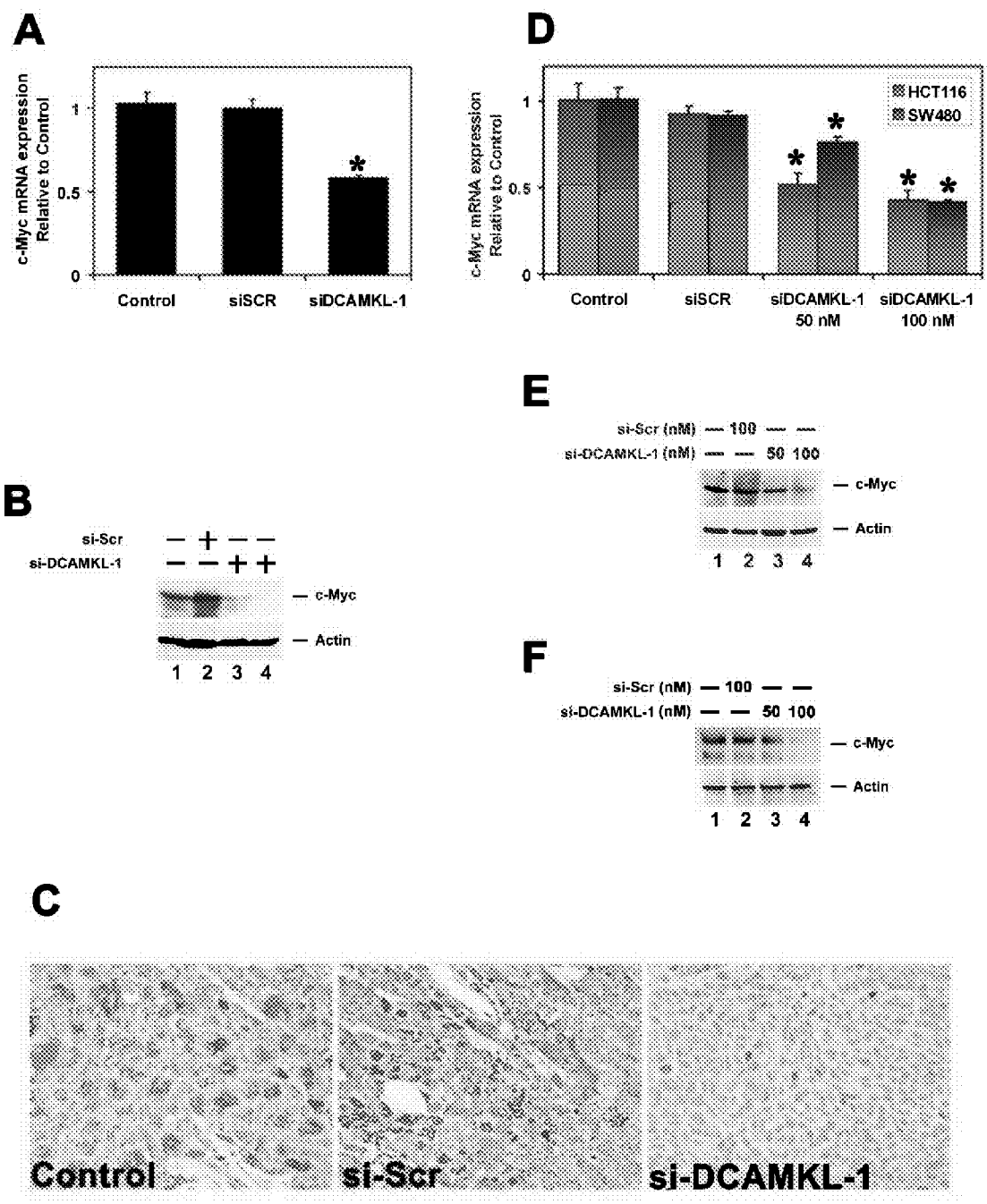

FIG. 32 illustrates that downregulation of DCLK1 (referred to as "DCAMKL-1" therein) results in decreased expression of a let-7a downstream target. A decreased expression of c-Myc mRNA (A) and protein (B) was observed in HCT116 tumor xenografts following the knockdown of DCLK1. (C) Decreased c-Myc expression (brown) in si-DCLK1 treated tumors compared to controls by immunohistochemical analysis. siRNA mediated knockdown of DCLK1 results in decreased c-Myc mRNA (D) and protein (E) in HCT116 cells. (D and F) Similar decrease was observed in SW480 cells. For bar graph in A and D, values are given as average±SEM and * denote statistically significant differences (p<0.01) compared to control.

Figure 33:
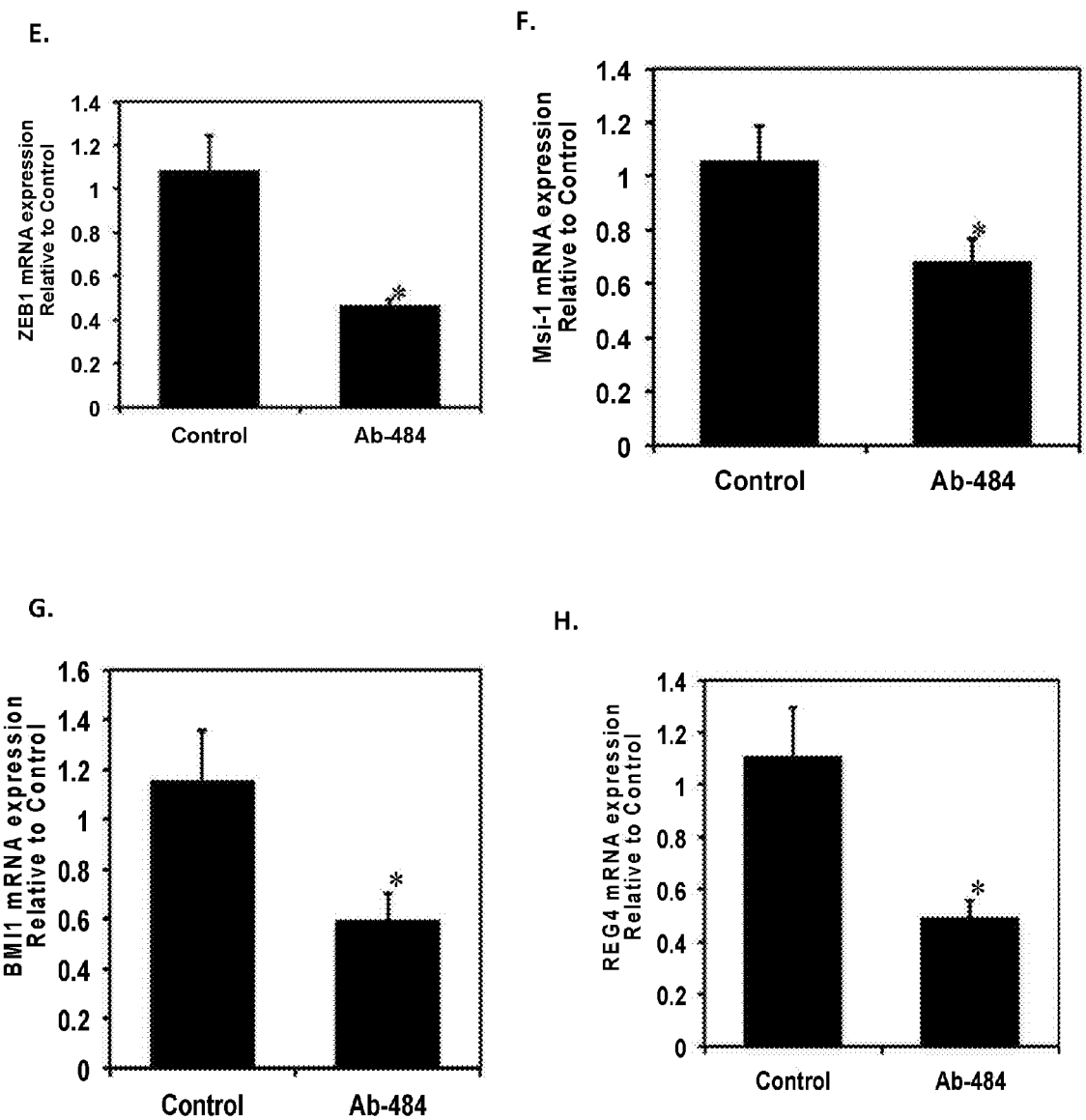

FIG. 33 illustrates that a monoclonal antibody (Ab-484) raised against DCLK1 inhibits DCLK1 mRNA (FIG. 33A), c-Myc mRNA (FIG. 33B), KRAS mRNA (FIG. 33C), Notch-1 mRNA (FIG. 33D), ZEB1 (FIG. 33E), Msi-1 mRNA (FIG. 33F), BMI1 mRNA (FIG. 33G), and REG4 mRNA (FIG. 33H) in the human pancreatic cancer cell line AsPC-1.

Figure 34:
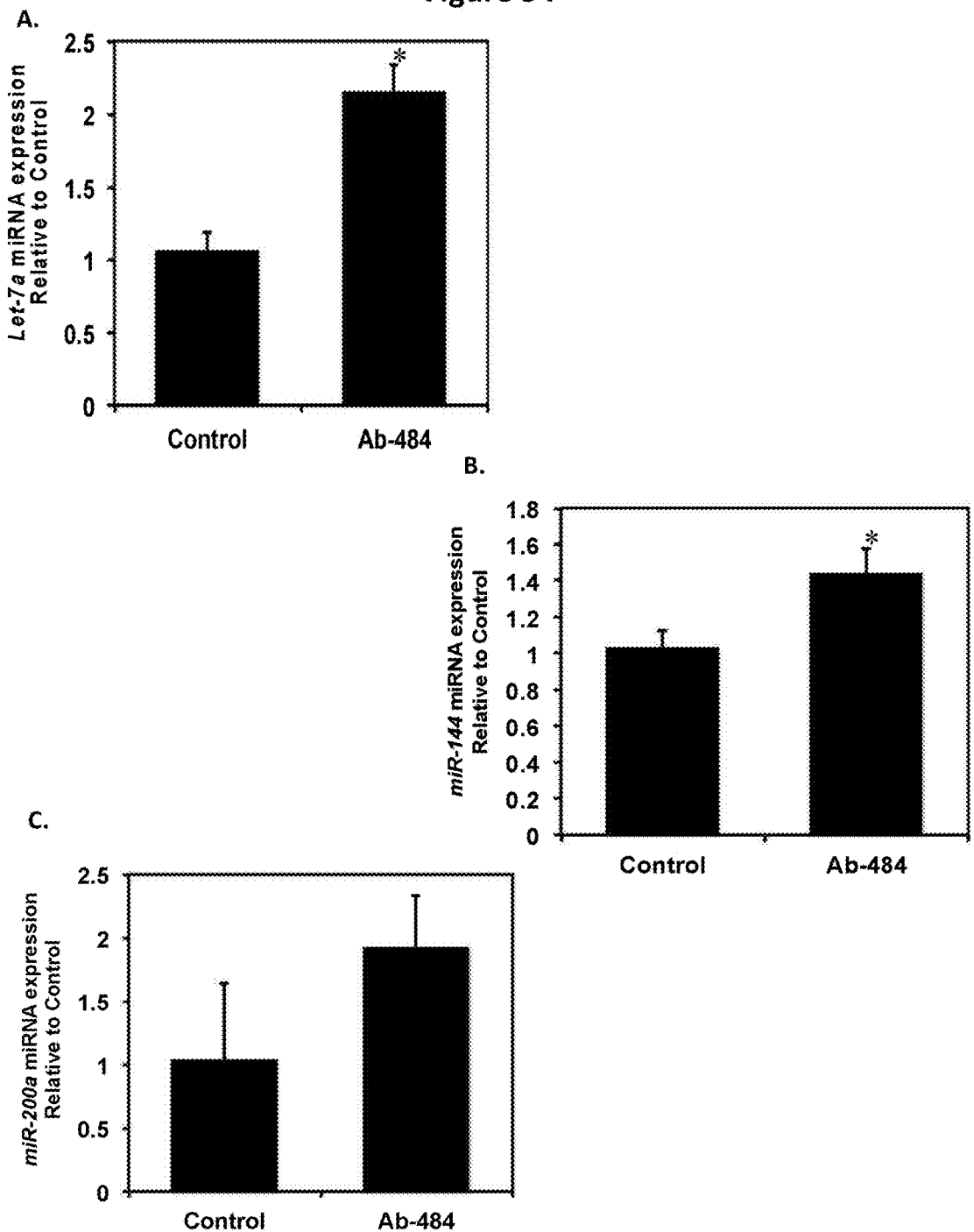

FIG. 34 illustrates that Ab-484 induces expression of the tumor suppressor miRNAs Let-7a (FIG. 34A), miR-144 (FIG. 34B), and mIR-200a (FIG. 34C) in AsPC-1 cells.

Figure 35:
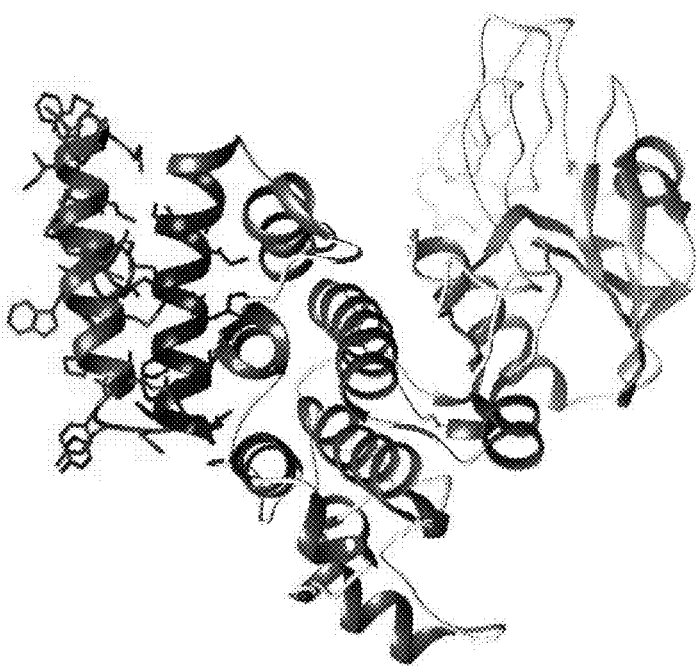

FIG. 35 contains a sequence alignment and a 3-dimensional structure of DCLK1 short-β isoform showing the peptides that were generated against two regions of the C-terminus thereof; peptide 700-729 (referred to herein as COARE-CT; SEQ ID NO:20) is indicated in red, peptide 680-709 (referred to herein as COARE-709; SEQ ID NO:21) is indicated in blue, and the overlap therebetween is shown in purple. The sequence alignment includes amino acids 661-729 of SEQ ID NO:2 (i.e., DCLK1 amino acid sequence).

Figure 36:
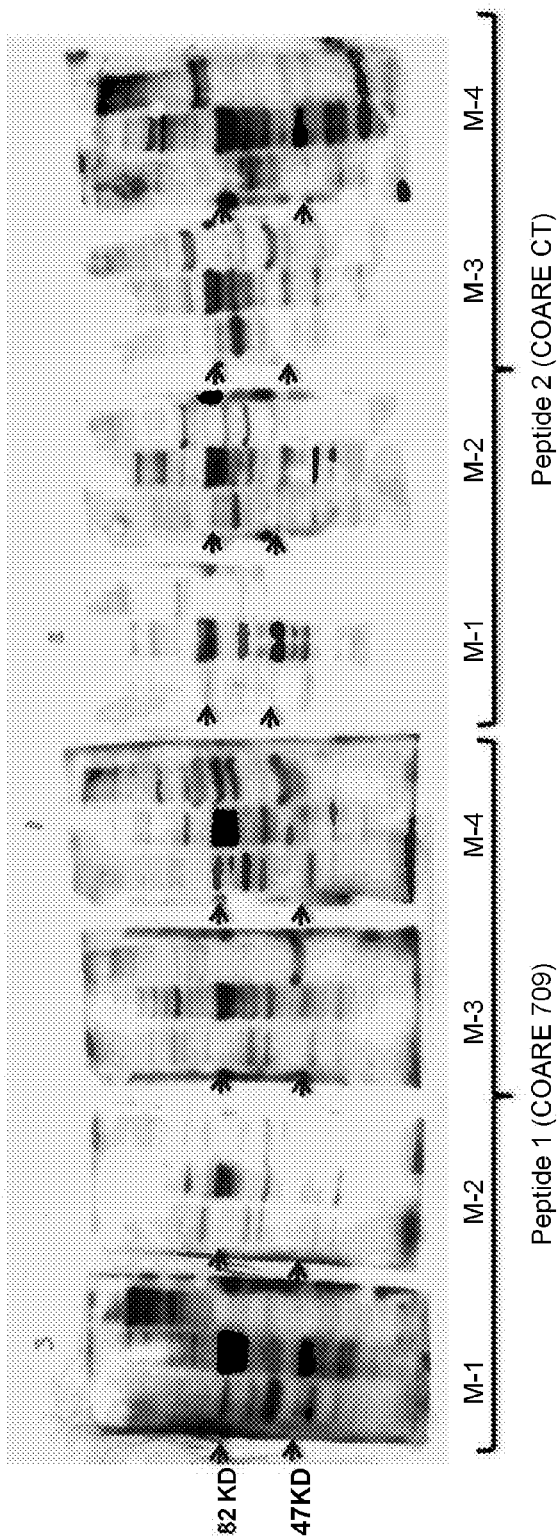

FIG. 36 contains a western blot analysis of serum from mice immunized with either of the peptides shown in FIG. 35.

Figure 37:
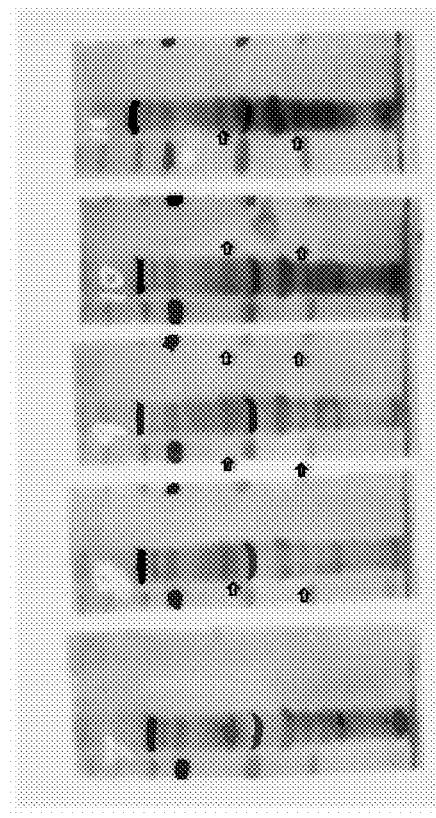

FIG. 37 illustrates a screening of hybridoma supernatants against various lysates for detection of long and short isoforms of DCLK1.

Figure 38:
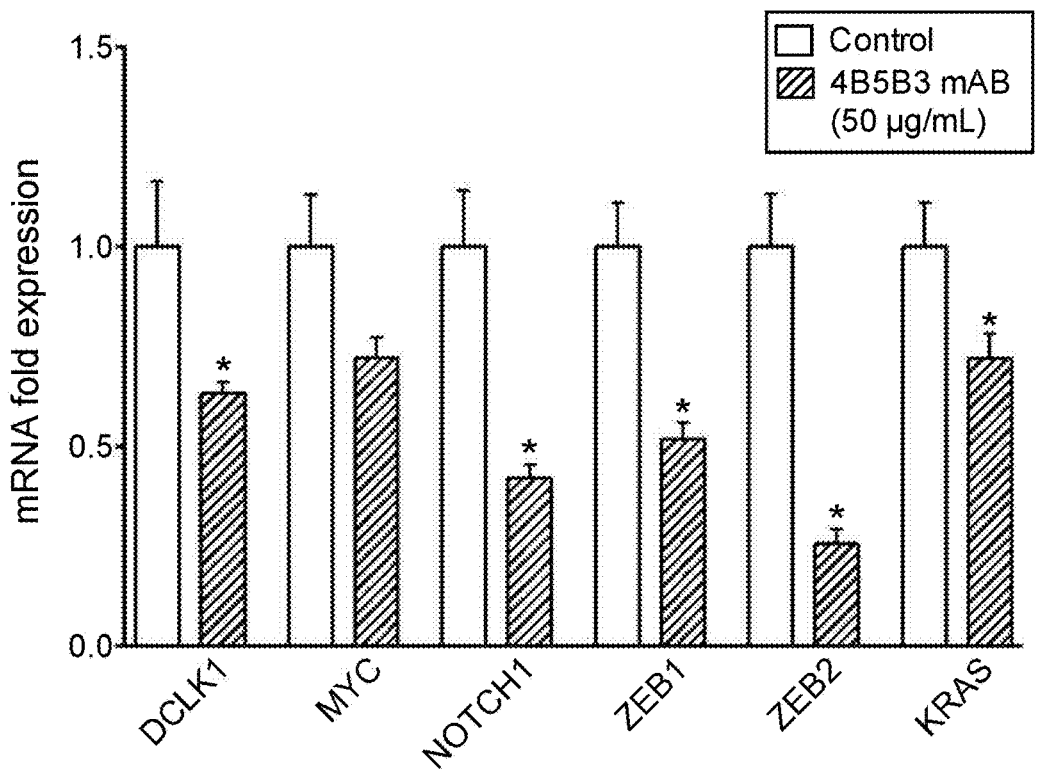

FIG. 38 illustrates the downregulation of DCLK1 and expression of key oncogenic and EMT-related mRNAs in AsPC-1 cells by 4B5B3.

Figure 39:
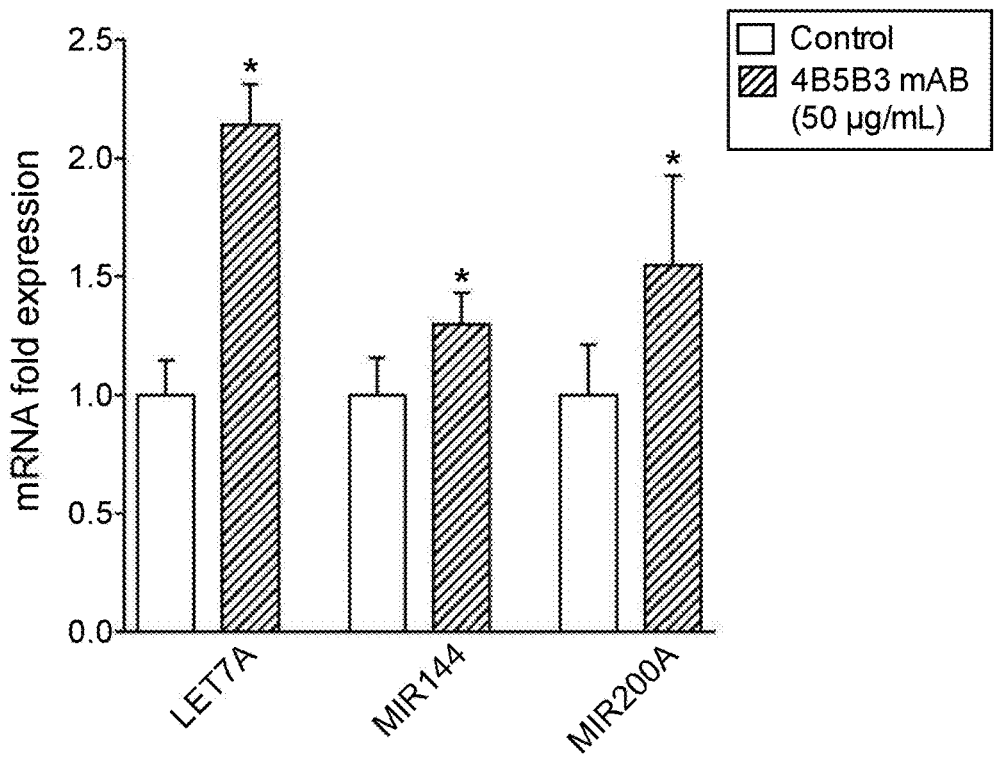

FIG. 39 illustrates upregulation of tumor suppressor miRNA expression levels in AsPC-1 cells by 4B5B3.

Figure 40:
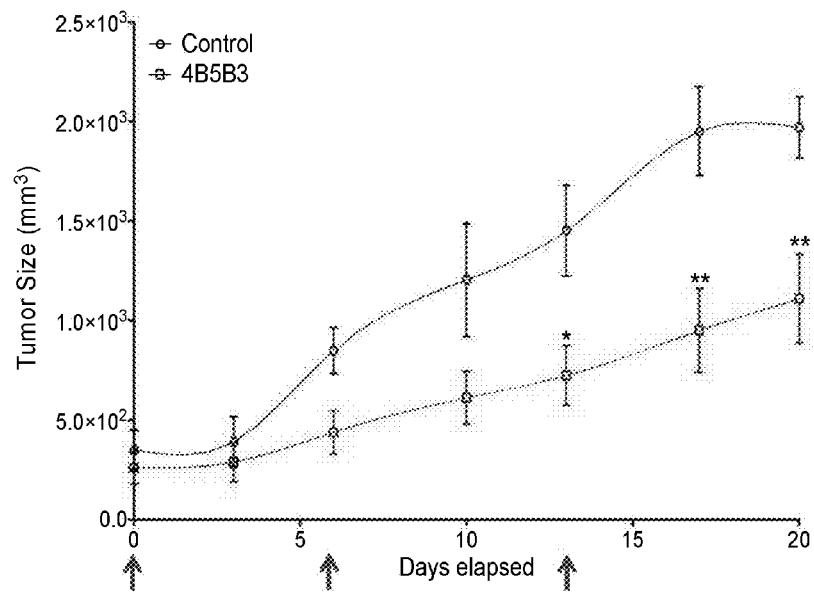

FIG. 40 illustrates the effect of 4B5B3 on tumor size in HCT116-DCLK1 tumor xenografts over a period of 20 days (the arrows denote injection dates).

FIG. 41A contains photos of a control tumor and a tumor treated with 4B5B3, while FIG. 41B graphically illustrates the observed difference in tumor volume.

Figure 42:
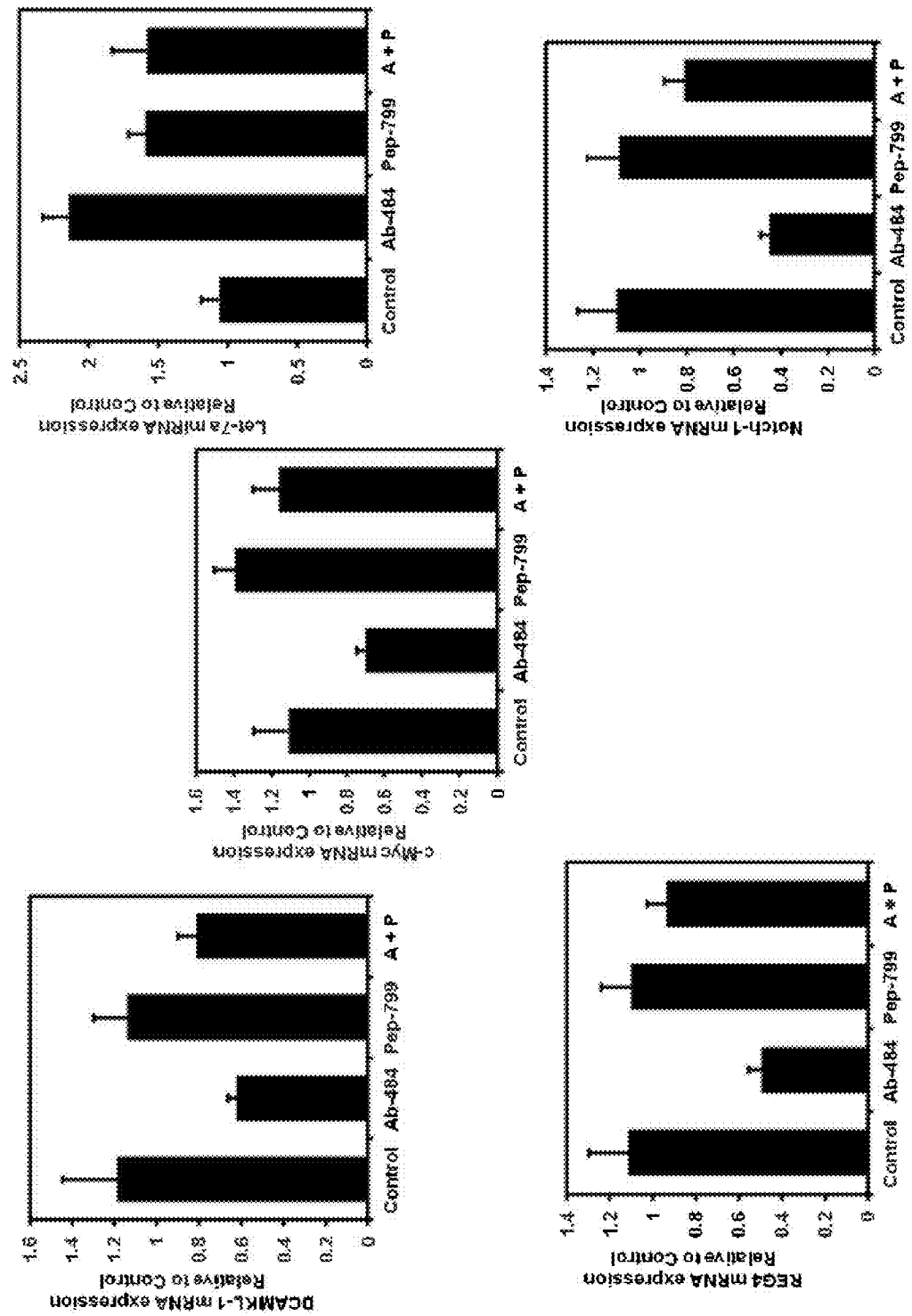
Figure 42:
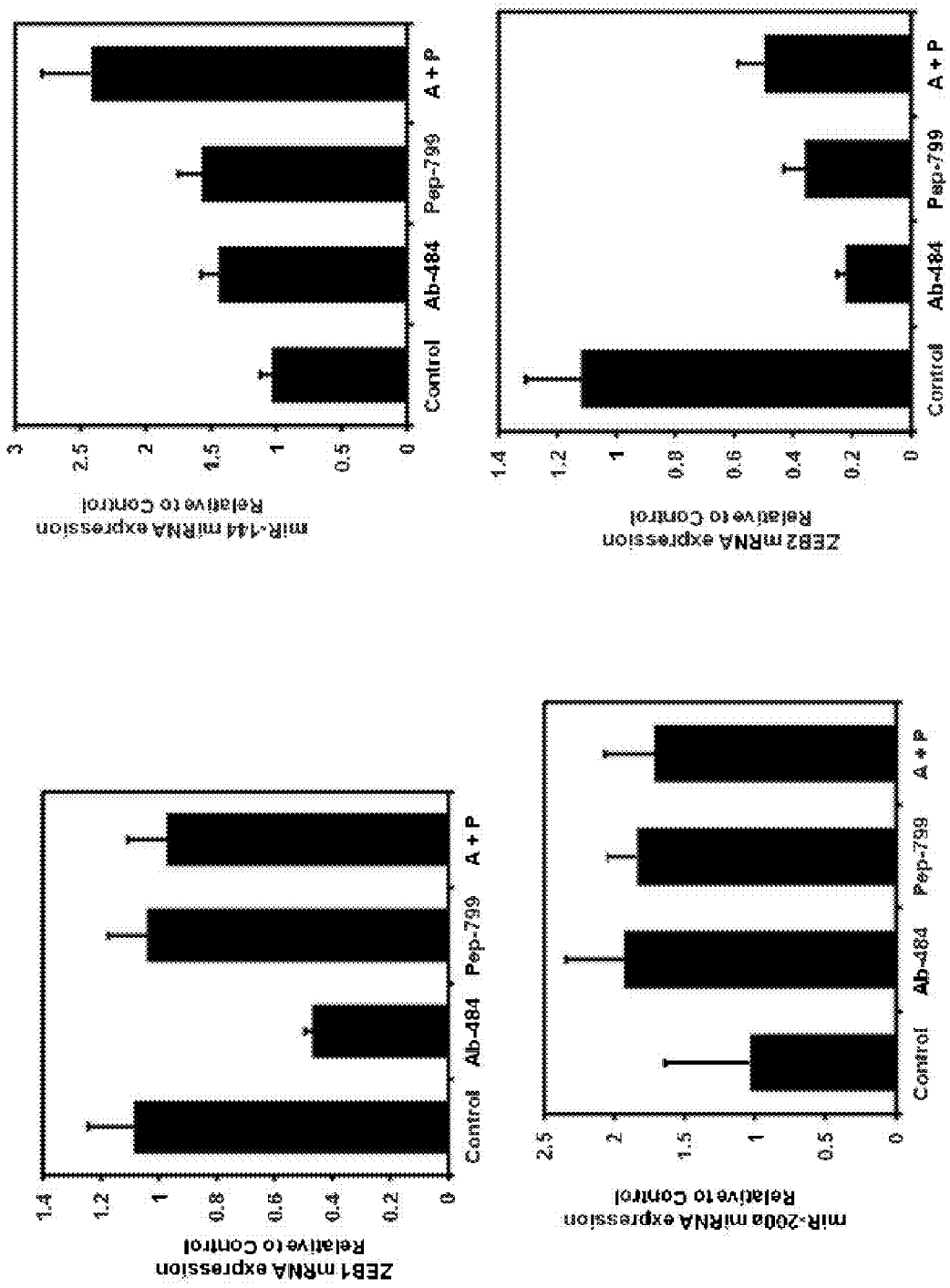

FIG. 42 illustrates the effect on expression of various genes in AsPc1 pancreatic cancer cells by Ab-484, a competitive DCLK1 peptide 799, or both antibody and peptide.

Figure 43:
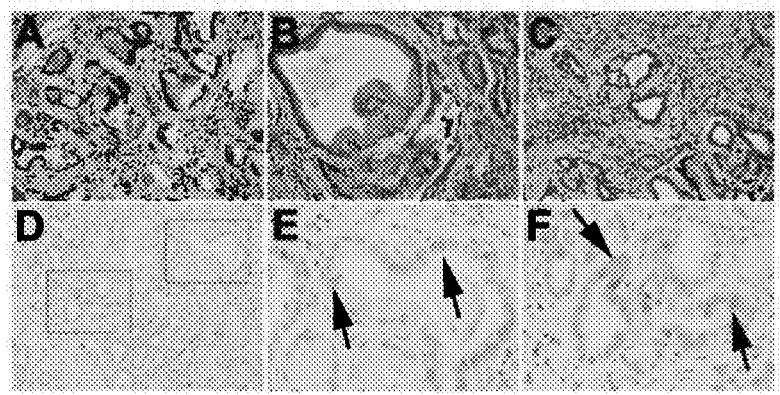

FIG. 43 illustrates pancreatic tissues from 10-month-old P48$^{cre}$-LSL-KRAS$^{G12D}$ demonstrating PanIN lesion Ia (A), IIa (B), and IIIa (C). Panels A-C are H&E staining. (D) Immunostaining demonstrates the presence of DCLK1 (brown—indicated by arrows) in the PanIN lesions. (E) and (F) are magnified images of a portion of (D).

Figure 44:
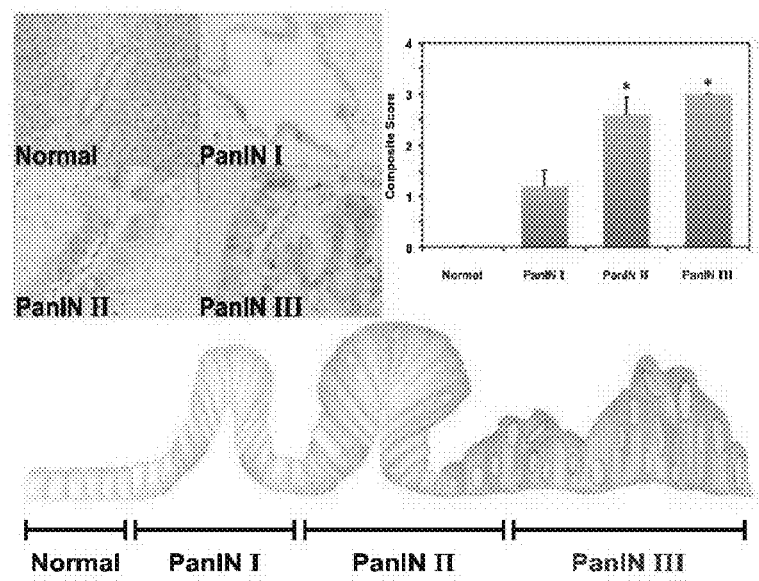

FIG. 44 illustrates that DCLK1 is correlated with PanIN stage. Immunohistochemical staining of DCLK1 (Brown) in human pancreatic normal ducts and PanIN lesions, composite scoring of DCLK1 expression (n=6 per group), and stage-wise depiction of DCLK1 epithelial expression.

Figure 45:
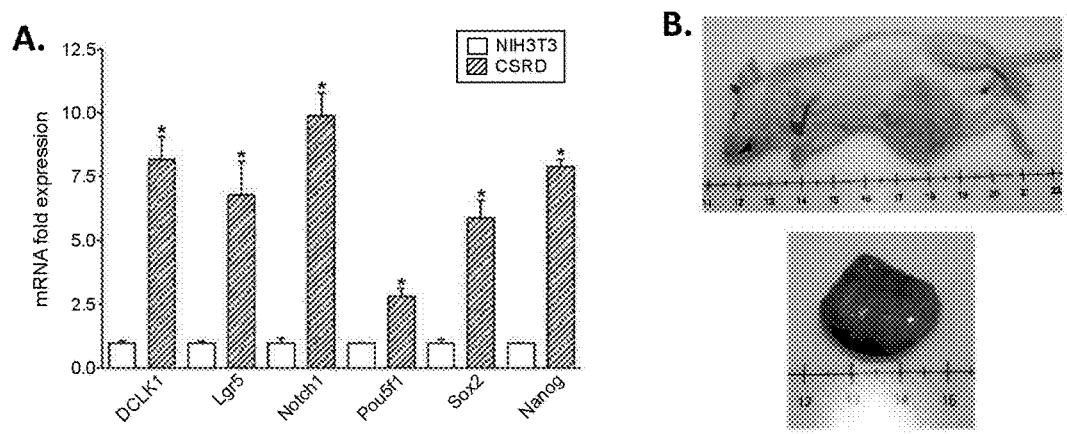

FIG. 45A illustrates stemness factor mRNA expression in CSRD1 and NIH3T3 control cell lines. All were statistically significant. Myc mRNA expression is not shown but was upregulated more than 100-fold. FIG. 45B illustrates a CSRD1 tumor in NOD/SCID mouse and corollary excised tumor.

Figure 46:
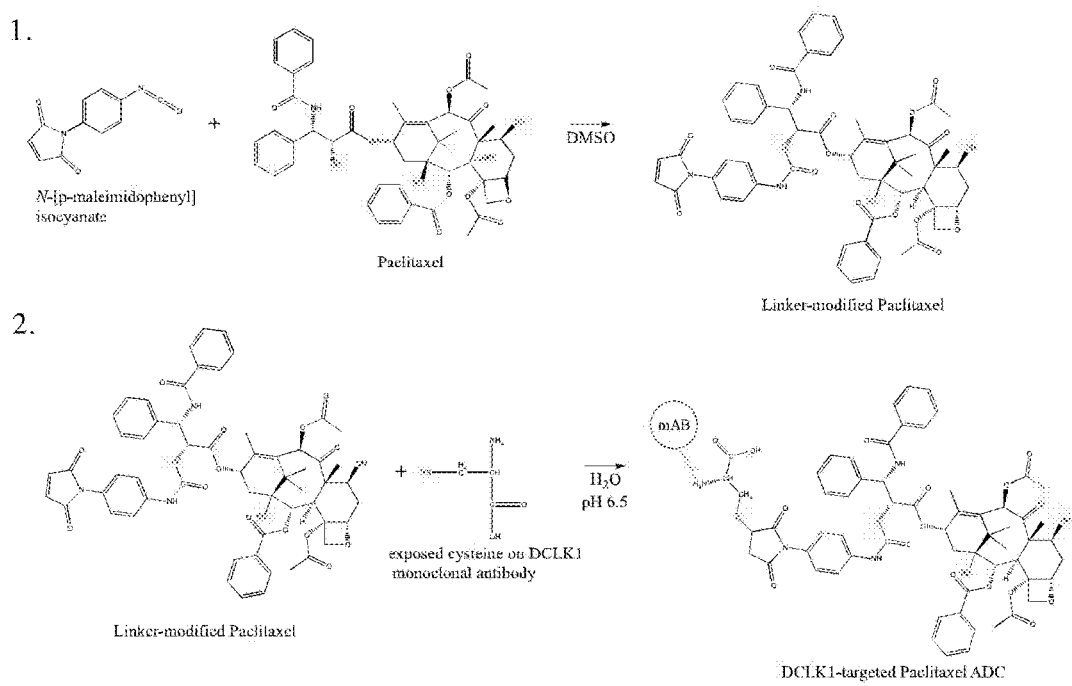

FIG. 46 schematically illustrates the synthesis of an antibody-drug conjugate constructed in accordance with the presently disclosed and claimed inventive concept(s). Reaction (1) illustrates the synthesis of Linker-modified Paclitaxel. Reaction (2) illustrates the use of the Linker-modified Paclitaxel produced in Reaction (1) in the synthesis of a DCLK1-targeted Paclitaxel antibody drug conjugate (ADC).

DETAILED DESCRIPTION

Before explaining at least one embodiment of the presently disclosed and claimed inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this presently disclosed and claimed inventive concept(s) have been described in terms of particular embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Throughout the specification and claims, unless the context requires otherwise, the terms "substantially" and "about" will be understood to not be limited to the specific terms qualified by these adjectives/adverbs, but allow for minor variations and/or deviations that do not result in a significant impact thereto. For example, in certain instances the term "about" is used to indicate that a value includes the inherent variation of error for the device, the method being employed to determine the value and/or the variation that exists among study subjects. Similarly, the term "substantially" may also relate to 80% or higher, such as 85% or higher, or 90% or higher, or 95% or higher, or 99% or higher, and the like.

The terms "isolated polynucleotide" and "isolated nucleic acid segment" as used herein shall mean a polynucleotide of genomic, cDNA, or synthetic origin or some combination thereof, which by virtue of its origin the "isolated polynucleotide" or "isolated nucleic acid segment" (1) is not associated with all or a portion of a polynucleotide in which the "isolated polynucleotide" or "isolated nucleic acid segment" is found in nature, (2) is operably linked to a polynucleotide which it is not linked to in nature, or (3) does not occur in nature as part of a larger sequence.

The term "isolated protein" referred to herein means a protein of genomic, cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or, (4) does not occur in nature.

The term "polypeptide" as used herein is a generic term to refer to native protein, fragments, or analogs of a polypeptide sequence. Hence, native protein, fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

"Antibody" or "antibody peptide(s)" refer to an intact antibody, or a binding fragment thereof that competes with the intact antibody for specific binding. The term "antibody" is used in the broadest sense, and specifically covers monoclonal antibodies (including full length monoclonal antibodies), polyclonal antibodies, multispecific antibodies (e.g., bispecific antibodies), and antibody fragments (e.g., Fab, F(ab')2 and Fv) so long as they exhibit the desired biological activity. Antibodies (Abs) and immunoglobulins (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. Antibody binding fragments are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

As used herein, the phrase "associated with" includes covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The term "purified" as used herein means at least one order of magnitude of purification is achieved compared to the starting material or of the natural material, for example but not by way of limitation, two, three, four or five orders of magnitude of purification of the starting material or of the natural material. Thus, the term "purified" as utilized herein does not necessarily mean that the material is 100% purified, and therefore such term does not exclude the presence of other material(s) present in the purified composition.

The terms "DCAMKL-1," "Doublecortin-like and CAM kinase kinase-like 1," "doublecortin and $Ca^{2+}$/calmodulin-dependent kinase-like-1," "DCLK1" and "Gene Ontogeny (GO)-enriched transcript" will be used herein interchangeably and will be understood to refer to a microtubule-associated kinase expressed in post-mitotic neurons. See for example, Shu et al. (2006a and b). Its presence was identified from cDNA libraries prepared from laser capture microdissected small intestinal and gastric epithelial progenitor populations.

The terms "RNA binding motif protein 3" and "RBM3" are used interchangeably herein and will be understood to refer to a putative stem cell marker. RBM3 is a ubiquitously expressed glycine-rich protein that can bind to both RNA and DNA via an amino-terminal RNA binding domain. RBM3 was identified as a protein expressed following cold shock and was found in the complex of proteins binding to COX-2.

The terms "Musashi-1" and "Msi-1" are used interchangeably herein and will be understood to refer to a putative stem cell marker. Msi-1 was identified as an RNA binding protein that is a translational repressor of p21. Msi-1 regulates asymmetrical division in neural precursor cells, and is expressed in intestinal crypts in the stem cell zone.

The terms "Leucine-rich repeat-containing G-protein coupled receptor 5" and "LGR5" are used interchangeably herein and will be understood to refer to a putative stem cell marker. LGR5 is a leucine-rich orphan G-protein-coupled receptor that specifically labels stem cells in the mouse small intestine as well as other adult tissues.

The term "14-3-3σ" refers to a putative stem cell marker. The 14-3-3 σ gene (also called stratifin) was originally characterized as the human mammary epithelial-specific marker, HME-1, and is expressed in keratinocytes and epithelial cells. 14-3-3 σ is up-regulated through a p53-dependent mechanism following DNA damage, and sequesters cyclin B1/CDC2 complexes in the cytoplasm during G2 arrest. Its absence allows cyclin B1/CDC2 complexes to enter the nucleus, causing mitotic catastrophe. 14-3-3σ has also been shown to specifically interact with CDK2, CDC2 and CDK4 and to inhibit CDK activities, thereby blocking cell cycle progression, thus defining it as a new class of CKI. Deregulation of 14-3-3σ expression has been observed in a wide variety of human cancers, with both decreasing and increasing 14-3-3σ levels being associated with development of malignancy.

The term "Bmi1" will be understood to refer to a putative stem cell marker. The Bmi1 gene is known to be involved in the self-renewal of neuronal, hematopoietic and leukemic cells. Bmi1 was first identified in a mouse proviral insertion screen for lymphomagenesis. It is part of the Polycomb group gene family, and specifically a member of polycomb-repressing complex 1 (PRC1). PRC1 has an essential role in maintaining chromatin silencing.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA. It is believed that the siRNA and the targeted mRNA bind to an "RNA-induced silencing complex" or "RISC," which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Specific methods of using siRNAs are described in detail in U.S. Pat. No. 7,345,027, issued to Tolentino et al. on Mar. 18, 2008; U.S. Pat. No. 7,148,342, issued to Tolentino et al. on Dec. 12, 2006; U.S. Pat. No. 7,511,025, issued to Wyatt et al. on Mar. 31, 2009; and U.S. Pat. No. 7,511,132, issued to Khvorova et al. on Mar. 31, 2009; the entire contents of such patents are expressly incorporated herein by reference. These patents describe siRNAs which specifically target and cause RNAi-induced degradation of mRNA, such as RNA from VEGF and VEGF receptors, MMP-1 and BCL-2, respectively, and such siRNA compounds may be used to suppress invasion and/or metastasis of tumor cells and/or inhibit angiogenesis, in particular for the treatment of cancerous tumors, age-related macular degeneration, and other angiogenic diseases. The methods of these patents may be applied to the production and use of siRNAs in accordance with the presently disclosed and claimed inventive concept(s).

The term "biological sample" as used herein will be understood to refer to a sample of biological tissue or fluid. Biological samples include, but are not limited to, sections of tissues such as biopsy and autopsy samples, frozen sections taken for histological purposes, blood, plasma, serum, sputum, stool, tears, mucus, hair, skin, explants and primary and/or transformed cell cultures derived from patient tissues.

The phrase "providing a biological sample" as used herein refers to obtaining a biological sample for use in methods described in the inventive concept(s). Most often, this will be done by removing a sample of cells from an animal, but can also be accomplished by using previously isolated cells (e.g., isolated by another person, at another time and/or for another purpose), or by performing at least a portion of the methods of the inventive concept(s) in vivo.

As used herein, a "conjugate" refers to a molecule that contains at least one receptor-binding ligand and at least one anticancer agent that are coupled directly or via a linker and that are produced by chemical coupling methods or by recombinant expression of chimeric DNA molecules to produce fusion proteins.

As used herein, the term "covalently coupled," "linked," "bonded," "joined," and the like, with reference to the ligand and anticancer agent components of the conjugates of the presently disclosed and claimed inventive concept(s), mean that the specified components are either directly covalently bonded to one another or indirectly covalently bonded to one another through an intervening moiety or components, such as a bridge, spacer, linker or the like. For example but not by way of limitation, the ligand and the anticancer agent may be chemically coupled together via a thioether linkage as described in Mickisch et al. (1993).

As used herein, the term "anticancer agent" refers to a molecule capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent is selectively toxic against certain types of cancer cells but does not affect or is less effective against other normal cells.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the disease in conjunction with the pharmaceutical compositions of the presently disclosed and claimed inventive concept(s). This concurrent therapy can be sequential therapy where the patient is treated first with one drug and then the other, or the two drugs are given simultaneously.

The terms "administration" and "administering," as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The term "receptor" as used herein will be understood to include any peptide, protein, glycoprotein, polycarbohydrate, or lipid that is uniquely expressed or overexpressed on the surface of cancer cells and is exposed on the surface of cancer cells in a manner that will allow interaction with a circulating targeting agent, such as the conjugate.

As used herein, "substantially pure" means an object species is the predominant species present (i.e., on a molar basis it is more abundant than any other individual species in the composition), and in certain embodiments, a substantially purified fraction is a composition where the object species comprises at least about 50 percent (on a molar basis) of all macromolecular species present. Generally, a substantially pure composition will comprise more than about 80 percent of all macromolecular species present in the composition, more particularly more than about 85%, 90%, 95%, and 99%. In certain non-limiting embodiments, the object species is purified to essential homogeneity (contaminant species cannot be detected in the composition by conventional detection methods) wherein the composition consists essentially of a single macromolecular species.

A "liposome" is a small vesicle composed of various types of lipids, phospholipids and/or surfactant. The components of the liposome are commonly arranged in a bilayer formation, similar to the lipid arrangement of biological membranes.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma, and various types of head and neck cancer.

The term "metastasis" as used herein will be understood to refer to the spread of cancer from a primary tumor to other parts of the body. Metastasis is a sequential, multistep process in which tumor cells detach from a primary tumor, migrate through the basement membrane and extracellular matrix, and invade the lymphatic and/or blood systems. This is followed by the establishment of secondary tumors at distant sites.

The term patient includes human and veterinary subjects. "Mammal" for purposes of treatment refers to any animal classified as a mammal, including human, domestic and farm animals, nonhuman primates, and any other animal that has mammary tissue.

The term "healthy patient" as used herein will be understood to refer to a patient who is free of cancer.

The terms "treat," "treating," and "treatment," as used herein, will be understood to include both inhibition of tumor growth as well as induction of tumor cell death.

As used herein, the term "treating cancer" or "treatment of cancer" means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

"Preventing cancer" or "prevention of cancer" is intended to mean preventing the occurrence or recurrence of the disease state of cancer. As such, a treatment that impedes, inhibits, or interferes with metastasis, tumor growth, or cancer proliferation is deemed preventive.

As used herein, "managing cancer" encompasses preventing the recurrence of cancer in a patient who had suffered from cancer, lengthening the time a patient remains in remission, preventing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and preventing the occurrence of malignant cancer in patients suffering from pre-malignant or non-malignant cancers.

Administering a therapeutically effective amount or prophylactically effective amount is intended to provide a therapeutic benefit in the treatment, prevention, or management of cancer. The specific amount that is therapeutically effective can be readily determined by the ordinary medical practitioner, and can vary depending on factors known in the art, such as the type of cancer, the patient's history and age, the stage of cancer, the co-administration of other anticancer agents, including radiation therapy.

Turning now to the particular embodiments of the presently disclosed and claimed inventive concept(s), methods of inhibiting tumor growth are provided. Such methods involve an inhibition of doublecortin and $Ca^{2+}$/calmodulin-dependent kinase-like-1 (DCLK1) protein in the tumor cells. Such method results in a decrease in cancer cell proliferation and apoptosis, as well as $G_2$/M arrest, coupled with mitotic catastrophe. Inhibition of DCLK1 may also result in a decrease in mRNA stability and/or translation for the gene products of at least one of c-Myc, KRAS, and combinations thereof, and may also result in an increase in miRNA expression, such as but not limited to, pri-let-7a miRNA expression.

Inhibition of DCLK1 may involve inhibition of DCLK1 expression and/or DCLK1 activity. Inhibition of DCLK1 expression and/or activity may occur by any method known in the art or otherwise contemplated herein. In certain embodiments, DCLK1 expression and/or activity may be inhibited through the use of a specific binding agent for DCLK1. The term "specific binding agent" as used herein will be understood to include any compound or agent that binds specifically to DCLK1 protein, including but not limited to, a receptor for DCLK1 protein, a lectin binding to DCLK1 protein, or an antibody to DCLK1 protein. As the skilled artisan will appreciate, the term "specific" is used to indicate that other biomolecules present in the sample do not significantly bind to the binding agent specific for DCLK1 protein. A level of less than 5% cross-reactivity is considered not significant.

In one embodiment, the specific binding agent is an antibody reactive with DCLK1 protein. The term "antibody" refers to a polyclonal antibody, a monoclonal antibody, fragments of such antibodies, as well as to genetic constructs comprising the binding domain of an antibody. Non-limiting particular examples of monoclonal antibodies that may be utilized in accordance with the presently disclosed and claimed inventive concept(s) include antibodies targeting the extracellular C-terminal domain of DCLK1 isoforms 1-4. For example but not by way of limitation, this region is located in amino acids 648-729 of the isoform 1 sequence (i.e., DDGLPENEHQLSVAGKIKKHFNTGPKPN-STAAGVSVIALDHGFTIKRSGSLDYYQQPGMYWIRP-PLLIRRGRF SDEDATRM; SEQ ID NO:16); in amino acids 648-740 of the isoform 2 sequence (i.e., DDGLPENE-HQLSVAGKIKKHFNTGPKPNSTAAGVSVIATTALDK-ERQVFRRRRNQDVRSRYKAQPAPPELNS ESEDYSPSSSETVRSPNSPF; SEQ ID NO:17); in amino acids 341-422 of the isoform 3 sequence (i.e., DDGLPENE-HQLSVAGKIKKHFNTGPKPNSTAAGVSVIALDHGF-TIKRSGSLDYYQQPGMYWIRP PLLIR RGRFSDE-DATRM; SEQ ID NO:18); and in amino acids 341-433 of the isoform 4 sequence (i.e., DDGLPENEHQLSVAGKIK-KHFNTGPKPNSTAAGVSVIATTALDKERQVFRRRRN-QDVRSRYKAQPAPPELN; SEQ ID NO:19). In particular, non-limiting embodiments, the isolated monoclonal antibody or antigen binding fragment thereof specifically binds to a polypeptide comprising amino acids 700-729 (SEQ ID NO:20) and/or amino acids 680-709 (SEQ ID NO:21) of the isoform 1 sequence.

The monoclonal antibody or other specific binding agent may further comprise a label, such as but not limited to, a radiolabel or fluorescent label, to aid in visualization of tumor cells with an external imaging source, such as but not limited to, an MRI or PET scan. The use of a label allows one to track the inhibition of tumor growth by the specific binding agent.

In another embodiment, the expression of DCLK1 protein can be inhibited using any well known method that targets the RNA binding protein's gene or its mRNA. These methods include, but are not limited to, the use of antisense oligonucleotides, ribozymes, nucleic acid molecules that promote triple helix formation, and short-interfering RNAs (siRNAs) or co-repression of a target gene by introducing a homologous gene fragment into the cell that harbors the target gene. In particular embodiments, the methods of the presently disclosed and claimed inventive concept(s) employ siRNAs that specifically reduce expression of DCLK1 protein.

In one embodiment, the expression of DCLK1 protein is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA.

RNAi can be performed, for example, using chemically-synthesized RNA. Alternatively, suitable expression vectors can be used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using *E. coli* RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp et al. (2002); Lee et al. (2002); Miyagashi and Taira (2002); Paddison et al. (2002); Paul et al. (2002); and Sui et al. (2002). Various methods for introducing such vectors into cells, either in vitro or in vivo (e.g., gene therapy), are known in the art.

Kits for production of dsRNA for use in RNAi are available commercially, e.g., from New England Biolabs, Inc. (Ipswich, Mass.) and Ambion Inc. (Austin, Tex., USA). Methods of transfection of dsRNA or plasmids engineered to make dsRNA are routine in the art.

The methods described herein may be utilized for treatment of any cancer, including but not limited to, cancers of the gastrointestinal tract, colon, pancreas, breast, prostate, lung and ovaries. Particular cancers that can be treated and managed by the methods of the presently disclosed and claimed inventive concept(s) include, but are not limited to, those associated with an increase in the expression of DCLK1 protein.

In one embodiment, the presently disclosed and claimed inventive concept(s) is directed to a short-interfering ribonucleic acid (siRNA) molecule effective at silencing DCLK1 expression. The siRNA molecule comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in DCLK1 mRNA (or a homolog thereof). The DCLK1 target sequence that binds the siRNA can be selected experimentally or empirically. In certain embodiments, the DCLK1 mRNA may be in accordance with SEQ ID NO:1, or the DCLK1 mRNA may encode the amino acid sequence of SEQ ID NO:2; in particular embodiments, the sense RNA strand may include SEQ ID NO:3, as described in greater detail herein after.

Alternatively, depending on the conditions under which binding is sufficient to disrupt the function of the DCLK1 gene, a sequence complementary to a target sequence within the DCLK1 nucleic acid sequences need not be 100 percent identical to the target sequence. For example, a sequence can be complementary to its target sequence when at least about 80 or 90 percent of its nucleotides bind via matched base pairings with nucleotides of the target sequence.

Therefore, the sense RNA strand may comprise a sequence homologous to a portion of SEQ ID NO:1 (or a mRNA encoding SEQ ID NO:2) that is capable of hybridizing to its target sequence under stringent conditions. In general, for complementary sequences to hybridize under stringent conditions, said sequences are at least 80 or 90 percent identical to each other. One non-limiting example of stringent hybridization conditions includes 6× sodium chloride/sodium citrate (SSC) at about 45° C., followed by 0.2×SSC, 0.1% SDS at 50-65° C. Thus, the presently disclosed and claimed inventive concept(s) also includes siRNAs having a sense RNA strand that comprises a nucleotide sequence that is at least 90% identical to a target sequence of about 15 to about 25 contiguous nucleotides in DCLK1 mRNA (or a homolog thereof).

The siRNAs of the presently disclosed and claimed inventive concept(s) may include modifications to their sugar-phosphate backbone or nucleosides. These modifications can be tailored to promote selective genetic inhibition, while avoiding a general panic response reported to be generated by siRNA in some cells. Moreover, modifications can be introduced in the bases to protect siRNAs from the actin of one or more endogenous degradative enzymes.

The presently disclosed and claimed inventive concept(s) also includes a pharmaceutical composition comprising any of the specific DCLK1 binding agents (such as but not limited to, any of the monoclonal antibodies or antigen binding fragments thereof disclosed or otherwise contemplated herein) and/or siRNA molecules described herein above in combination with a pharmaceutically acceptable carrier. The pharmaceutical composition may further comprise at least one additional chemotherapeutic agent, as described in detail herein. In addition, the pharmaceutical composition may also further comprise a delivery agent, such as but not limited to, a liposome. In addition, the pharmaceutical composition may include other small molecules that act synergistically with the specific DCLK1 binding agent and/or siRNA; non-limiting examples of small molecules that may be utilized include protein kinase inhibitors, cytotoxins, epigenetic modulators, or other agents that function in accordance with the presently disclosed and claimed inventive concept(s).

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the inventive concept(s) from degradation within the gastrointestinal tract. In another example, the agents of the inventive concept(s) may be administered in a liposomal formulation to shield the agents from degradative enzymes, facilitate transport in circulatory system, and effect delivery across cell membranes to intracellular sites.

The composition, shape, and type of dosage forms of the pharmaceutical compositions of the presently disclosed and claimed inventive concept(s) will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the inventive concept(s) will vary from one another and will be readily apparent to those skilled in the art. See, e.g., Remington: The Science and Practice of Pharmacy, Alfonso R. Gennaro, editor, 20th ed. Lippincott Williams & Wilkins: Philadelphia, Pa., 2000.

The presently disclosed and claimed inventive concept(s) further includes kits useful for in any of the methods described herein; the kit may contain any single pharmaceutical composition described herein, as well as combinations of the above-described pharmaceutical compositions; in addition, the kit may further contain other reagent(s) for performing any of the particular methods described or otherwise contemplated herein. The nature of these additional reagent(s) will depend upon the particular method format, and identification thereof is well within the skill of one of ordinary skill in the art.

Individual dosages of pharmaceutical compositions may each be in separate containers/compartments, or multiple dosages of pharmaceutical compositions can be provided in one or more containers/compartments, depending on the cross-reactivity and stability of the components/reagents. The kit can further include other separately packaged reagents. In addition, the kit may include an administration device in which the pharmaceutical composition(s) is disposed. The kit can further include positive and/or negative controls and/or a set of written instructions explaining how to use the kit. A kit of this nature can be used in any of the methods described or otherwise contemplated herein.

In one embodiment, the presently disclosed and claimed inventive concept(s) also includes a method of inhibiting expression of DCLK1 protein. Said method includes providing a cell expressing DCLK1 and providing the specific DCLK1 binding agent and/or siRNA molecule described herein above; the cell is then contacted with the specific DCLK1 binding agent and/or siRNA, thereby specifically inhibiting the expression of DCLK1.

The presently disclosed and claimed inventive concept(s) also includes a method of inhibiting expression of DCLK1 protein in a subject. In said method an effective amount of any of the pharmaceutical compositions described herein above is administered to the subject, thereby specifically inhibiting the expression of DCLK1.

The presently disclosed and claimed inventive concept(s) further includes a method of inhibiting tumor growth. In said method, at least one of the specific DCLK1 binding agents and/or siRNAs described herein above is provided and contacted with the tumor, thereby specifically inhibiting the expression and/or activity of DCLK1 in the tumor and thus inhibiting growth of the tumor. Said method may result in at least one of (1) a decrease in cancer cell proliferation, apoptosis, $G_2$/M arrest, mitotic catastrophe; (2) a decrease in at least one of mRNA stability and mRNA translation for at least one protein selected from the group consisting of c-Myc, KRAS and combinations thereof; and (3) an increase in miRNA expression, such as pri-let-7a miRNA expression.

The presently disclosed and claimed inventive concept(s) also includes a method of inhibiting tumor growth in a subject, which includes providing at least one of the pharmaceutical compositions described herein above and administering an effective amount thereof to the subject, thereby specifically inhibiting the expression and/or activity of DCLK1 in the tumor and thus inhibiting growth of the tumor. Said method may result in at least one of (1) a decrease in cancer cell proliferation, apoptosis, $G_2$/M arrest, mitotic catastrophe; (2) a decrease in at least one of mRNA stability and mRNA translation for at least one protein selected from the group consisting of c-Myc, KRAS and combinations thereof; and (3) an increase in miRNA expression, such as pri-let-7a miRNA expression.

Delivery of the agents of the presently disclosed and claimed inventive concept(s) (e.g., specific DCLK1 binding agents and/or siRNAs) into a patient can either be direct, i.e., the patient is directly exposed to an agent of the inventive concept(s) or agent-carrying vector, or indirect, i.e., cells are first transformed with the nucleic acid sequences encoding an agent of the inventive concept(s) in vitro, then transplanted into the patient for cell replacement therapy. These two approaches are known as in vivo and ex vivo therapy, respectively.

The presently disclosed and claimed inventive concept(s) is also directed to a method of generating a tumor cell. Such method includes providing at least one of a primary cell and an immortalized cell, and introducing a gene encoding DCLK1 into the cell such that the cell overexpresses the DCLK1 protein and exhibits increased cell proliferation and induction of anchorage independent growth. Such generated tumor cell may then be utilized as a model system for identifying novel therapeutics for cancer therapy.

The presently disclosed and claimed inventive concept(s) is also directed to a diagnostic method for cancer detection, progression and/or prognosis. Such diagnostic method involves the detection of DCLK1 protein as a marker. The method may also include detection of the specific level of DCLK1 protein present and comparison thereof to known levels of DCLK1 protein present in normal cells and in cells at various stages of tumor progression and/or metastasis.

The presently disclosed and claimed inventive concept(s) is also related to a method for the detection of at least one cancer cell to aid in the diagnosis of neoplastic diseases, such as but not limited to, cancers of the gastrointestinal tract, colon, pancreas, breast, prostate, lung and ovaries. The method includes the steps of providing a biological sample from a patient, providing a specific DCLK1 binding agent composition, contacting the biological sample with the composition under conditions appropriate for formation of a complex between the composition and DCLK1 protein present on a surface of at least one cancer cell, detecting the presence of any complex formed, and determining that at least one cancer cell is present in the biological sample if complex is detected. The method may further include measuring the amount of complex formed, and correlating the amount of complex formed to the diagnosis of neoplastic disease.

The above-described method could also be utilized to determine the effect of chemopreventive strategies on the development of early neoplastic lesions.

The presently disclosed and claimed inventive concept(s) also relates to a method of treating a neoplastic disease by targeting an anticancer agent, such as but not limited to a cytotoxic agent, to a gastrointestinal and/or pancreatic stem cell in a patient with a gastrointestinal and/or pancreatic tumor. The method includes providing a conjugate of the anticancer agent attached to a specific binding agent for DCLK1 protein, and administering an effective amount of such conjugate to the patient, thereby inhibiting growth of the tumor. The anticancer agent may be a chemotherapeutic agent. In addition, the conjugate could also be attached to an implantable biodegradable agent.

The above-described method of treating a neoplastic disease could also be utilized to prevent neoplastic diseases, by administering the conjugate (or any of the other compositions disclosed herein) to a patient not experiencing a cancer. Depletion of gastrointestinal and/or pancreatic stem cells in the patient will act to deplete the potential for neoplasia and tumor formation.

In one particular embodiment, the presently disclosed and claimed inventive concept(s) is directed to an antibody-drug conjugate targeting extracellular DCLK1. The antibody-drug conjugate may be formed by any method known in the art or otherwise contemplated herein. In addition, the antibody and drug may be directly attached to one another to form the conjugate, or the antibody and drug may be indirectly attached to one another by any conjugation method known in the art or otherwise contemplated herein. In a particular embodiment, the antibody-drug conjugate includes: (a) at least one general cytotoxic agent; (b) at least one bifunctional or multifunctional linking molecule and/or peptide that is bound to the cytotoxic agent(s); and (c) at least one antibody and/or peptide targeting extracellular DCLK1 protein that is bound to the cytotoxin-modified linking molecule and/or peptide.

Any cytotoxic agent useful in therapy of a cancerous patient may be utilized in antibody-drug conjugates disclosed and claimed herein. Non-limiting examples of cytotoxic agents that may be utilized include Paclitaxel, Cisplatin, Mercaptopurine, Vinblastine, Etopside, Doxorubicin, 5-Fluorouracil, Capecitabine, and combinations and derivatives thereof. Non-limiting examples of linking molecules that may be utilized include N-(para-maleimidophenyl)isocyanate (PMPI), Succinimidyl-4-(N-maleimidomethyl)cyclohexane-1-carboxylate (SMCC), Sulfosuccinimidyl-4-(N-maleimidomethyl)cyclohexane-1-carboxylate (Sulfo-SMCC), 1-Ethyl-3-(3-dimethylaminopropyl)carbodiimide hydrochloride (EDC), varying lengths of polyethylene glycol spacers ($PEG_n$), and combinations and derivatives thereof.

The methods of using the antibody-drug conjugate to target DCLK1-expressing cancer cells for destruction provides multiple benefits. One benefit of this method is that targeting DCLK1$^+$ cells leads to the destruction of cancer stem cells (CSCs) and progenitors, thus resulting in reduction and/or ablation of tumors, blockage of epithelial-mesenchymal transition, and/or the prevention of relapse and metastasis. DCLK1 is expressed in circulating tumor cells (CTCs); therefore, this method will capture and destroy metastatic cells in circulation bound for attachment to sites away from the primary tumor. Additionally, DCLK1 is overexpressed or mutated in many cancers, and therefore this method leads to the destruction of cancerous cells in general, regardless of their CSC or CTC characteristics. Another benefit of the administration of the antibody-drug conjugate is that targeting DCLK1-expressing cells specifically for chemotherapy results in reduced side effects compared to therapy with the cytotoxic compound alone.

The presently disclosed and claimed inventive concept(s) also relates to a method for diagnosing at least one of (1) the severity of a gut and/or pancreatic injury following exposure to a DNA damaging agent, and (2) the severity of colitis (colonic ulceration and inflammation). The method includes the steps of providing a biological sample from a patient, identifying stem cells present in the biological sample using a specific binding agent that recognizes DCLK1 protein, and measuring an effect on at least one of stem cell apoptosis, senescence, proliferation and cell division of the DCLK1 positive cells when compared to DCLK1 positive cells not exposed to the conditions listed under (1) or (2). This technique could also be used to measure the response to anti-inflammatory therapies for IBD and other non-specific collitidies.

While the above-described methods have been disclosed as useful with gastrointestinal (GI) and pancreatic tumors, such methods are not specifically limited to use with GI and pancreatic tumors. For example, targeted depletion of a cancer or adenoma-initiating stem cell, as described herein, would also be useful with solid tumors of both GI and non-GI origin (such as but not limited to, lung cancer).

The presently disclosed and claimed inventive concept(s) is also related to methods of isolating GI and/or pancreatic stem cells in non-cancerous patients. The method includes the steps of providing a biological sample of gastrointestinal and/or pancreatic tissue from a patient and providing the composition comprising an agent that specifically binds to DCLK1 as described herein above. The biological sample is then contacted with the composition under conditions appropriate for formation of a complex between the composition and DCLK1 present on a surface of at least one cancer cell. Cells having the composition attached thereto are then isolated, followed by separating the composition from the cells. The isolated GI and/or pancreatic stem cells could be used for sorting experiments, and these multipotent cells could be cultured and their differentiation directed into other gut and/or pancreatic cell types. Optionally, the GI and/or pancreatic stem cells can be cultured and used to re-populate damaged intestinal and/or pancreatic epithelial cells exposed to severe injury.

EXAMPLES

Examples are provided herein below. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

Example 1

Colorectal cancer is a major cause of cancer death in the western world. Mutational activation of oncogenes joins with inactivation of tumor suppressor genes to produce colorectal tumors (Clark, 2006). The transformation of normal mucosal epithelial cells into invasive colorectal carcinoma occurs via a synchronized accumulation of mutations in a series of critical genes (Fearon, 1990). The long time span between initiation and gross development of tumors presents an enormous challenge in dissecting the critical molecular mechanisms that regulate neoplastic change.

Defining the mechanisms that regulate stem cell fate is critical in increasing our understanding of the neoplastic process. Tumorigenesis in the gut is thought to arise specifically in the stem cell (Sansom et al., 2005; de Lau et al., 2007) population located at or near the base of the intestinal and colonic crypts. Transit cell populations originating from the stem cell zone become fully differentiated and are eventually sloughed into the lumen. Transit cells' short life span, whether they are mutated or not, limits their deleterious influence in the intestinal or colonic crypt (Potten, 2003). Because no specific gut stem cell markers have been identified definitively (Bjerknes et al., 2005; Kayahara et al., 2003), recognizing and assaying resident intestinal stem cells is quite difficult and has raised contentious argument; however, the microcolony assay following γ-irradiation (IR) is by definition a functional evaluation of intestinal stem cell fate (Withers et al., 1970) and can potentially provide a mechanism for examining the early events of tumorigenesis. Because homeostatic mechanisms of stem cell proliferation are the same processes that become dysregulated in carcinogenesis (Sancho et al., 2003), a complete examination of these proliferation mechanisms holds medical significance in targeting future cancer treatments; therefore, a more detailed understanding of the pathways that regulate stem cell behavior is essential.

In working toward a complete understanding of these pathways that regulate stem cell behavior, one major obstacle in the study of gastrointestinal stem cell biology has been the lack of definitive markers to identify gastrointestinal stem cells. The presently disclosed and claimed inventive concept(s) confirms that DCLK1, a microtubule-associated kinase expressed in post-mitotic neurons (Lin et al., 2000), is an intestinal stem cell marker. This discovery allows one to assay resident intestinal stem cells and their response to genotoxic injury. DCLK1 was identified as a Gene Ontogeny-enriched (or GO-enriched) transcript expressed in comparison with GEP (gastric epithelial progenitor) and whole stomach libraries (Giannakis et al., 2006). Immunohistochemical analysis using antibodies directed at DCLK1 revealed single cell staining in scattered intestinal crypt cross-sections at or near position 4 and in gastric isthmus cells in the putative stem cell location. The radiation-injury model was chosen to investigate its effects on stem cell fate for several reasons: (1) the kinetics of radiation injury has been extensively characterized in the small intestine in mice (Potten, 1990; Wright, 2000); (2) radiation injury can be induced uniformly throughout the gut at discreet points in time; and (3) the extent of radiation injury on crypt clonogenic survival can be varied with the dose of radiation. In this Example, immunohistochemical analysis was employed in order to visualize crypt epithelial stem cells and to determine the cell specific DCLK1 expression at baseline and in response to radiation injury in adult mice.

Materials and Methods for Example 1

Immunohistochemistry: (a) Brightfield: Heat Induced Epitope Retrieval (HIER) was performed on 4 mm paraffin-embedded mouse small intestine and colon sections utilizing a pressurized de-cloaking chamber (Biocare Medical Inc., Concord, Calif.) and incubated in citrate buffer (pH 6.0) at 99° C. for 18 minutes. The sections were then washed three times with PBS (Sigma-Aldrich, St. Louis, Mo.), and endogenous biotin activity was blocked using Avidin/Biotin blocking kit (Vector Laboratories, Inc., Burlingame, Calif.) and/or with DCLK1 blocking peptide (Abgent, San Diego, Calif.) wherever indicated according to manufacturer's instructions. Further, endogenous peroxidase activity was quenched with 3% hydrogen peroxide. After washing, the slides were then incubated in horse normal serum (2%) and BSA (1%) at room temperature for 20 minutes to block non-specific binding. The sections were then exposed to primary antibodies rabbit anti-DCLK1 (Abgent, San Diego, Calif.), rabbit anti-Musashi-1 (Abcam Inc., Cambridge, Mass.), rabbit PCNA (proliferating cell nuclear antigen) (Santa Cruz Biotechnology Inc., Santa Cruz, Calif.), goat β-catenin (Santa Cruz Biotechnology, Inc.), rabbit anti phospho H2AX (Cell Signaling Technology, Inc., Danvers, Mass.) overnight at refrigerator temperature. Slides were then washed three times with PBS and incubated in the appropriate secondary antibody biotinylated donkey anti-rabbit, donkey anti-goat (Jackson Immuno Research Laboratories, Inc., West Grove, Pa.) 30 minutes at room temperature. Slides were washed again and then incubated in SA-HRP (Dako, Carpinteria, Calif.) at room temperature for 12 minutes. After final wash in PBS, chromogenic development was performed utilizing DAB (brown) and/or AEC (red) substrate (Sigma-Aldrich, St. Louis, Mo.). All slides were counterstained with hematoxylin (Biocare Medical Inc., Concord, Calif.), dehydrated in graded alcohols, cleared in xylene, and permanently mounted with cryoseal (Richard-Allen Scientific, Kalamazoo, Mich.).

(b) Fluorescence: HIER was performed on 4 mm paraffin-embedded tissue sections utilizing a pressurized de-cloaking chamber (Biocare Medical Inc., Concord, Calif.) and incubated in citrate buffer (pH 6.0) at 99° C. for 18 minutes. After washing three times with PBS, the slides were then incubated in horse normal serum (2%) and BSA (1%) at room temperature for 20 minutes to block nonspecific binding. Sections were then sequentially exposed to rabbit anti-DCLK1 (Abgent, San Diego, Calif.) for 1 hour at 30° C. and its appropriate secondary Cy3 conjugated donkey anti-rabbit (Jackson Immuno Research Laboratories, Inc., West Grove, Pa.) for 30 minutes at room temperature. Finally fluorescein conjugated TUNEL staining was performed using "In situ Cell Death Kit" (Roche Diagnostics Corp., Indianapolis, Ind.), according to manufactures instructions. The slides were then wet-mounted and counterstained utilizing VECTASHIELD® with DAPI (Vector Laboratories, Inc., Burlingame, Calif.). For co-staining of DCLK1 with Musashi-1, the slides were incubated with normal goat serum after decloaking and exposed to rabbit anti-DCLK1 (Abgent, San Diego, Calif.) for 1 hour at 30° C. and its appropriate secondary goat anti-rabbit ALEXA FLUOR® 568 (Life Technologies Corp., Grand Island, N.Y.) for 30 minutes at room temperature. Further, the slides were blocked with normal goat and normal donkey serum and exposed to rabbit anti-Musashi-1 (Abcam Inc., Cambridge, Mass.) for 1 hour at 30° C. and its appropriate secondary donkey anti-rabbit ALEXA FLUOR® 488 (Life Technologies Corp., Grand Island, N.Y.) for 30 minutes at room temperature. Then the slides are washed with Hoechst 33342 for staining of the nucleus.

(c) Microscopic Examination: Slides were examined using Nikon 80i microscope base. For brightfield, 60× digital images were taken with PIanAPO objective and DXM1200C camera (Nikon Inc., Melville, N.Y.). Fluorescent images were taken with 60× PlanFluoro objective and 2× optical converter for a final magnification of 120×, utilizing CoolSNAP™ ES2 camera (Photometrics, Tucson, Ariz.). Filter sets were used employing excitation ranges for Cy3, FITC, and DAPI. All images were captured utilizing NIS-Elements software (Nikon) and further processed using Adobe Photoshop 8.0 software.

Results for Example 1

Localization of DCLK1, a putative intestinal stem cell marker. In wild-type (WT) adult mouse intestine (FIG. 1A), it was confirmed that immunoreactive DCLK1 is expressed primarily in single cells in the putative stem cell zone in adult conventionally housed C57 Bl/6 mice. In rare sections villus staining was observed, particularly at the crypt villus junction (data not shown). Distinct cytoplasmic staining was observed at baseline while DCLK1 expression was a rare event. Staining was present in approximately one in six intestinal crypt cross-sections on average. Immunostaining of the proposed columnar longitudinal epithelial cell interspersed between paneth cells is also observed. These columnar longitudinal epithelial cells have been previously shown to the putative stem cell marker musashi-1 (MSI-1) (Kayahara et al., 2003; Potten et al., 2003). Preincubation with DCLK1 blocking peptide (Abcam Inc., Cambridge, Mass.) completely abolished DCLK1 immunoreactivity (FIG. 1B).

Figure 2:
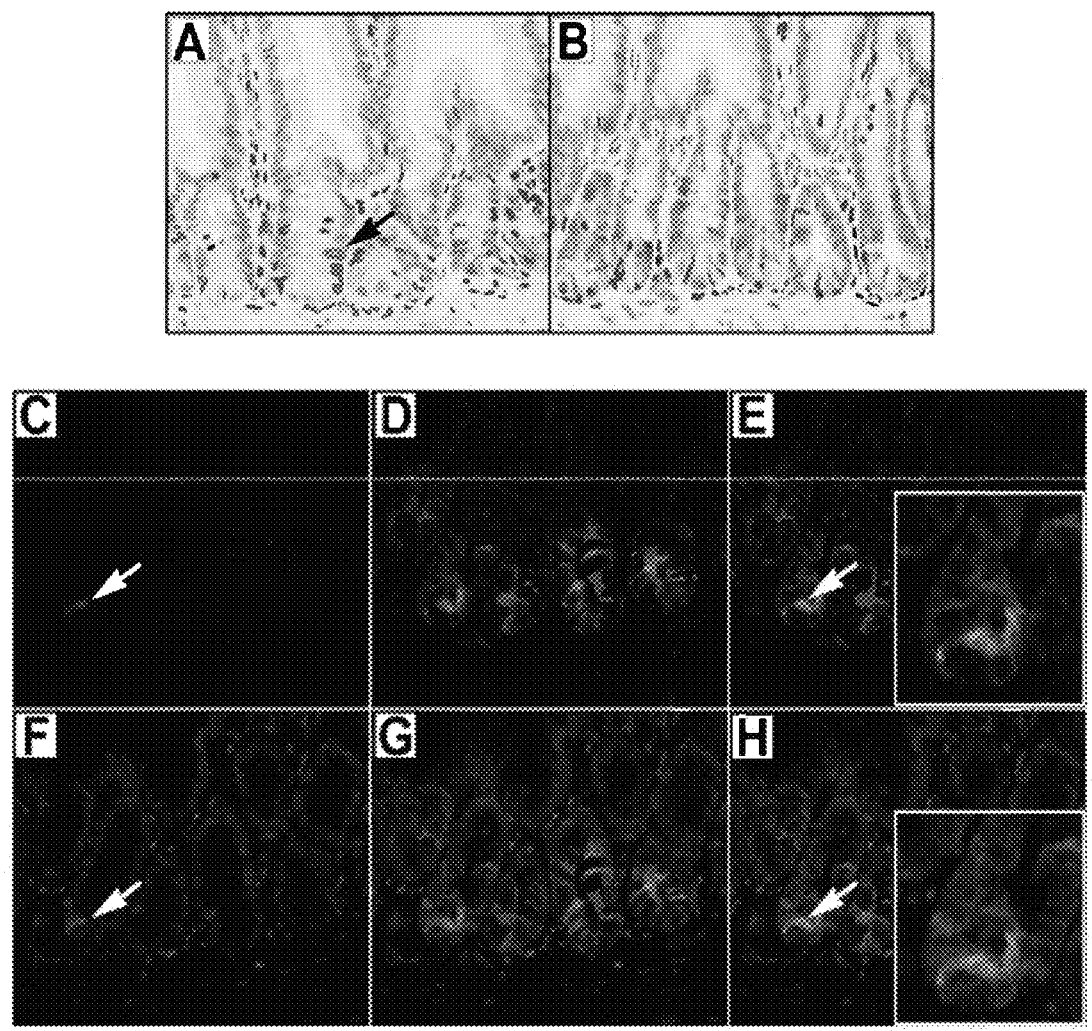

Colocalization of DCLK1 and MSI-1. In order to determine whether DCLK1 was expressed in the same cells that expressed the putative stem cell marker MSI-1, immunostaining for MSI-1 was performed using the intestines of adult WT uninjured mice. In FIG. 2A, distinct DCLK1 staining was once again observed in the crypt. In FIG. 2B crypt epithelial staining for MSI-1 was observed in several cells at the base of the crypt including cell position 4 just above the paneth cell zone, consistent with its reported stem cell localization. Furthermore immunofluorescence microscopy and double immunostaining were used for DCLK1 and MSI-1. Single cell staining for DCLK1 was again observed in the stem cell zone (FIG. 2C). MSI-1 staining was also observed in the crypts (FIG. 2D). Distinct colocalization was observed however (FIG. 2H) with DCLK1 and MSI-1 (orange). These data demonstrate that DCLK1 is expressed in the same cell as MSI-1, but likely represents a subset of MSI-1 expressing cells. Nuclei stained with Hoechst 33342 (blue) are demonstrated in FIGS. 2F-G.

Figure 3:
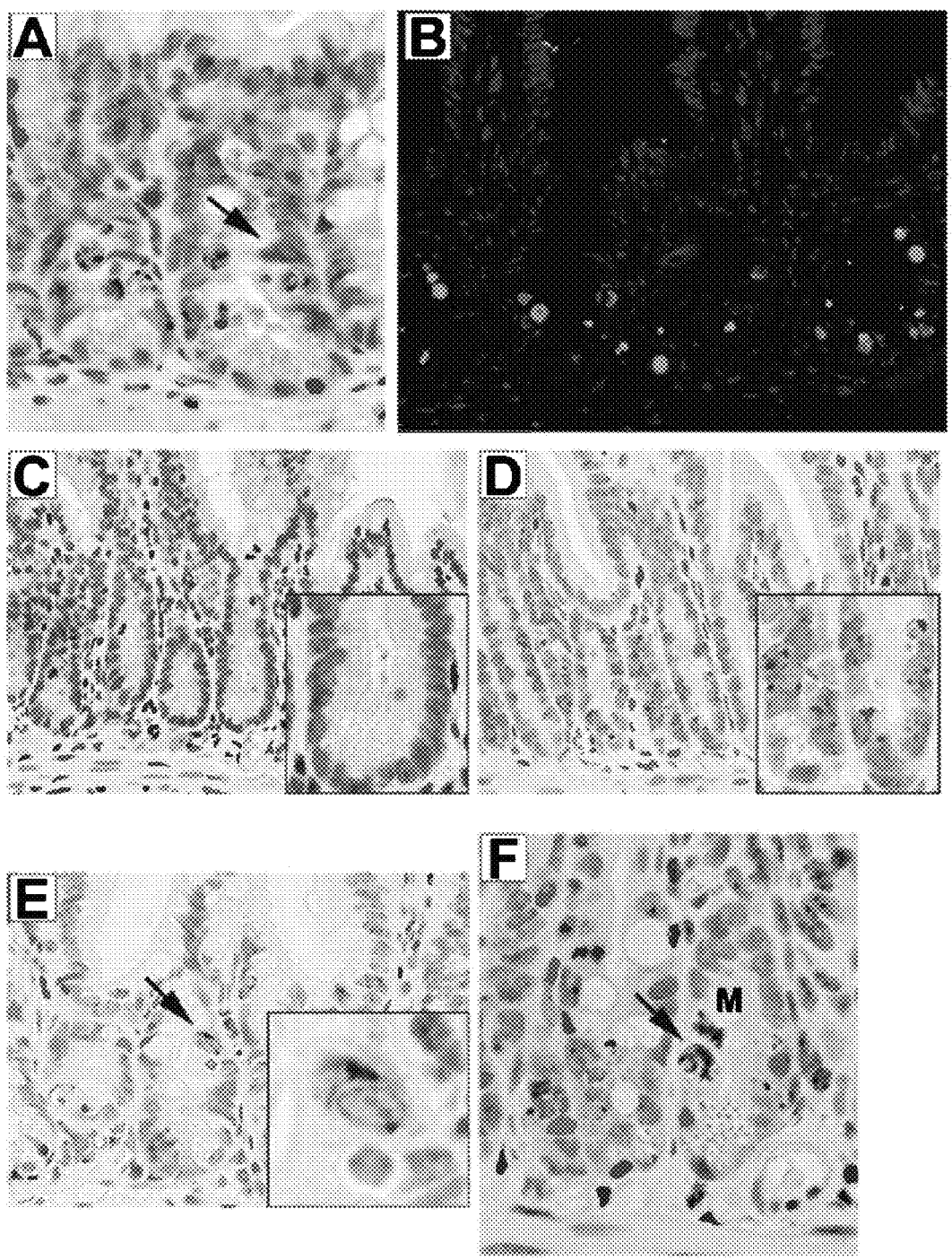

Fate of DCLK1 positive cell in response to radiation injury. To investigate whether DCLK1 expression was upregulated following ionizing radiation (IR), adult mice were treated with whole body 6 Gy IR, at doses sufficient to induce epithelial apoptosis in the stem cell zone (Houchen, et al, 2000; Merritt et al., 1994; Radtke et al., 2005). Initially, the 6 hour after 6 Gy IR time point was chosen, as this is the time when maximal p53 dependent apoptosis is observed in the intestinal crypt (Merritt et al., 1994). Here DCLK1 staining similar to that observed at baseline was demonstrated (FIG. 3A). Following 6 Gy IR, morphologically appearing apoptotic cells were observed in the lower third of the intestinal crypt with a typical distribution following IR (FIG. 3A arrows). Surprisingly, apoptosis was not observed in DCLK1 positive cells within the crypt in over 100 counted crypt cross-sections. In order to confirm this finding, a similar experiment was performed and stained for DCLK1 and TUNEL (a marker for apoptosis). Apoptotic cells within the crypt were identified by TUNEL staining (green), and DCLK1 staining (red) at single cell positions in the intestinal crypt was again observed (FIG. 3B). There was no evidence of apoptosis in DCLK1 expressing cells. Furthermore, radiation-induced DNA damage was observed in the crypt at 6 hours following IR evidenced by the presence of phospho-H2AX positive cells (FIG. 3D, magnified in inset), which was not observed in unirradiated mice (FIG. 3C, magnified in the inset). The DCLK1 positive cell was also positive for nuclear phospho-H2AX, but did not undergo apoptosis at that time (FIG. 3E, magnified in the inset). Indeed, this was not completely unexpected as earlier reports suggest that two important waves of apoptosis exist following IR. The first wave occurs at 4.5-6 hours (p53 dependent), and the second is near 24 hours (p53 independent). The second wave of apoptosis is thought to affect stem cells primarily (Merritt et al., 1994; Radtke et al., 2005). In order to investigate this further, animals were examined 24 hours after IR, and immunohistochemical analysis for DCLK1 was performed (FIG. 3F). In this figure morphological evidence of apoptosis and immunoreactive DCLK1 staining in the stem cell zone are demonstrated; however, at this time point, there was clear evidence of apoptosis in the DCLK1 positive cell (arrow). Additionally, the appearance of mitotic figures was noted, demonstrating the release of these cells from radiation-induced cell cycle arrest (FIG. 3F denoted as 'M'). The mitotic figures were often DCLK1 immunoreactive, but this staining pattern was not observed in all of the mitotic figures present throughout the intestine. It should be noted that many of the cells with morphologic features consistent with mitosis were on occasion immediately adjacent to cells in the process of apoptosis, and these exhibited striking expression of DCLK1. Consequently, these data suggest that by 24 hours after low dose IR (6 Gy), a few (one per cross section) stem cell/progenitor cells are removed by apoptosis and the potential descendants of these cells are able to divide and, at least transiently, express DCLK1.

Figure 4:
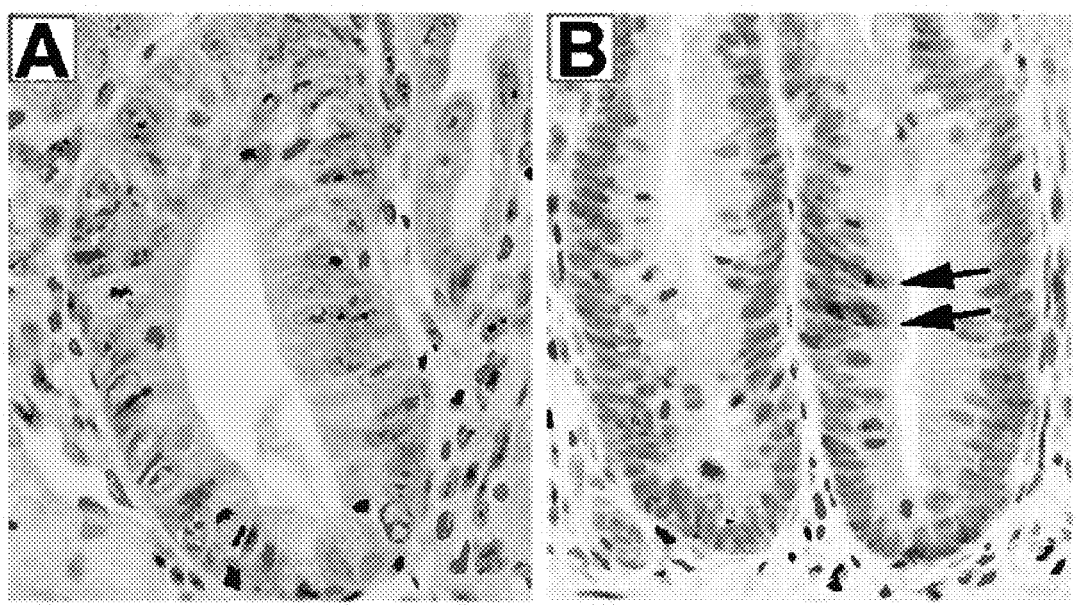

Expression pattern of DCLK1 in regenerative crypts. To determine whether or not DCLK1 is expressed in regenerative crypts following radiation injury, adult mice were exposed to lethal dose (12 Gy) γ-irradiation, and DCLK1 expression was examined in regenerative crypt epithelial cells. 12 Gy was chosen as this dose has been demonstrated to induce crypt stem cell sterilization in a majority of intestinal crypts (Potten et al., 1994). Regenerative crypts appear 3.5 days following radiation injury and represent the survival of at least one progenitor/stem cell per crypt. DCLK1 staining was not observed in regenerative crypts following 12 Gy (FIG. 4A). These data demonstrate that DCLK1 is not expressed at the protein level during the period of crypt regeneration when proliferation is at its peak. This data is consistent with the original report (Giannakis et al., 2006) and with our findings, failing to demonstrate DCLK1 staining in BrdUrd positive cells (data not shown). On the other hand, it is unclear why this marker is not expressed as every cell in the regenerative crypt is not in a proliferative state. This may represent some form of loss of niche signaling in 3.5 day post-irradiated crypts lacking an intact crypt/villus axis or functional mesenchymal cells. Although it is interesting to speculate, more studies directed towards defining the regulatory mechanisms that control expression of DCLK1 are required. Restoration of DCLK1 expression however, within the crypts was observed 7 days post-irradiation when the morphologic features of the crypts/villus axis are returning to baseline (FIG. 4B), yet the crypts appear elongated with heaping up of nuclei. In several cross-sections DCAMKL– positive cells were not necessarily restricted to lower crypt region.

Figure 5:
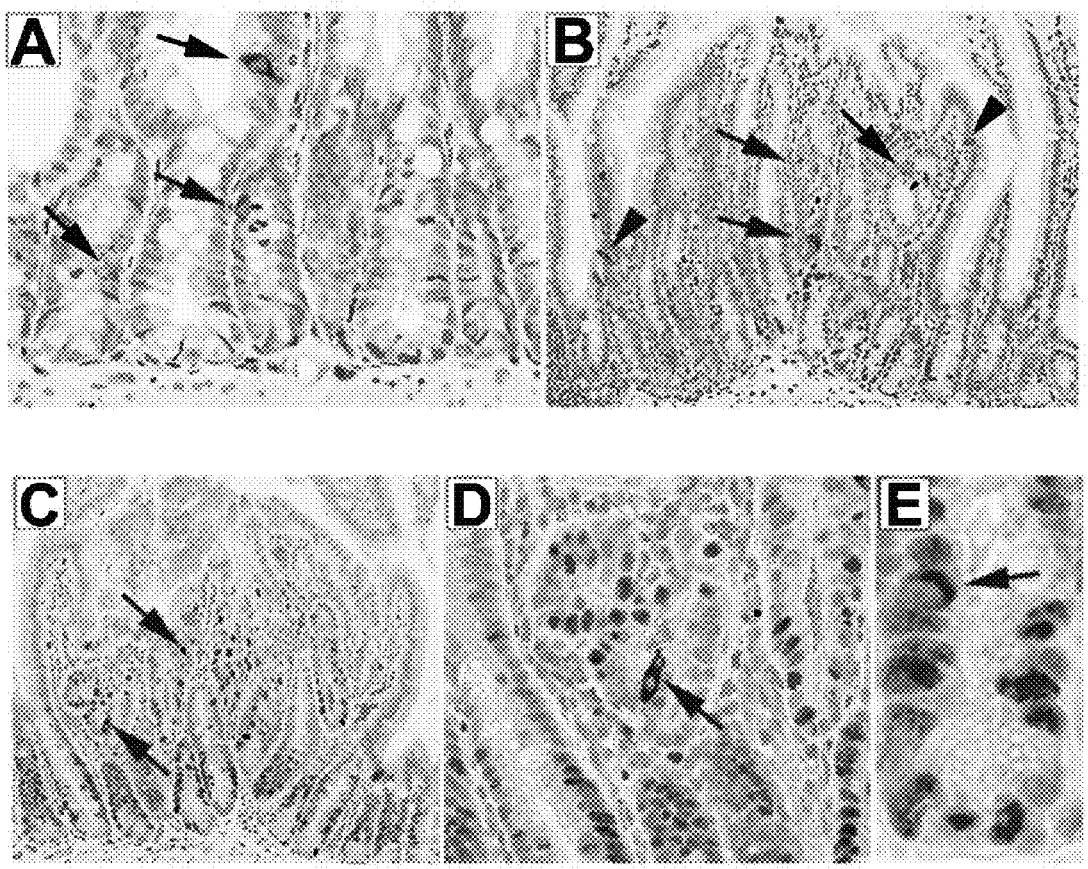

DCLK1 as a putative adenoma stem cell marker. To determine whether DCLK1 could be used to label putative stem cells within tumors, immunohistochemical analysis was employed to identify DCLK1 in the intestines of APC/min mice. These mice have a germline mutation in the APC gene and develop numerous intestinal polyps (Clevers, 2004; Corpet et al., 2005). APC mutations are one of the earliest genetic alterations in epithelial tumor progression (Clevers, 2006). Indeed, greater than 60 percent of human colorectal adenomas exhibit a mutation in APC (Powell et al., 1992). In WT mice classical single cell staining was observed in scattered crypt epithelial cells. However, in APC/min mice, a slightly different expression pattern was observed compared to WT. Although occasional single cell staining in the crypts was observed as before, there was a trend towards increased DCLK1 expression on the villi (FIGS. 5A and 5B) compared to WT mice. This was often particularly evident in villus epithelial tissues adjacent to or surrounding adenomas (FIG. 5B). Note the distinct cytoplasmic staining pattern in the villus epithelium (FIG. 5A arrow head). It is unclear whether this is a function of villus expression of stem cells or a loss of crypt niche restriction in DCLK1 expressing cells. It should be noted that villus epithelial DCLK1 expression was occasionally observed in WT mice as well. Further studies following isolation of these cells are required to fully determine the functional significance of these villus DCLK1 staining cells.

DCLK1 positive cells in adenomas are quiescent. The potential stem cell origin of neoplastic tissues has become increasingly recognized (deLau et al., 2007; Radtke et al., 2005). Accordingly, changes in the regulation of stem cells could potentially alter the risk of tumorigenesis. Immunohistochemical analysis was used to assess DCLK1 expression patterns in APC/min adenomas. Distinct staining was observed (FIG. 5B), in a minority of cells within the adenoma. Given the limited expression pattern of DCLK1 in adenomas, the inventors wanted to determine whether DCLK1 was expressed in proliferative cells within adenomas. Double staining protocols for both DCLK1 and PCNA (proliferating cell nuclear antigen) were employed in APC/min mice. As expected the majority of the adenomas expressed the proliferation marker PCNA. Indeed, there were very few cells within the adenoma that did not express PCNA. As PCNA staining is primarily nuclear, it was predicted that the cytoplasmic DCLK1 would be identified in proliferating cells if co-staining was present. DCLK1 was expressed in cells within the adenoma that were not proliferating and therefore quiescent (FIG. 5C, magnified in FIG. 5D). This was confirmed in normal crypt epithelial cells in which DCLK1 positive cells were negative for PCNA (FIG. 5E). This is consistent with the original report in FVB/n mice where DCLK1 cells were negative for BrdUrd (Giannakis et al., 2006); however, this finding within adenomas has not been previously described.

Figure 6:
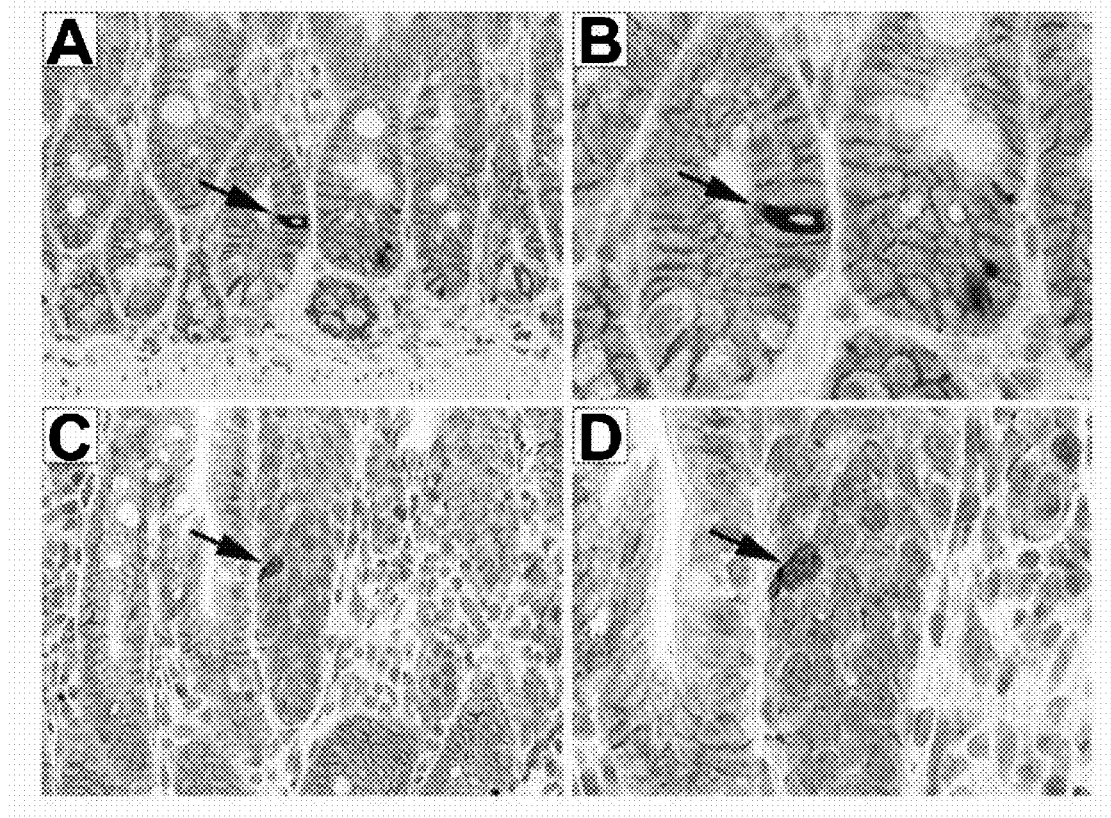

Co-expression of β-catenin and DCLK1 in APC/min tumors. To determine whether nuclear localization of β-catenin could be observed in DCLK1 expressing cells, the identification of β-catenin in quiescent cells within adenomas was sought. β-catenin translocation to the nucleus is one of the earliest steps in neoplastic transformation and is readily observed in adenomas of APC/min mice. In FIG. 6, β-catenin and DCLK1 coimmunostaining is demonstrated in normal appearing intestinal crypts in APC/min mice and within a crypt adenoma. In normal appearing crypts, DCLK1 immunoreactive cells exhibit typical membrane β-catenin staining, without any evidence of nuclear translocation (FIG. 6A, magnified in FIG. 6B); however, within the adenoma, nuclear β-catenin is readily identified in the DCLK1 expressing cell (FIG. 6C arrow, magnified in FIG. 6D). These data taken together strongly suggest that the normal epithelial intestinal stem cell and the adenoma stem cell can be distinguished based on nuclear β-catenin and DCLK1 immunostaining. Furthermore, the adenoma stem cell can be distinguished from the proliferative adenoma cells based on PCNA and DCLK1 immunostaining.

Figure 7:
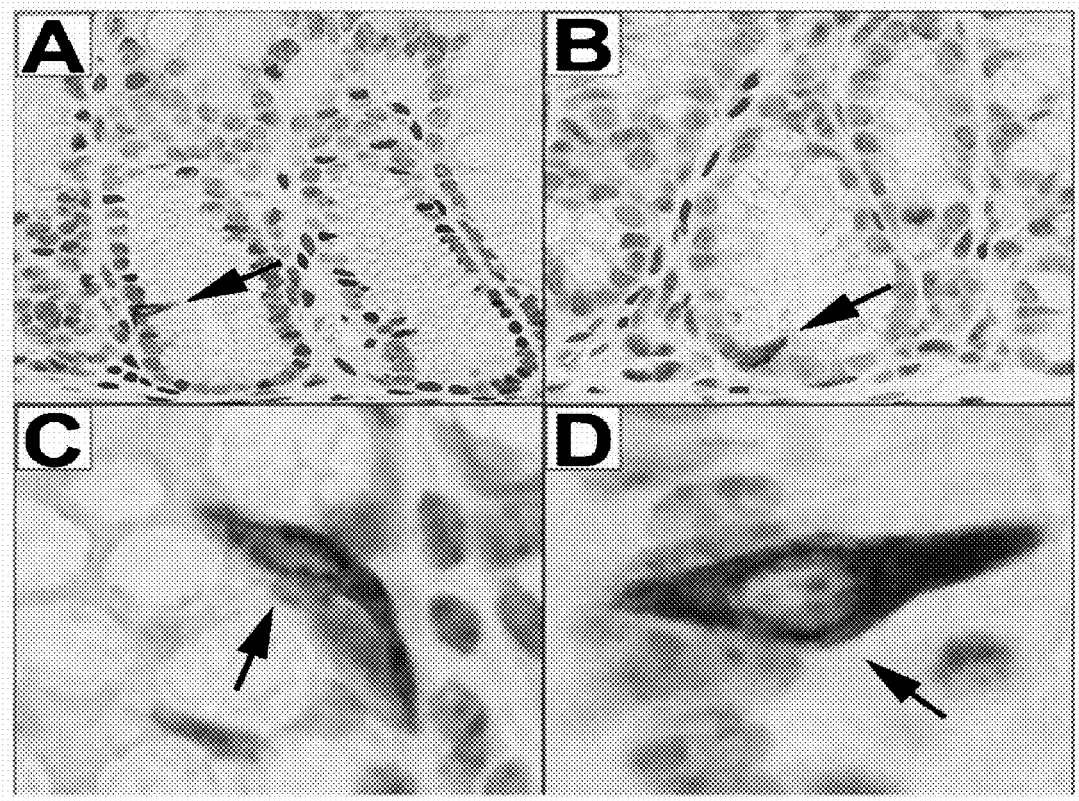

Morphology of DCLK1 expressing cells. Upon closer observation the unique morphologic appearance of the DCLK1 expressing cell resembles that of neural processes observed on gastric D cells (Radford et al., 2006) (FIGS. 7A-D). In FIG. 7A, DCLK1 expression was observed in cells in the mid crypt in the proximal colon. In FIG. 7B, an expression was observed at the crypt base in the distal colon. Additionally, higher power views in both colon (FIG. 7C) and distal jejunum (FIG. 7D) clearly illustrate the unique morphologic staining pattern resembling axonal like processes.

Discussion of Example 1

Figure 1:
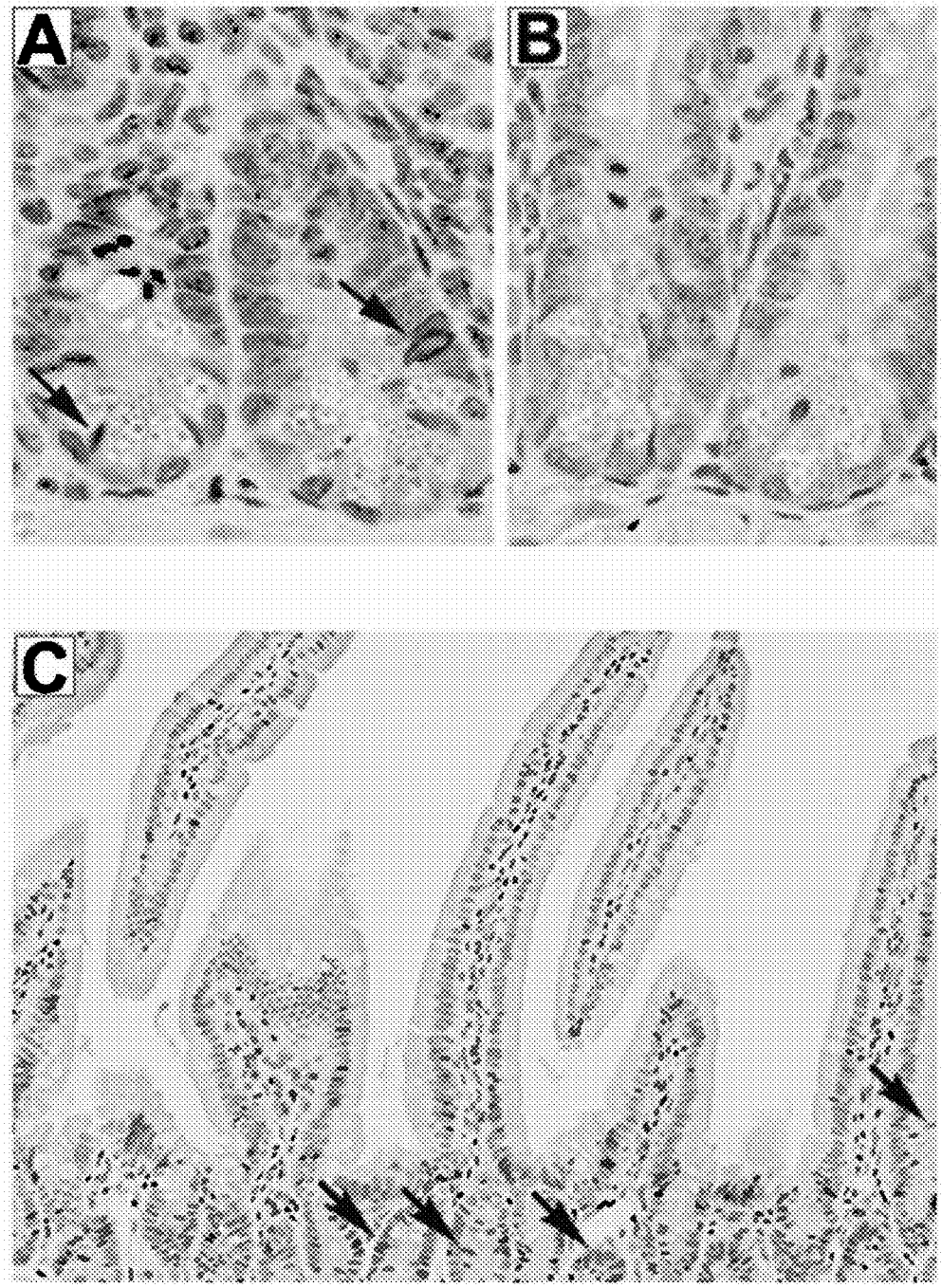

Typically, one crypt with definitive DCLK1 staining was observed per 6 crypts in a typical intestinal cross-section near cell position of 4 in the crypt. Presumably, this is due to the 3-dimensional nature of the crypt and the low probability that every cross-section will contain a stem cell. Nevertheless, DCLK1 immunoreactivity was consistently observed in the stem cell zone as previously noted (FIG. 1). The response to acute radiation injury is the most extensively characterized model system for studying injury repair in the rodent gastrointestinal tract. The actively proliferating cell population in the intestinal crypt rapidly undergoes apoptotic cell death following sublethal doses of IR, (<8 Gy) (Ishizuka et al., 2003). Because epithelial cells at the lower one third of the small intestinal crypts are the first to undergo apoptosis following low-dose IR (1 Gy), it is postulated that these "true" or "ultimate" stem cells prefer to undergo apoptosis rather than repair even comparatively minor damage to their DNA (Potten et al., 2002). This trait may serve to reduce the risk of propagating a mutated clone within the crypt. If all the so-called "ultimate stem cells" (Potten et al., 2002) are destroyed, then their more radio-resistant daughter cells will assume stem cell functions and maintain the crypt; however, the molecular mechanisms that regulate this transfer of clonogenic capacity are poorly understood. In this Example, it has been demonstrated that cells positive for DCLK1 underwent DNA damage along with other cells in the crypt, but did not undergo apoptosis. Whereas 24 hours following IR, the putative stem cell or cells positive for DCLK1 did undergo apoptosis. Following 12 Gy IR, the DCLK1 reactivity is lost in the regenerative crypts 3.5 days following IR. DCLK1 expression was restored at day 7 post-irradiation when the morphologic features of the crypts/villus axis are returning to baseline. These data support the hypothesis that daughter cells are capable of taking on stem cell characteristics in response to radiation-induced deletion of the "ultimate stem cell" and also illustrates that this process occurs at some time beyond 6 hours and prior to 24 hours after low dose radiation injury. These data may potentially explain why doses of IR<8 Gy do not result in crypt sterilization of stem cells and, as a result, have little effect on clonogenic survival (Houchen et al., 2000).

This Example reports the identification of a novel intestinal stem cell marker that can be employed to test the effects of DNA damaging agents, chemotherapeutic agents and radiation injury on stem cell deletion both directly and in real time. The data presented here also support assessment of radiation-induced apoptosis of intestinal stem cells 24 hours after IR as opposed to 6 hours in intestinal cross sections. The demonstration of a more variable expression pattern of DCLK1 in the normal epithelium of APC/min mice compared to WT mice suggests that APC/min mice may exhibit different mechanisms of stem cell niche regulation, particularly in the regions adjacent to adenoma. The small percentage of quiescent DCLK1 expressing cells within a particular adenoma suggests that they may be the origin of the more proliferative neoplastic cells, but it remains unclear whether these cells by themselves have tumorigenic potential either outside of the adenoma or outside of the crypt niche (villi). In the normal appearing crypts of APC/min mice, β-catenin was co-expressed in the cytoplasm along with DCLK1, whereas in adenomas, DCLK1 positive cells demonstrated nuclear localization of β-catenin. This finding potentially illustrates a fundamental difference between the normal and adenoma stem cell. Isolating these cells and injecting them into nude mice xenograft models are essential in addressing the tumorigenic potential of these cells.

Example 2

Pancreatic adenocarcinoma has the worst prognosis of any major malignancy with a 3% 5-year survival (Hoyer et al., 2006). Major obstacles in treating pancreatic cancer include extensive local tumor invasion and early metastasis. There is increasing evidence that a small subset of cells termed "cancer stem cells" (CSCs) are capable of initiating and sustaining tumor growth in transplantation assays (Diehn et al., 2006). CSCs share unique properties with normal adult stem cells, including the ability to self-renew and differentiate. CSCs are often refractory to current standard chemotherapeutic agents and radiation therapies, as they are designed to eradicate actively cycling cells, not slowly cycling cancer stem cells. Thus, novel therapies that specifically target the cancer stem cell population, either alone or in conjunction with current strategies may be more effective in obliterating solid tumors.

The existence of CSCs was first demonstrated in acute myelogenous leukemia (Bonnet et al., 1997) and subsequently verified in breast (Al-Hajj et al., 2003), pancreatic (Li et al., 2007) and brain tumors (Singh et al., 2004; Singh et al., 2003; Singh et al., 2004A). The CD133$^+$ subpopulations from brain tumors could initiate clonally derived neurospheres in vitro showing self-renewal, differentiation, and proliferative characteristics similar to normal brain stem cells (Singh et al., 2004; Singh et al., 2003; Singh et al., 2004A). Furthermore, transplantation of CD133$^+$ but not CD133$^-$ cells into NOD/SCID mice was sufficient to induce tumor growth in vivo. In a recent study, primary human pancreatic adenocarcinomas were implanted in immuno-compromised mice to assess the ability of specific cell surface markers to identify a subpopulation of pancreatic cancer cells with enhanced tumorigenic potential. A subpopulation of CD44$^+$CD24$^+$ESA$^+$ cells was identified as putative pancreatic cancer stem cells (Li et al., 2007).

Tumor cell heterogeneity present in most solid tumors creates an enormous challenge for cancer eradication. Current strategies for inducing cell death generally target only the most rapidly proliferating cells within a tumor. Indeed radiation therapy specifically targets proliferating cells which are more sensitive to ionizing radiation (Houchen et al., 2000A; Riehl et al., 2000; Tessner et al., 1998; Cohn et al., 1997); however, it is clear that effective tumor-eradication strategies must address the potential survival mechanisms unique to each particular cell type within the malignant population (i.e., quiescent stem cells) (Li et al., 2007). This may explain why standard chemo/radio therapy is effective in causing tumor shrinkage but often fails to prevent tumor recurrence, due to the surviving cancer stem cell's ability to regenerate the tumor even after chemotherapeutic insult.

Characterization of stem cells from the hematopoietic system, neural stem cells from the central nervous system and neural crest stem cells have emphasized the importance of specific cell surface antigens that permit the isolation of stem cells by FACS (Tamaki et al., 2002; Niemeyer et al., 2001). A candidate pancreatic stem cell, characterized by its expression of the neural stem cell marker nestin and lack of established islet and ductal cell markers, has been described (Abraham et al., 2004; Lechner et al., 2002; Zulewski et al., 2001). Furthermore, the basic helix-loop-helix transcription factor neurogenin 3 (NGN3) controls endocrine cell fate specification in uncommitted pancreatic progenitor cells. In the pancreas, $NGN3^+$ cells co-express neither insulin nor glucagon, demonstrating that NGN3 marks early precursors of pancreatic endocrine cells. Moreover, NGN3-deficient mice do not develop islet cells and are diabetic. These data taken together suggest that NGN3 and nestin are critical components of the pancreatic stem/progenitor cell compartment. A convincing recent study demonstrated that the adult mouse pancreas contains islet cell progenitors and that expansion of the β cell mass following pancreatic duct ligation resulted in ductal NGN3 gene expression and the ensuing differentiation of endogenous progenitor cells (Xu et al., 2008). These data suggest that functional islet progenitor cells can be induced in pancreatic ducts following injury.

Example 1 demonstrates that DCLK1, a microtubule-associated kinase expressed in postmitotic neurons, is an intestinal stem cell marker (May et al., 2008). In this Example, it is demonstrated that DCLK1 is also expressed in pancreatic islet epithelial cells with a distribution similar to the putative pancreatic stem cell markers NGN3 and nestin. Furthermore, DCLK1 is expressed in the main pancreatic ductal epithelial cells in rodents, and a subset of cells in human pancreatic tumors. Immunoreactive 14-3-3 σ, which is increased in pancreatic cancer (Guweidhi et al., 2004), has been found in the cytoplasm and rarely in the nucleus of tumor epithelial cells in human pancreatic cancer patients. Moreover, co-expression of DCLK1 and 14-3-3 σ was also observed in tumors. Additionally DCLK1 staining was observed in the surface epithelium of pancreatic intraepithelial neoplasia (PanIN) type lesions (a marker of pancreatic adenocarcinoma) and the intervening stroma in human pancreatic adenocarcinoma, which co-localized with the mesenchymal marker vimentin. In the $Pdx48^{cre}$-activated $KRAS^{G12D}$ pancreatic cancer mouse model (Hingorani et al., 2003; Jackson et al., 2001), there was a marked increase in ductal expression and a unique expansion of islet DCLK1 that correlated with progressive neoplastic changes. These data taken together, demonstrate that DCLK1 is a novel pancreatic stem cell marker expressed in the pancreatic duct and in islets as well as a marker of pancreatic cancer stem cells. Furthermore, this Example demonstrates the isolation of DCLK1 expressing cells by FACS, which formed spheroid-like structures in suspension culture. When injected subcutaneously into flanks of nude mice, nodules formed and contained cells expressing markers of early pancreatic development (PDX-1), glandular epithelium (cytokeratin 14), and islets (somatostatin and secretin). These data taken together identify DCLK1 as a novel pancreatic ductal and islet stem/progenitor cell marker that can be employed as a target for pancreatic cancer tumor eradication. DCLK1 also represents a novel marker for studying the mechanisms that regulate pancreatic and/or islet regeneration.

Materials and Methods for Example 2

Experimental animals. 6-8 weeks old C57BL/6, athymic nude mice (NCr-nu) (National Cancer Institute, Frederick, Mass.) and $Pdx48^{Cre}$-activated KRASG12D (obtained from Dr. Rao) were used for the experiments. Mice were housed under controlled conditions, including a 12 hour light/dark cycle, with ad libitum access to diet and water. All animal experiments were performed in accordance with the University's Institutional Review Board.

Tissue procurement. The human pancreatic adenocarcinoma tissue samples were derived from patients undergoing a surgical resection of the pancreas at the University of Oklahoma Health Sciences Center. The collection of samples conformed to the policies and practices of the University's Institutional Review Board (protocol number 04586).

Immunohistochemistry. Heat Induced Epitope Retrieval was performed on formalin-fixed paraffin-embedded sections utilizing a pressurized Decloaking Chamber (Biocare Medical Inc., Concord, Calif.) in citrate buffer (pH 6.0) at 99° C. for 18 minutes. (a) Brightfield: Slides were incubated in 3% hydrogen peroxide, then normal serum and BSA at room temperature for 20 minutes. After incubation with primary antibody (DCLK1, insulin, glucagon, somatostatin, PDX-1 (Abcam Inc., Cambridge, Mass.), 14-3-3 σ (IBL), NGN3, nestin, vimentin, cytokeratin-14 and secretin (Santa Cruz Biotechnology Inc., Santa Cruz, Calif.)) the slides were incubated in polymer-HRP secondary (Dako, Carpinteria, Calif.). Slides were developed with Diaminobenzidine (Sigma-Aldrich, St. Louis, Mo.). Tyramine signal amplification for NGN3 in adult mouse tissues was performed as per manufacturer's instructions (Invitrogen, Carlsbad, Calif.) (b) Fluorescence: Slides were incubated in normal serum and BSA at room temperature for 20 minutes. After incubation with primary antibody, slides were incubated in appropriate ALEXA FLUOR® conjugated secondary antibody (488 (green) and 568 (red); Life Technologies Corp., Grand Island, N.Y.).

Microscopic examination. Slides were examined utilizing the Nikon 80i microscope and DXM1200C camera for brightfield. Fluorescent images were taken with PlanFluoro objectives, utilizing CoolSNAP™ ES2 camera (Photometrics, Tucson, Ariz.). Images were captured utilizing NIS-Elements software (Nikon Inc., Melville, N.Y.).

Stem cell isolation from mouse pancreas. DCLK1+ stem cells were isolated and propagated from mouse pancreas according to the procedures developed in neural (Singh et al., 2004; Singh et al., 2003; Singh et al., 2004A) and breast stem cell biology (Dontu et al., 2003). The pancreas and associated duct were rapidly dissected and perfused with 3 ml of cold HBSS containing 1 mg/ml collagenase and 1 mg/ml BSA (Mediatech, Inc., Manassas, Va.). The pancreatic tissues were minced and incubated in HBSS for 13 minutes at 37° C. Digestion was stopped with cold HBSS (Mediatech, Inc.) containing 10% serum. The solution was shaken by hand for 1 min, washed 3 times with serum free HBSS and filtered through 400 mM mesh (SPECTRUM® Laboratories, Inc., Rancho Dominguez, Calif.). The cells obtained were incubated with trypsin (Mediatech, Inc.) at 37° C., pipetted to create a single cell suspension and subjected to FACS based on cell surface expression of DCLK1.

FACS sorting. The single cell suspension was incubated with 1:100 dilution of ALEXA FLUOR® 568 (Life Technologies Corp., Grand Island, N.Y.) conjugated DCLK1 antibody targeting the C-terminal extracellular domain for 25 minutes and washed twice with HBSS containing 10% serum. The cells were sorted using Influx-V cell sorter (Cytopeia Inc., Seattle, Wash.) and collected cells were grown in tissue culture media: DMEM (Mediatech, Inc., Manassas, Va.) containing EGF (25 ng/ml), bFGF (20 ng/ml) and Insulin (5 ng/ml) (Sigma-Aldrich, St. Louis, Mo.) without serum on non-treated or ultra-low adherent plates (BD Biosciences, San Jose, Calif.) in a suspension culture.

Isotransplantation assay. Collected cells expressing DCLK1 were allowed to form spheroids in suspension culture for 21 days. Spheroids were disassociated, suspended in MATRIGEL® and injected subcutaneously into the flanks of athymic nude mice (NCr-nu) (National Cancer Institute, Frederick, Mass.) housed in specific pathogen-free conditions. Animals were sacrificed, nodules excised, fixed in 10% buffered formalin and subjected to immunohistochemical analysis.

Results of Example 2

Pancreatic DCLK1 expression. DCLK1 is expressed in the main pancreatic duct (FIG. 8A) and on the periphery of pancreatic islets (FIG. 8B). There was no detectable DCLK1 expression within acinar cells in uninjured mice (FIG. 8C). In order to determine the specific islet cell sub-type, co-expression of the endocrine markers somatostatin (d-cell), glucagon (a-cell) and insulin (b-cell) was evaluated. It was found that both DCLK1 (FIG. 8D) and somatostatin (FIG. 8E) were expressed in the islet periphery. Merged images revealed co-staining of DCLK1 with somatostatin (FIG. 8F). Glucagon was also found in the periphery of the islet (FIG. 8H) but did not co-localize with DCLK1 (FIG. 8I). Insulin expressing cells were observed throughout the islet (FIG. 8K), but no co-immunostaining with DCLK1 was observed (FIG. 8L). Thus DCLK1 expressing cells do not express the two major endocrine cell markers (insulin and glucagon) but do co-localize with somatostatin expressing cells.

Figure 9:
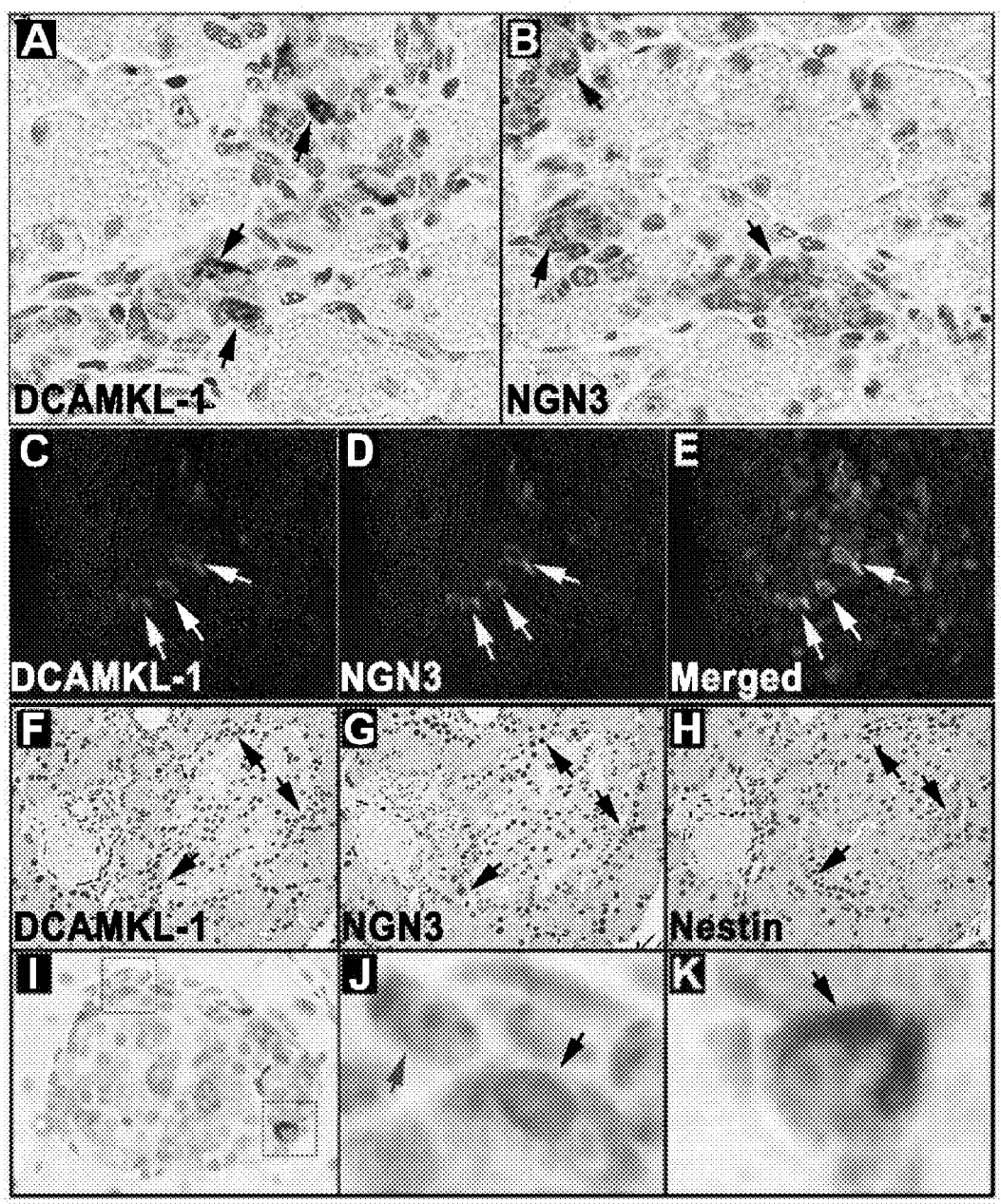

Pancreatic stem cell markers. The basic helix-loop-helix transcription factor NGN3 controls endocrine cell fate specification. All the major islet cell types, including insulin-producing b-cells, are derived from NGN3-positive endocrine progenitor cells (Johansson et al., 2007). It is well known that NGN3 protein expression diminishes as mice reach adulthood (Schwitzgebel et al., 2000; Jensen et al., 2000). Immunohistochemical analysis was employed in order to determine the cell specific expression patterns of DCLK1 in newborn mice, and with reference to NGN3 expression (Gu et al., 2002). Distinct expression of DCLK1 (FIG. 9A, referred to as "DCAMKL-1" therein) and NGN3 (FIG. 9B) was observed in early islet formations. Immunofluorescence staining confirmed the presence of DCLK1 (FIG. 9C) and NGN3 (FIG. 9D) with merged images revealing distinct co-localization within these developing tissues (FIG. 9E).

To confirm these findings in adult uninjured mice, immunohistochemical staining was employed on serial tissue sections. Common immunolocalized staining was observed for DCLK1 (FIG. 9F), NGN3 (FIG. 9G) and the pancreatic stem cell marker candidate nestin (FIG. 9H) in all three sections. To further investigate co-localization of DCLK1 and nestin expressing cells, doublelabeled immunoperoxidase staining was employed. Both distinct DCLK1 and nestin expressing cells were observed (FIGS. 9I and 9J), as well as co-localization within the pancreatic islet periphery (FIG. 9K). These data demonstrate that DCLK1 marks pancreatic islet stem/progenitor cells, based on positional evidence, and co-expression with established markers of pancreatic stem/progenitor cells.

DCLK1 expression in human pancreatic cancer. Next, DCLK1 expression in human pancreatic adenocarcinoma was examined. Samples were obtained from patients undergoing surgical resection of pancreatic cancer provided by Dr. Russell Postier. Tumors demonstrated strong DCLK1 expression. However within the histologically normal appearing resection specimen, DCLK1 was observed within islets but not in the intervening stromal cells or ducts (FIG. 10A top left). Within a neoplastic focus of the tumor resection specimen however, intense spindle-shaped cytoplasmic staining of DCLK1 is evident (FIG. 10A top right). DCLK1 expression in ductal epithelial cells within the tumor (FIG. 10A bottom left) and in intervening stromal elements is also observed (FIG. 10A bottom right).

14-3-3 σ expression in pancreatic cancer. Previously, using DNA array technology, several groups have demonstrated increased 14-3-3 σ mRNA expression in pancreatic ductal adenocarcinoma compared to normal pancreas (Guweidhi et al., 2004). Similarly, 14-3-3 σ protein nuclear localization has been described in pancreatic cancer (Logsdon et al., 2003). In normal appearing pancreatic tissue of patients undergoing surgical resection, cytoplasmic staining was observed for 14-3-3 σ and DCLK1 at the islet periphery, albeit in distinctly separate cells. No ducts expressing 14-3-3 σ were observed in that particular specimen (FIG. 10B left and right). Next, immunostaining was performed on a primary tumor specimen obtained from another patient with pancreatic ductal adenocarcinoma. While strong cytoplasmic expression of 14-3-3 σ (a marker of advanced PanIN lesions) was found in ductal epithelial cells, cells with nuclear localized 14-3-3 σ expression were also observed within tumor islet formations. Moreover, some of these nuclear 14-3-3 σ expressing cells also co-expressed DCLK1 (FIG. 10C left and right) suggesting that nuclear translocation of 14-3-3 σ occurs in putative pancreatic cancer stem cells. Expression of DCLK1 was also found in PanIN type lesions (FIG. 10D left). Additionally strong cytoplasmic 14-3-3 σ and DCLK1 co-staining was observed within the lesions (FIG. 10D right). These data strongly support a role for 14-3-3 σ and DCLK1 in the progression of pancreatic cancer and as a putative marker of pancreatic CSCs.

Figure 11:
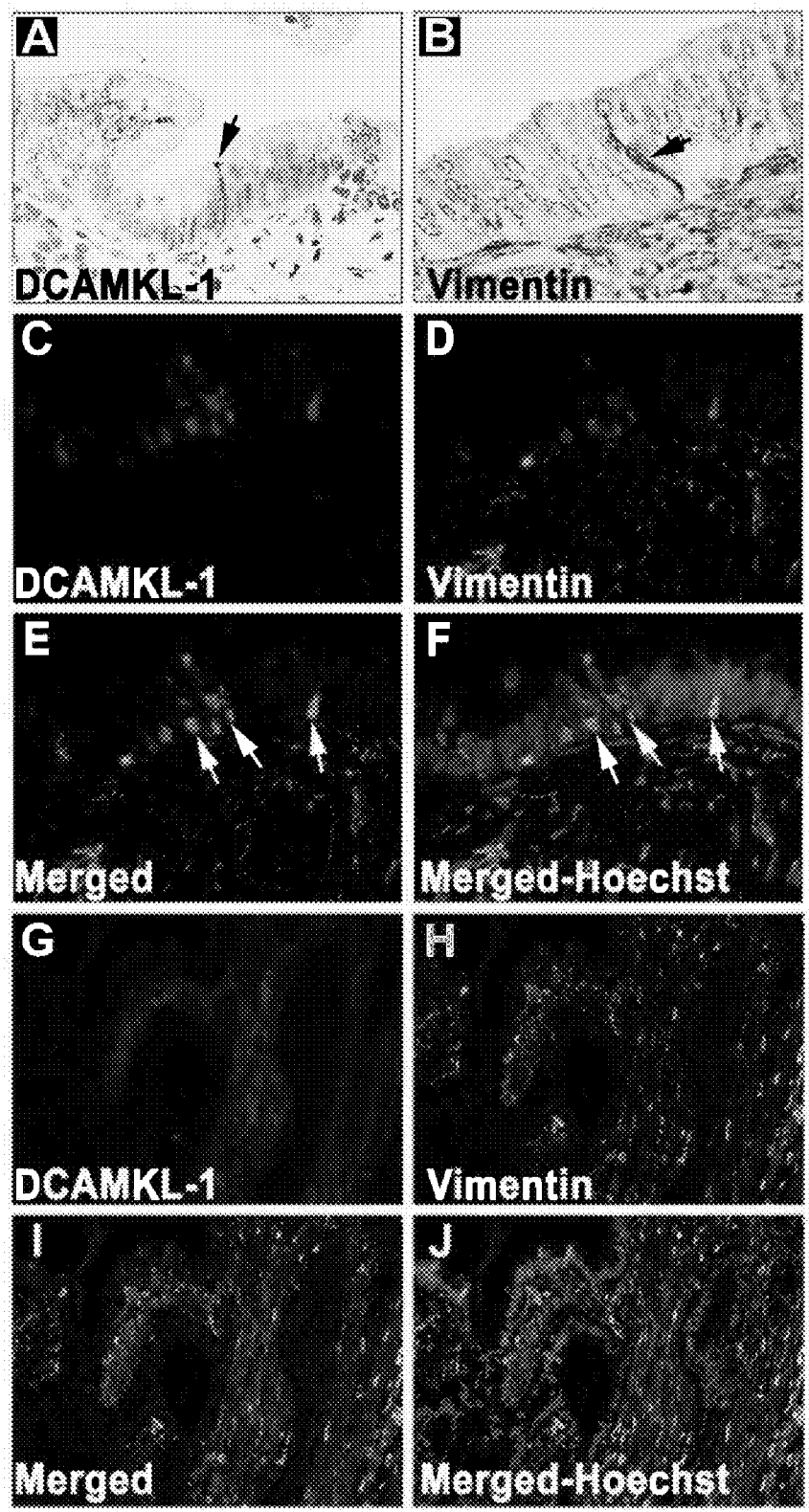
Figure 12:
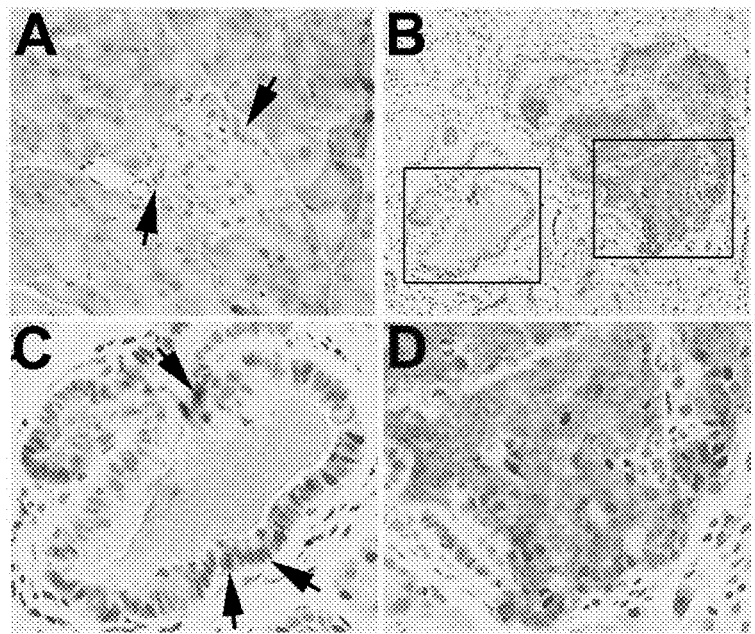

DCLK1 expression in the stroma of human pancreatic adenocarcinoma tissue. Initially, DCLK1+ staining was observed in elongated cells in the surface epithelium of PanIN lesions (FIG. 11A; DCLK1 referred to as "DCAMKL-1" therein). Further characterization of these cells by vimentin (a marker of mesenchymal lineage) immunostaining demonstrated cells that were morphologically similar to DCLK1 expressing cells (FIG. 11B). When doublelabeled immunofluorescence was performed, coexpression of DCLK1 and vimentin within the PanIN lesion was observed (FIG. 11C-F). Strong fibrillar DCLK1 expression was also seen in the stromal/mesenchymal compartment of human pancreatic adenocarcinoma tissue and confirmed by vimentin co-immunostaining (FIG. 11G-J). These data taken together demonstrate a potential role of DCLK1 in epithelial mesenchymal transition (EMT) (Turley et al., 2008).

Mouse pancreatic cancer model. The Pdx48$^{Cre}$-activated KRAS$^{G12D}$ is a well established mouse model of pancreatic cancer (Hingorani et al., 2003; Jackson et al., 2001). These mice develop PanIN lesions (similar to humans) and pancreatic cancer after 10 weeks. Furthermore, these mice develop cancer metastasis by 32 weeks (Jackson et al., 2001; Hingorani et al., 2003). Pancreatic tissues from 5-month-old Pdx48$^{Cre}$-activated KRAS$^{G12D}$ and their wild-type (WT) littermates were immunostained for DCLK1. A marked increase in ductal expression and a unique expansion of islet DCLK1 was found in the Pdx48$^{Cre}$-activated KRAS$^{G12D}$ pancreatic cancer mouse model that correlated with progressive neoplastic changes (FIGS. 12A-D). These data demonstrate that DCLK1 upregulation following mutant KRAS mediated tumorigenesis may represent a marker of neoplastic transformation.

Figure 13:
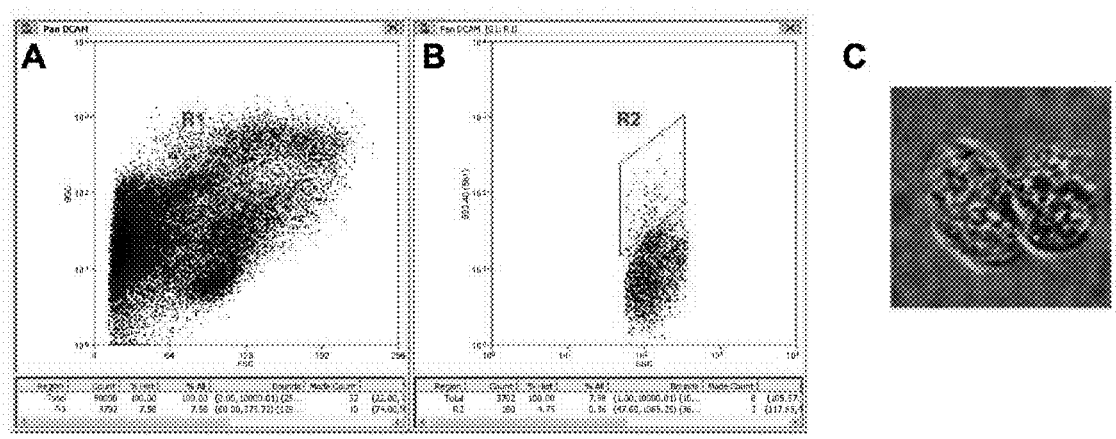
Figure 14:
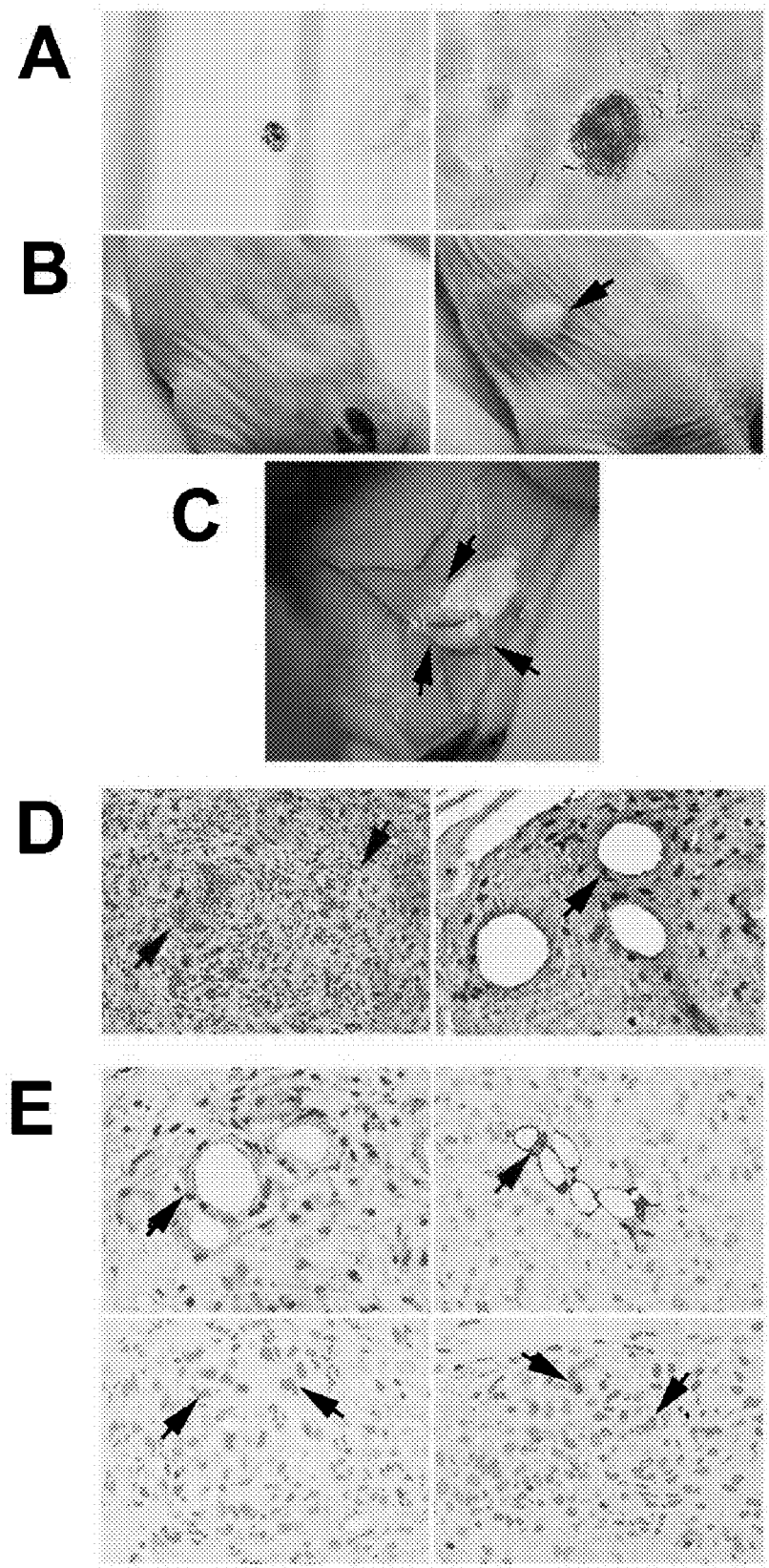

Isolation and propagation of pancreatic stem/progenitor cells. Stem cells within a tissue are capable of self-renewal and differentiation. Dontu et al., (Dontu et al., 2003) isolated human mammary stem/progenitor cells from normal breast tissues. When grown in ultra low attachment plates, they formed spheroid structures termed "mammospheres." To test the hypothesis that there is a small subpopulation of distinct stem/progenitor cells within a normal uninjured rodent pancreas, the mouse pancreas was digested with ultra pure collagenase IV, and FACS based cell sorting for DCLK1 was performed. On average, approximately 0.4% of total cells were sorted using this method (FIG. 13). Three weeks after sorting, the formation of spheroids was observed in growth factor supplemented serum free media (Dontu et al., 2003) (FIG. 14A left—day 0 and 14A right—day 21). Spheroids were separated, suspended in MATRIGEL®, and injected subcutaneously into the flanks of athymic nude mice. After four weeks, nodular growth was noted at the site of injection compared to the MATRIGEL® injected control (FIGS. 14B left—MATRIGEL® alone and 6B right—DCLK1 spheroid and MATRIGEL® injected). Interestingly, tangrey soft tissue outgrowth was noted that extended beyond the original injection site, which appeared to show new blood vessel formation (FIG. 14C).

DCLK1 sorted spheroids induce pancreatic epithelial expression in the flanks of nude mice. Histological analysis of the excised nodules revealed single cells with oval nuclei and large nucleoli, which appeared to be epithelial in nature, as well as islet-like structures (FIG. 14D). The glandular epithelial origin of these cells was confirmed by cytokeratin-14 immunoreactivity (FIG. 14E top left) (Moll et al., 2008; Purkis et al., 1990) and PDX-1, marker of early pancreatic development (FIG. 14F top right). Additionally, many of the cells within the islet structures expressed secretin (Pollack et al., 1990) (FIG. 14E bottom left) and somatostatin (FIG. 14E bottom right). These data taken together demonstrate that DCLK1 expressing cells isolated from the pancreas of normal uninjured mice by FACS and utilized in isotransplantation assays, are in fact stem/progenitor cells.

Discussion of Example 2

Solid tumors are histologically heterogeneous and include tumor cells, stroma, inflammatory infiltrates, and vascular structures. In recent years, the CSC model of tumorigenesis has received increasing attention (Tang et al., 2007). This model suggests that tumors are initiated and maintained by a minority subpopulation of cells that have the capacity to self-renew and to generate the more differentiated progeny making up the bulk of a tumor. The CSCs, tumorigenic cancer cells, can give rise to new tumors when transplanted into immunodeficient animals (Diehn et al., 2006).

The existence of CSCs has profound implications for cancer biology and therapy due to the likelihood that eradication of CSCs is the critical determinant in achieving cure. Furthermore, CSCs may be particularly resistant to chemotherapy and radiation therapy. A recent report (Phillips et al., 2006) demonstrated that breast cancer-initiating cells were radioresistant when compared with breast cancer cells that were incapable of initiating tumors. Similarly, another report (Bao et al., 2006; Bao et al., 2006A) suggested that glioblastoma stem cells are radioresistant and may, therefore, contribute to treatment failures.

Figure 15:
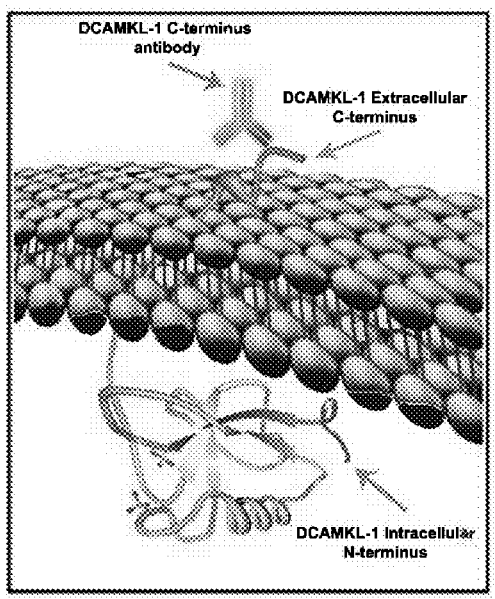

In general, cell surface proteins used for isolation of CSCs must currently be viewed as purification markers without functional implication (Diehn et al., 2006). Therefore, it is critical to demonstrate that isolated cells from any particular tissue have the functional characteristics of CSCs. Currently, this has been most convincingly demonstrated by serial transplantation in animal models (Diehn et al., 2006). CSCs share unique properties with normal adult stem cells, including the ability to self-renew and form spheroids. Indeed in the experiments described herein, stem cells isolated from normal mouse pancreas formed spheroids. Furthermore, 50-100 cells isolated from a particular spheroid were capable of initiating growth in the flanks of nude mice. In this Example, evidence is provided that demonstrates that DCLK1, a novel stem cell marker expressed primarily in quiescent cells of the gut (May et al., 2008; Giannakis et al., 2006A), also marks normal pancreatic stem cells. One exciting outcome of this Example however, is the use of FACS for isolation of cells expressing DCLK1. Although originally considered to be a cytoplasmic protein (Giannakis et al., 2006A), analysis of the DCLK1 protein using TMPred program (available on the EMBnet Switzerland website) suggested that amino acids 534-560 of SEQ ID NO:2 represent a transmembrane domain, and amino acids 561 to 729 of SEQ ID NO:2 are outside the cell. Furthermore, it has been reported that DCLK1 is expressed in adult brain with two transmembrane domains (amino acids 534-559 and 568-585 of SEQ ID NO:2), which strongly supports the suggestion that it is a cell surface expressing protein with both intra and extracellular domains (Sossey-Alaoui et al., 1999; Kim et al., 2003). Cell surface DCLK1 expression was demonstrated by Pierce Cell Surface Protein Isolation Kit (Pierce Biotechnology Inc., Rockford, Ill.) followed by Western Blot for DCLK1 (data not shown). Accordingly, an ALEXA FLUOR® 568 (Life Technologies Corp., Grand Island, N.Y.) conjugated anti-DCLK1 antibody was generated, which targets the putative extracellular C-terminal epitope (FIG. 15). In this Example it has been demonstrated that putative stem cells isolated from the normal mouse pancreas formed early epithelial and islet-like structures and expressed markers of early pancreatic development, glandular epithelium, and islets in nude mice. In addition to expression in normal mouse pancreatic tissues, distinct DCLK1 expression was also observed in representative human pancreatic cancers and the Pdx48$^{Cre}$-activated KRAS$^{G12D}$ mouse model of pancreatic cancer. Interestingly, marked coexpression of DCLK1 was observed within tumors that expressed 14-3-3 σ, an inhibitor of Bad proapoptotic activity (Masters et al., 2001). The co-localization demonstrated in this report of 14-3-3 σ and DCLK1 is significant in that it could potentially define a target cell in which 14-3-3 σ related transcriptional activation within a tumor might occur. These data suggest that within a particular tumor, subsets of potential CSCs can be identified in situ. DCLK1 immunostaining was observed in the intervening stroma between epithelial tumor elements, which co-expressed vimentin. These findings were indeed surprising in that DCLK1 was not observed in non-epithelial cells under basal conditions. Next, ductal DCLK1 was evaluated within PanIN lesions. Several thin, elongated cells that appeared to be mesenchymal were observed. To further investigate this, tumor sections were immunostained for vimentin, and cells of similar morphology were found interspersed between epithelial cells within PanIN lesions, which demonstrated distinct co-expression with DCLK1. These findings suggest that DCLK1 expressing cells may be undergoing EMT (Turley, et al., 2008; Reya et al., 2001). EMT is a phenotypic conversion that facilitates organ morphogenesis and tissue remodeling in physiological processes such as embryonic development, wound healing, fibrosis, and neoplasia, and is also associated with disease progression (Turley et al., 2008). Desmoplasia, the appearance of fibrous, mesenchymal-like tissue in the peritumor stroma, is associated with poor clinical outcome (Poste et al., 1982). Indeed, gene-profiling studies suggest that mesenchymal gene profiles in tumors are predictive of poor clinical outcome (Diehn et al., 2006; Theodosiou et al., 2003). Myofibroblasts have long been thought to be derived from fibroblasts, but recent data has shown that a substantial proportion of these cells is derived from EMT and is associated with tumor progression (Polakis, 2000). Our findings suggest that in addition to its role as a marker of pancreatic stem cells, DCLK1 may additionally mark EMT within pancreatic cancer tissues.

Identification of stem cells within the normal pancreas and tumors has been generally elusive. Although recent studies using cell surface markers to isolate CSCs from tumors have been described, similar studies have not been performed utilizing normal tissues. However, in this Example, the novel stem cell marker DCLK1 has been employed to identify stem cells in the normal mouse pancreas and in human and mouse pancreatic cancer.

Overall, the cancer stem cell hypothesis has many potential clinical applications, as it is becoming clear that CSCs must be removed in addition to the aberrantly proliferating cells within a particular cancer. Pancreatic cancer is an exceptionally aggressive disease and efforts directed at identification of novel therapeutic options aimed at improving the prognosis are essential. DCLK1 may represent a new target for eliminating pancreatic cancer stem cells and the development of novel treatments for this devastating disease.

Example 3

The adult intestinal epithelium is continuously and rapidly replaced by cell replication within the crypts of Lieberkühn and subsequent migration of their progeny onto the villus epithelium in the small intestine, or onto the surface epithelium in the colon (Gordon et al., 1994). Intestinal epithelial cells are ultimately derived from multipotent stem cell(s) located near the base of each intestinal crypt (Cheng et al., 1974; Cohn et al., 1992; Schmidt et al., 1985; Winton et al., 1990). In the adult mouse small intestine, crypt stem cells divide to produce a daughter stem cell (self-renewal) as well as a more rapidly replicating transit amplifying (TA) cell. TA cells divide in the crypt proliferative zone and their progeny ultimately differentiate into the mature intestinal epithelial cell types (Cheng et al., 1974; Potten et al., 1987; Potten et al., 1990). Knowledge of the biological characteristics of intestinal stem cells (ISCs) has been largely acquired by inference from experiments using chimeric and transgenic mice (Gordon et al., 1994; Schmidt et al., 1985; Hauft et al., 1992). Bjerknes and Cheng (Bjerknes et al., 1981) originally proposed the existence of a stem cell-permissive microenvironment near the crypt base at positions 1-4 interspersed between Paneth cells. These cells, termed crypt base columnar (CBC) cells were proposed as ISCs (Cheng et al., 1974A) and were found to give rise to mutant clones containing multiple cell types (Bjerknes et al., 1999).

Adult stem cells in mammals exist either in a prolonged quiescent state or are extremely slow cycling (Cheshier et al., 1999). Based on this feature, long-term label retention assays were developed to assist in the localization of putative stem cells (Cotsarelis et al., 1990; Zhang et al., 2003). Using this technique, Potten et al., (Potten et al., 2002) localized label-retaining cells (LRCS) or putative ISCs to a position +4 from the crypt base, directly above the Paneth cell zone (Marshman et al., 2002). However the +4 position is an average location and may vary depending on the crypt being analyzed. It is important to note that not all +4 cells are putative stem cells.

Recent work presented by Barker et al., (Barker et al., 2007) has identified a single marker, LGR5/GPR49 gene, a leucine-rich orphan G-protein-coupled receptor, that specifically labels stem cells in the mouse small intestine as well as other adult tissues. Furthermore, using mice generated from a LGR5-EGFP-IRES-Cre-ERT2×RosaLacZ cross, they demonstrated that LGR5+ CBC cells are multipotent for all mature intestinal epithelial cell types, undergo self-renewal, persist for at least 60 days based on LacZ expression, and are resistant to irradiation (Barker et al., 2007). Furthermore, LGR5 marked ISCs that were rapidly cycling (divide every 24 hours) under homeostatic conditions (Barker et al., 2007).

It has been demonstrated herein that doublecortin and $Ca^{2+}$/calmodulin-dependent kinase-like-1 (DCLK1), a microtubule-associated kinase expressed in post-mitotic neurons (Lin et al., 2000), is a novel putative ISC marker (See Example 1, as well as Quante et al., 2008; Samuel et al., 2009; Humphries et al., 2008). DCLK1 was identified as a Gene Ontogeny-enriched transcript expressed in comparison with gastric epithelial progenitor and whole stomach libraries (Giannakis et al., 2006) and more recently in gastric stem cells (Giannakis et al., 2008). Utilizing immunohistochemical analysis, cell-specific intestinal DCLK1 expression patterns were demonstrated in adult wild type (WT) and in $Apc^{Min/+}$ mice to visualize crypt epithelial stem cells at baseline and in response to radiation injury (May et al., 2008). Immunoreactive DCLK1 cells were found at or near position +4, at a frequency of one cell per five crypts. DCLK1+ CBC cells were also observed, albeit much less frequently.

In this Example, the cell specific expression patterns of DCLK1 and LGR5 were investigated in intestinal epithelial cells in uninjured adult mice. DCLK1 and LGR5 mark distinctly different cells. Moreover, DCLK1 did not co-localize with other key markers such as chromogranin A (ChrA), phosphorylated PTEN (pPTEN), phosphorylated AKT (pAKT), somatostatin or secretin. Furthermore, using a combination of a modified label retention assay (mLRA) and immunohistochemical analysis, it was determined that DCLK1 is expressed in quiescent label retaining cells within the intestinal crypt. LGR5 identifies proliferative CBC and TA cells in the gut as evidenced by co-labeling with proliferating cell nuclear antigen (PCNA). Additionally, early glandular epithelial structures were demonstrated in nude mice isografts following fluorescence activated cell sorting (FACS) of normal mouse intestinal epithelial cells using DCLK1. Thus the inventors propose that the original hypothesis of a +4 ISC should not yet be abandoned and contend that the DCLK1 expressing cell represents a quiescent ISC.

Materials and Methods for Example 3

Tissue preparation and immunohistochemistry. Heat Induced Epitope Retrieval was performed on formalin-fixed paraffin-embedded sections utilizing a pressurized Decloaking Chamber (Biocare Medical Inc., Concord, Calif.) in citrate buffer (pH 6.0) at 99° C. for 18 minutes. (a) Brightfield: Slides were incubated in 3% hydrogen peroxide, then normal serum and BSA at room temperature for 20 minutes. After incubation with primary antibody (DCLK1 C-terminal (Abcam Inc., Cambridge, Mass.), LGR5 (Abcam Inc.), BrdUrd (Upstate, Temecula, Calif.), PCNA (Santa Cruz Biotechnology Inc., Santa Cruz, Calif.), Msi-1 (Abcam Inc.), Cytokeratin 14 (Santa Cruz Biotechnology, Inc.), Math1 (Chemicon), L-FABP (Santa Cruz Biotechnology, Inc.)), the slides were then incubated in peroxidase-conjugated EnVision™+ polymer detection kit (Dako, Carpinteria, Calif.). Slides were developed with Diaminobenzidine (Sigma-Aldrich, St. Louis, Mo.). (b) Fluorescence: Slides were first incubated in Image-iT FX signal enhancer (Invitrogen, Carlsbad, Calif.), followed by normal serum and BSA at room temperature for 20 minutes. After incubation with primary antibody, slides were incubated in appropriate ALEXA FLUOR® conjugated secondary antibody (488 (green) and 568 (red); Life Technologies Corp., Grand Island, N.Y.).

Microscopic examination. Slides were examined utilizing the Nikon 80i microscope and DXM1200C camera for brightfield. Fluorescent images were taken with PlanFluoro objectives, utilizing CoolSNAP™ ES2 camera (Photometrics, Tucson, Ariz.). Images were captured utilizing NIS-Elements software (Nikon Inc., Melville, N.Y.). Confocal imaging was performed using Leica TCS NT Microscope.

Modified label retention assay. C57BL/6 mice (Jackson Immuno Research Laboratories, Inc., West Grove, Pa.) were subjected to 8 Gy whole body gamma irradiation using a Nordion $^{137}$Cs γ-irradiator with a dose rate of 0.9 Gy per minute. Animals received twice daily BrdUrd injections beginning 24 and ending 84 hours after irradiation. This time period was chosen in order to maximize the potential of label incorporation during the crypt regeneration phase, following severe genotoxic injury. Animals were sacrificed at 7 and 10 days after the initial injury when restoration of crypt villus morphology is returning towards baseline. Co-immunostaining for BrdUrd and DCLK1 was performed to identify label retaining stem cells. Additionally co-immunostaining for PCNA and DCLK1 was performed to determine the proliferative status of the label retaining cells.

Stem cell isolation. Based on protocols developed in intestinal stem cell biology (Dekaney et al., 2005; Grossmann et al., 2003), stem cells were isolated and propagated from fresh mouse intestinal tissues. Intestines were opened longitudinally and cut into small strips, washed and incubated with 1 mM DTT (Sigma-Aldrich, St. Louis, Mo.) for 30 minutes at room temperature. Tissues were further incubated with 30 mmol/L EDTA (Sigma-Aldrich, St. Louis, Mo.) for 10 minutes at 37° C., shaken vigorously in fresh HBSS (Mediatech, Inc., Manassas, Va.) and filtered through 400 μm mesh (SPECTRUM® Laboratories, Inc., Rancho Dominguez, Calif.) to separate the detached intestinal crypt epithelial cells from the tissue. The filtrate was passed through 80 μm mesh (BD Biosciences, San Jose, Calif.) to retain the crypts and washed. The crypts were digested at 37° C. to create a single cell suspension.

FACS. The cells isolated from mouse intestine were incubated with 1:100 dilution of ALEXA FLUOR® 568 (Life Technologies Corp., Grand Island, N.Y.) conjugated DCLK1 antibody (Abcam Inc., Cambridge, Mass.) for 30 minutes. The cells were washed twice with HBSS containing 10% serum and sorted using Influx-V cell sorter (Cytopeia Inc., Seattle Wash.). The cells collected were grown on DMEM containing EGF (25 ng/ml), FGF (20 ng/ml) and insulin (5 ng/ml) (Sigma-Aldrich, St. Louis, Mo.), on non adherent/ultra low attachment plates (BD Biosciences, San Jose, Calif.).

Isotransplantation assay. DCLK1+ cells isolated from intestine were grown in suspension culture and formed spheroids by day 21. Mechanically dissociated spheroids (50-100 cells) were suspended in MATRIGEL® and injected subcutaneously into the flanks of athymic nude mice (n=3) (National Cancer Institute, Frederick, Mass.) and monitored for the appearance of nodular growth.

Cell surface protein isolation and Western Blot analysis. SW480 colon cancer cells were grown and surface proteins were labeled with sulfo-NHS Biotin (Pierce Biotechnology Inc., Rockford, Ill.). Cell lysates were prepared and the biotinylated proteins were separated from intracellular non-biotinylated proteins as per manufacturer's instructions (Pierce Biotechnology Inc.). Protein concentration was determined by BCA protein assay kit (Pierce Biotechnology Inc.). Forty μg of the protein was size separated in a 15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 hour and probed overnight with a rabbit anti-DCLK1 antibody (Abcam Inc., Cambridge, Mass.) or with rabbit anti-EGFR antibody (Cell Signaling Technology, Inc., Danvers, Mass.). Subsequently, the membrane was incubated with anti-rabbit IgG horseradish peroxidase-conjugated antibodies (Amersham-Pharmacia) for 1 hour at room temperature. The 82 kDa DCLK1 and 175 kDa EGFR proteins were detected using ECL™ Western Blotting detection reagents (Amersham-Pharmacia).

Results of Example 3

Figure 16:
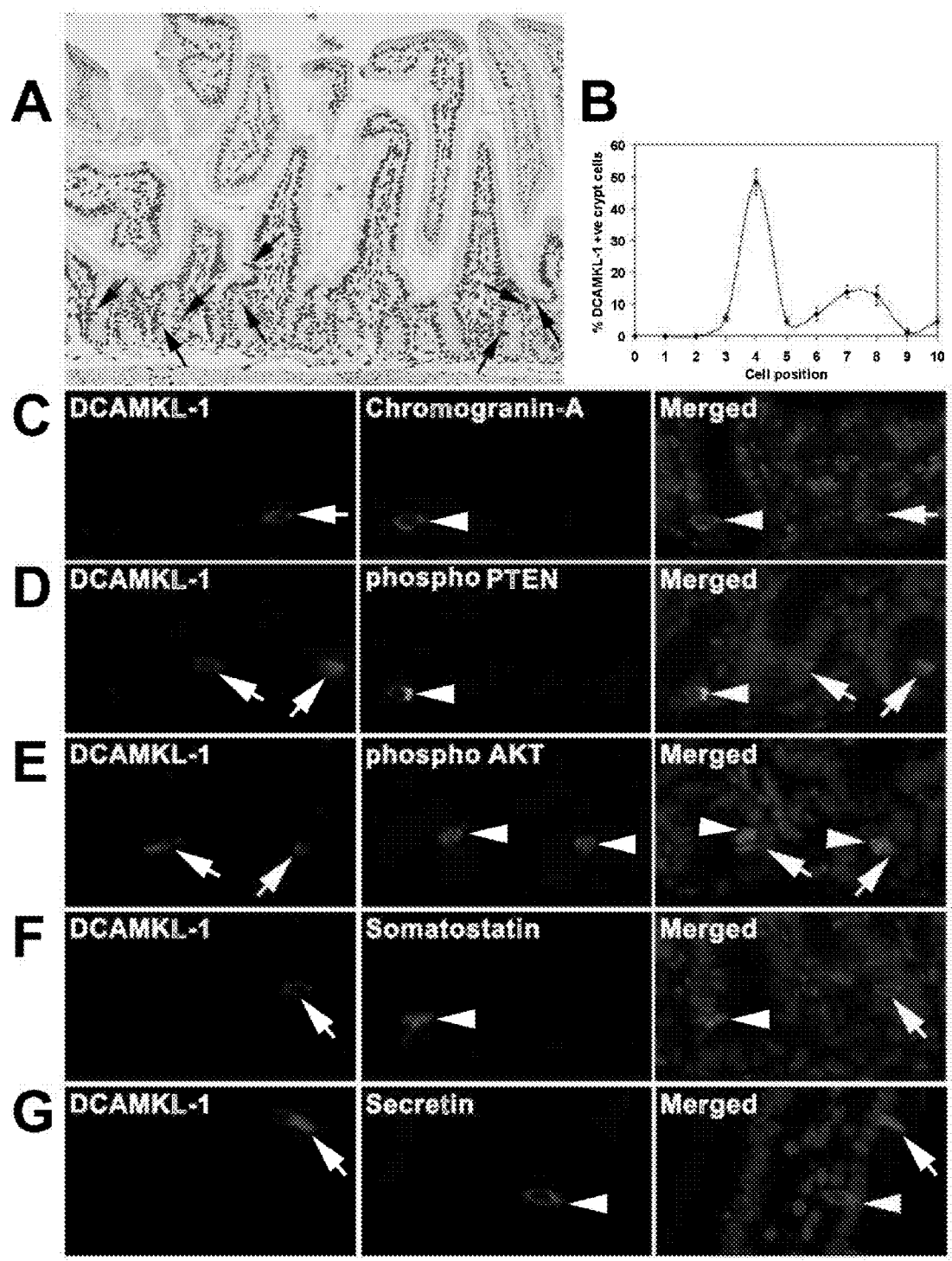

Intestinal DCLK1 expression along the crypt-villus axis. Cellular distribution of DCLK1 on a positional basis was determined in adult C57BL/6 mice (n=3). Longitudinal sections from the distal jejunum were prepared from each mouse and the number of immunoreactive DCLK1 was determined by counting positive cells at the numbered positions (1-10), starting from the mid-point at the base of the crypt along the crypt-villus axis. Out of 500 total crypts counted, it was found that 49% of DCLK1 positive cells were located at position +4 (excluding the CBCs) (FIGS. 16A, 16B). DCLK1 was also expressed in rare CBCs (4% of total crypts counted). As previously reported, DCLK1 cells were found in the villi (May et al., 2008). However, it was noted that DCLK1 crypt with simultaneous villus expression was rare (<5% of total crypt villus units).

DCLK1 marks a unique intestinal cell type. To determine whether DCLK1 was co-expressed with other putative stem cell and enteroendocrine markers, double-labeled immunofluorescence staining was performed for DCLK1 with ChrA, pPTEN, pAKT, somatostatin and secretin. There was no co-localization observed for any of the markers tested (FIGS. 16C-16G). These data demonstrate that DCLK1 marks a unique cell within the crypt.

Figure 17:
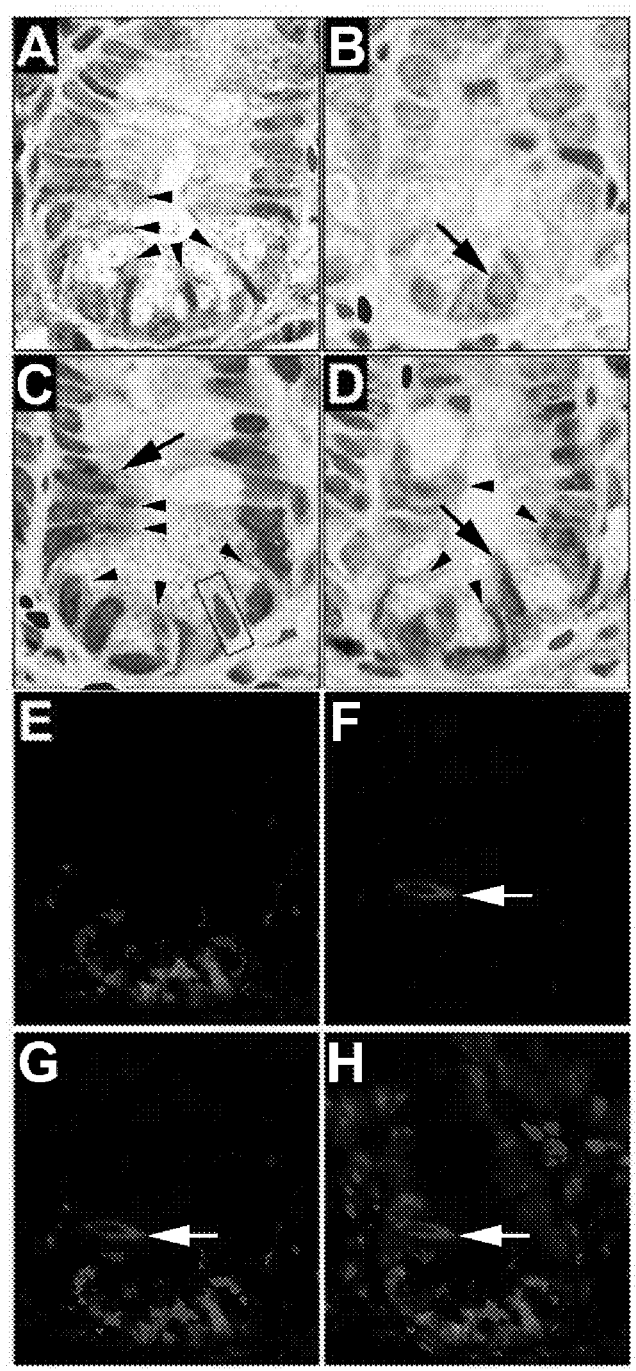

Intestinal LGR5 and DCLK1 mark distinctly different cells. In the intestine, LGR5 expression was observed in crypt epithelial and in CBC cells as predicted (FIG. 17A). LGR5+ cells were also scattered throughout the mesenchyme and villus epithelial cells. This was consistent with the LacZ expression patterns described in the original LGR5 stem cell report (Barker et al., 2007), expression of LGR5 at the base of the crypt in normal human colon and small intestine (Becker et al., 2008) and the previously reported immunostaining for LGR5/GPR49 in colon and cancer tissues (McClanahan et al., 2006). Example 1 demonstrated DCLK1 expression at position +4 and in rare CBC cells (May et al., 2008) (FIG. 17B). On occasion, LGR5 expressing cells were immediately adjacent to DCLK1+ cells (FIGS. 17C, 17D). However, no DCLK1 co-localization with LGR5 was observed in intestinal crypts (FIGS. 17E-17H).

Figure 18:
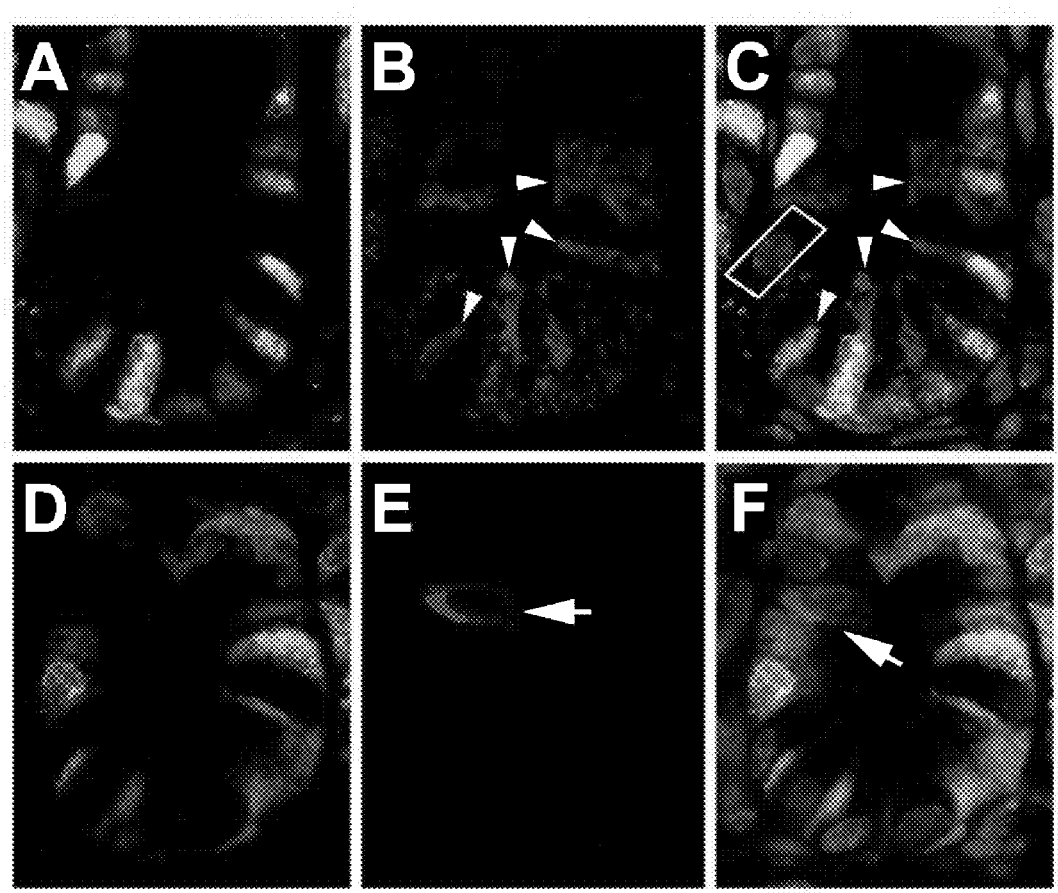

The proliferation status of LGR5 and DCLK1 expressing cells. PCNA staining was performed to assess the proliferative status of LGR5 and DCLK1 expressing cells in the intestine. LGR5 expressing cells were invariably PCNA+ (actively cycling) (FIGS. 18A-18C). Occasionally, cells were noted at position +4 that did not express either PCNA or LGR5 (FIG. 18C white box). PCNA-cells, particularly at position +4, were distinctly DCLK1+ (FIGS. 18D-18F) suggesting functional quiescence at baseline. Thus, DCLK1 and LGR5 identify cell populations with differing proliferation status at baseline. These findings lend support to the longstanding +4 hypothesis, which suggests that a functionally quiescent or very slowly cycling cell is primarily anchored in the stem cell niche (Potten et al., 2002; Marshman et al., 2002; Potten et al., 1997). The inventors contend that this quiescent cell is marked by DCLK1.

Figure 19:
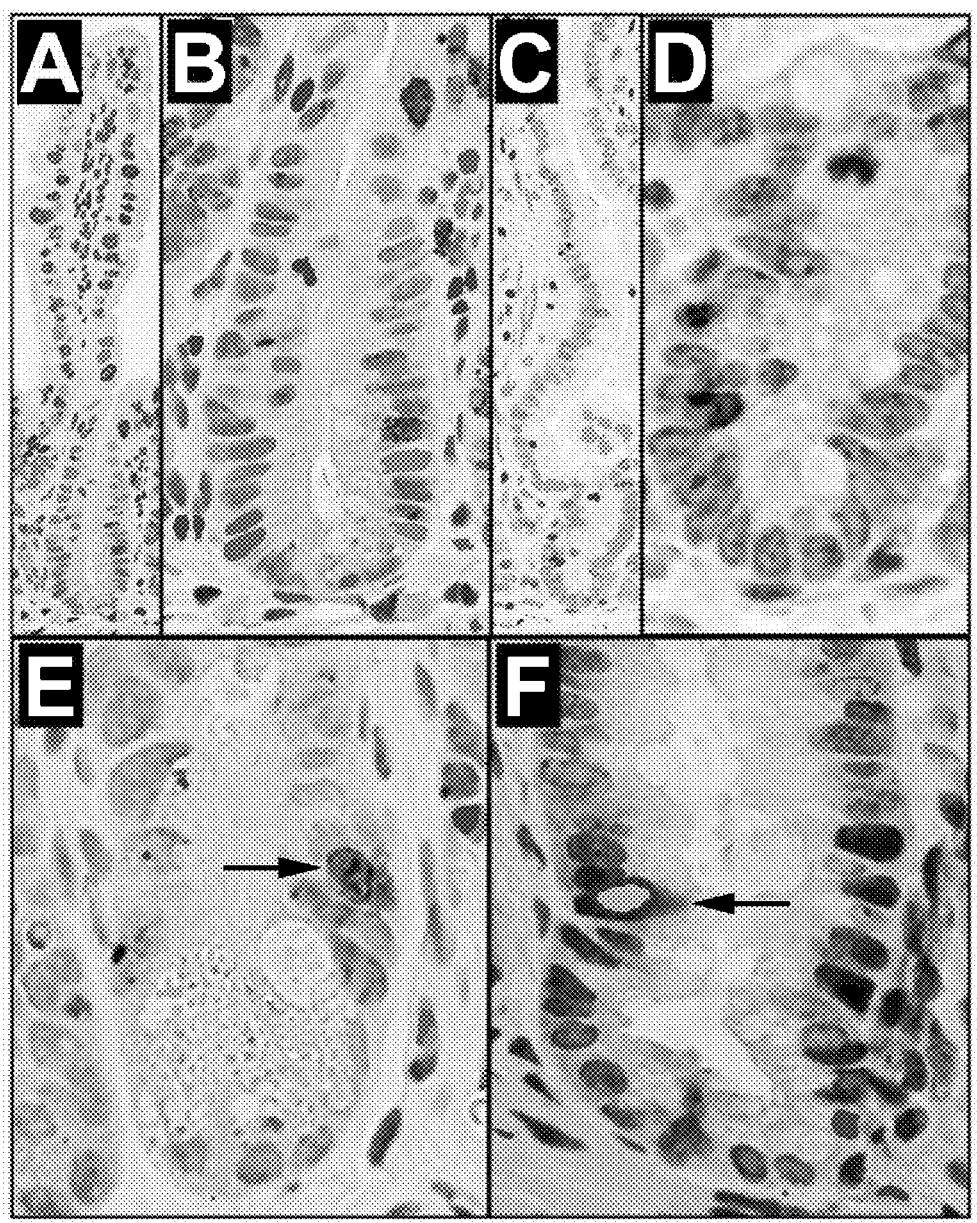

DCLK1 label-retaining cells are functionally quiescent. Although the "anchored stem cell" is often found at position +4, the inventors suspect that under certain conditions this cell can exit the niche (Frye et al., 2003). Indeed, occasionally DCLK1 staining was observed outside of the crypt, particularly in APC$^{min/+}$ mice (May et al., 2008). A modification of the traditional label retention assay (mLRA) (Cotsarelis et al., 1990; Zhang et al., 2003; Potten et al., 2002; Marshman et al., 2002) was employed by utilizing 8 Gy as the inciting dose in adult WT mice. DCLK1 expression is lost in regenerative crypts by 84 hours after lethal dose IR (>8 Gy) but reappears 7 and 10 days following IR in regenerated intestine tissues (May et al., 2008). This suggests that by 7 to 10 days after IR, the normal crypt villus units and the niche related micro-environmental signals required for DCLK1 expression are restored. Example 1 demonstrated that 24 hrs after IR is a critical time point when DCLK1 expressing cells undergo both mitosis and apoptosis (May et al., 2008). Thus it was decided to pulse label 5-bromo-2'-deoxyuridine (BrdUrd) throughout the entire 24-84 hour crypt regeneration cycle. Animals were allowed to recover and were sacrificed at 7 and 10 days (Potten et al., 1988). This period of regeneration allows for BrdUrd incorporation into dividing stem cells that would otherwise be problematic under quiescent basal conditions. At 7 days post IR, residual BrdUrd labeled cells were detected in the upper crypt and throughout the villi (FIGS. 19A, 19B). However at 10 days, BrdUrd labeling had essentially disappeared, and only rare cells near the crypt base retained significant label (FIGS. 19C, 19D).

Next, it was sought to determine whether the cells retaining BrdUrd label following the mLRA also expressed DCLK1. At 10 days post IR, double-label immunohistochemistry was performed, and distinct co-expression of BrdUrd and DCLK1 at position +4 was observed (FIG. 19E). While this cell retains label, it does not necessarily mean that it was actively proliferating. It was sought to answer this question by examining DCLK1 expressing cells following the mLRA for the presence of PCNA activity. Interestingly, there was no PCNA expression in the nucleus of the DCLK1+ cell. Yet clear PCNA staining could be identified in many adjacent cells (FIG. 19F). Thus the label retaining DCLK1 expressing "stem cells" are again quiescent at 7 and 10 days after IR.

Figure 20:
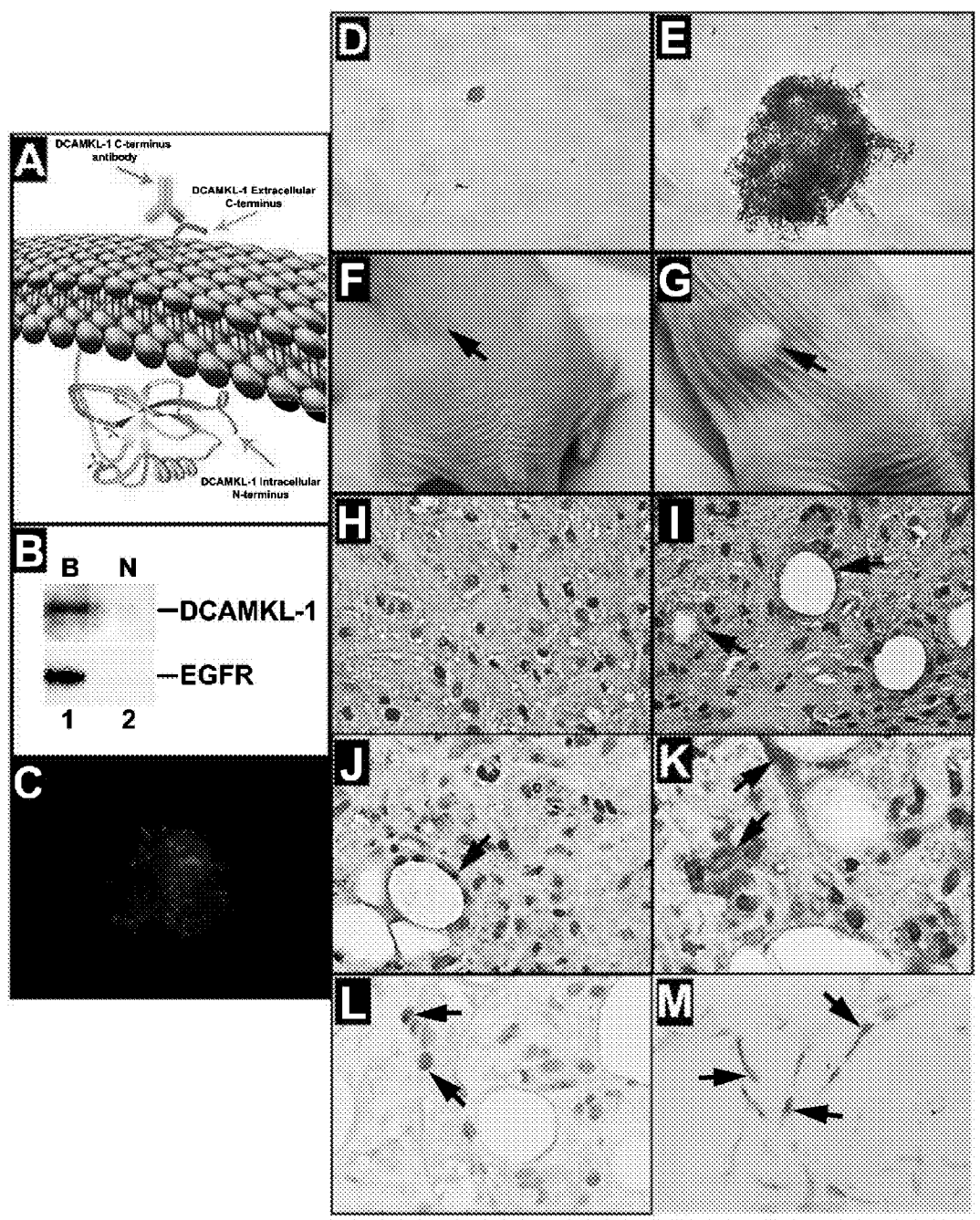
Figure 21:
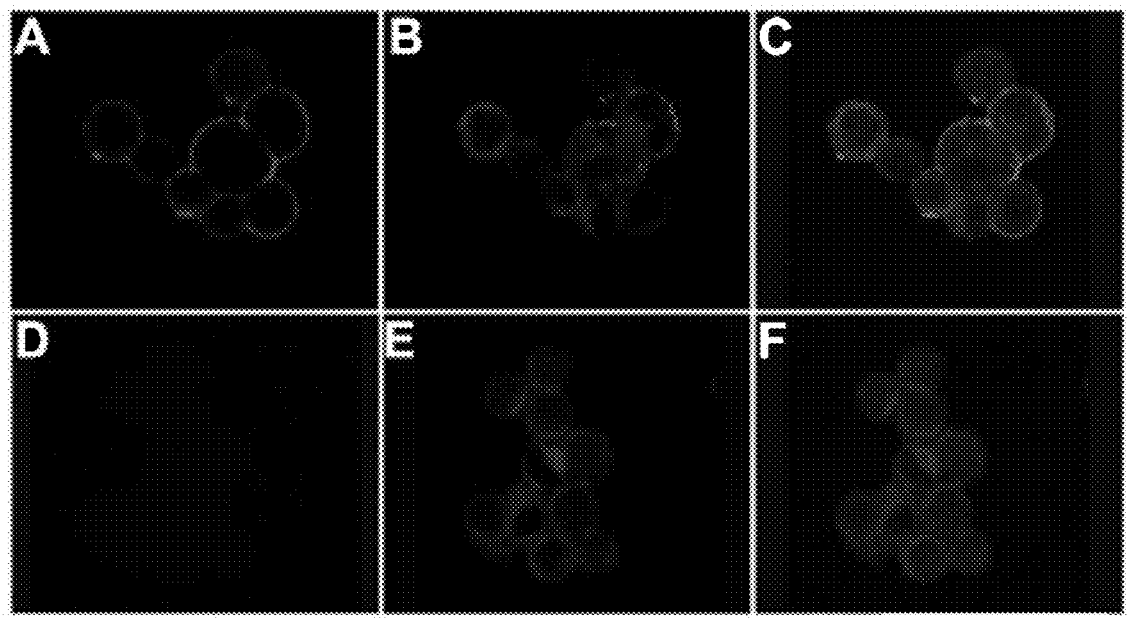

DCLK1 is expressed on the cell surface and can be used to isolate stem cells. To further investigate the potential "stemness" of DCLK1 expressing cells, FACS using the modified protocol of Dekaney et al. (Dekaney et al., 2005) was employed. Although originally considered to be a cytoplasmic protein (Giannakis et al., 2006), analysis of the DCLK1 protein using TMPred program (available on the EMBnet Switzerland website) suggested that amino acids 534-560 of SEQ ID NO:2 constitutes a transmembrane domain, and amino acids 561 to 729 thereof are extracellular. Furthermore, it has been reported that DCLK1 is expressed in adult brain with two transmembrane domains (amino acids 534-559 and 568-585 of SEQ ID NO:2), suggesting that it is a cell surface expressing protein with intra and extracellular domains (Sossey-Alaoui et al., 1999; Kim et al., 2003) (FIG. 20A). To confirm the cell surface expression of DCLK1, the Pierce Cell Surface Protein Isolation Kit (Pierce Biotechnology Inc., Rockford, Ill.) was used to isolate total cell surface expressing proteins from SW480 cells (FIG. 21). Western blot analyses demonstrated the presence of DCLK1 in the avidin-bound fraction, but not in the unbound fraction (FIG. 20B). This data demonstrates that DCLK1 protein is indeed present on the cell surface. Epithelial growth factor receptor (EGFR), a cell surface expressing protein in the bound fraction was used as a positive control.

Figure 22:
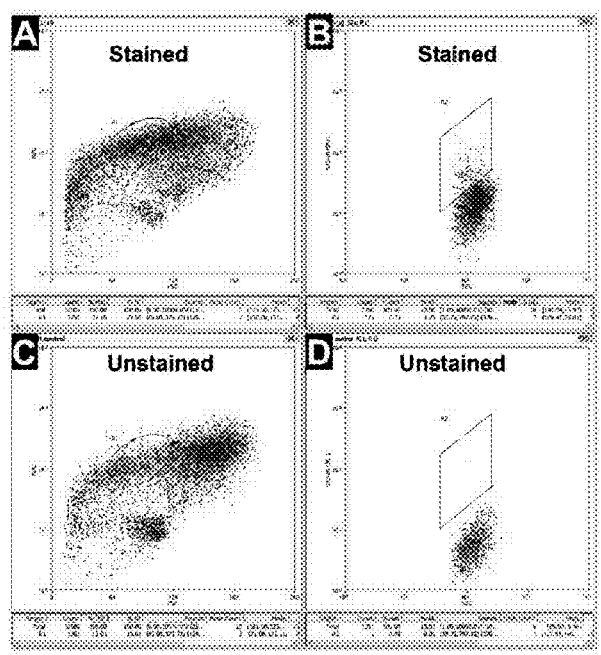
Figure 23:
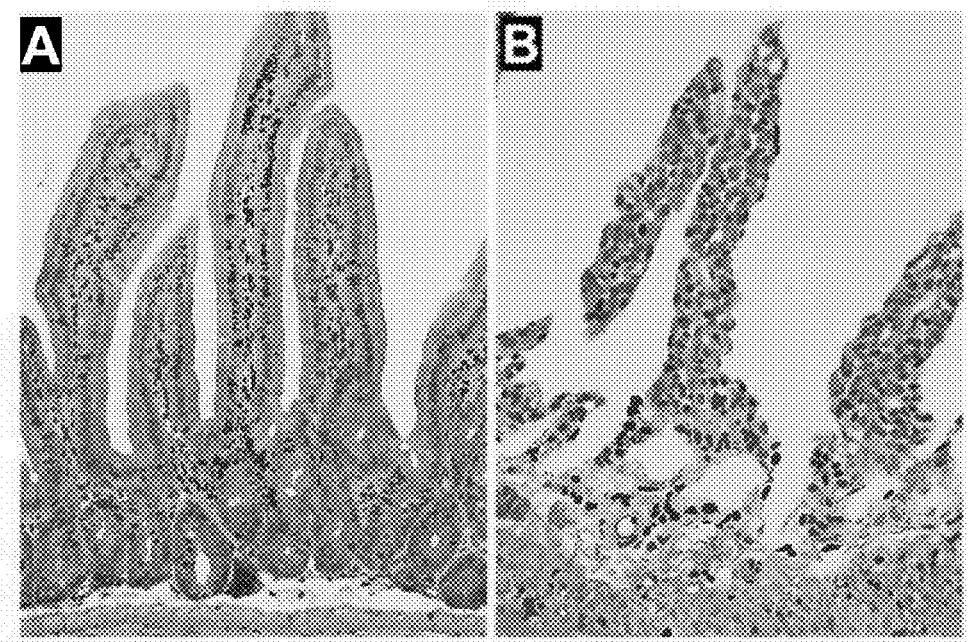
FIG. 23 illustrates mouse intestine (distal jejunum) before and after epithelial cell isolation. (A): Intact epithelium before isolation. (B): Intestine devoid of epithelial cells after isolation.
Figure 24:
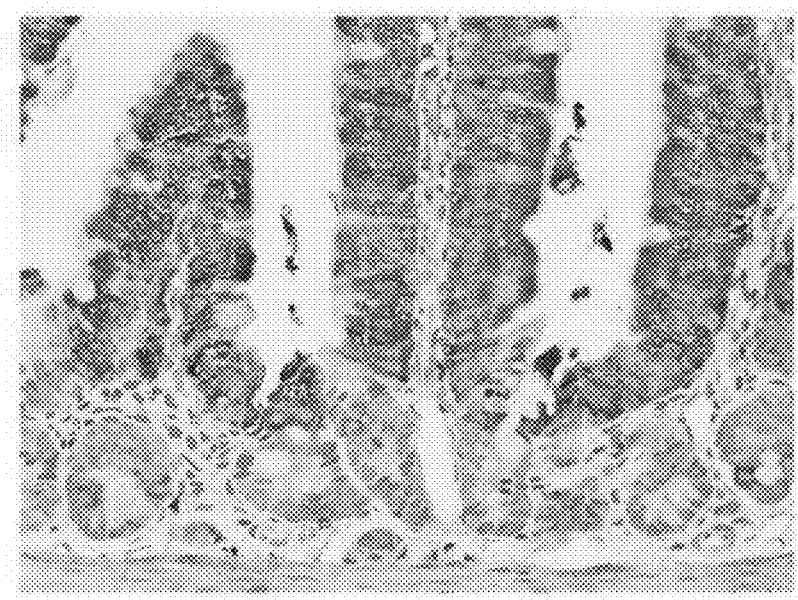
FIG. 24 illustrates mouse intestine (distal jejunum) immunostained for L-FABP (brown). Immunoreactive L-FABP is observed in occasional crypt epithelial cells; however, intense staining is observed in differentiated villus epithelial cells.

Anti-DCLK1 antibody, which targets the extracellular C-terminal epitope (Lin et al., 2000; Sossey-Alaoui et al., 1999; Kim et al., 2003), was conjugated with ALEXA FLUOR® 568 (Life Technologies Corp., Grand Island, N.Y.) to label intact functional stem cells from the normal mouse intestine for FACS. For sorting, gate R1 was assigned based on previous experiments, where the DCLK1+ fluorescing cell population was found aggregated within that location. These cells were further gated through R2 based on fluorescence intensity (FIG. 22). Approximately 1.75% of the total cells sorted were isolated using this method (FIGS. 22-23). Sorted cells were examined by fluorescence microscopy to confirm the presence of DCLK1 (FIG. 20C). The cells were then grown in suspension culture with growth factor supplemented media using the method of Dontu et al. (Dontu, 2003). After 3 weeks, the single DCLK1+ sorted cells formed spheroids (FIGS. 20D, 20E); whereas DCLK1- sorted cells did not (data not shown). The spheroids containing 50 to 100 cells were mechanically dissociated and subsequently injected into contralateral flanks of nude mice. After 3 weeks nodular structures were observed (FIGS. 20F, 20G) in 11 of 12 spheroid injection sites (data not shown). Two weeks later, animals were sacrificed and nodules excised and subjected to immunohistochemical and histological analysis. In the control (MATRIGEL® injected) nodules, an inflammatory response was observed including the presence of macrophages, but with no evidence of epithelial cells (FIG. 20H). In the spheroid injected nodules however, there were single cells with oval nuclei and large nucleoli which lined up around central spaces and appeared to represent poorly formed glands (FIG. 20I). Cytokeratin 14 immunoreactivity demonstrates that these cells were of glandular epithelial origin (Moll et al., 2008; Purkis et al., 1990) (FIG. 20J). To determine whether they expressed stem and/or TA (progenitor) cell markers, the inventors stained for the epithelial stem/progenitor cell marker Msi-1 (Sureban et al., 2008; Potten, 2003). Significant Msi-1 immunoreactivity was observed in these epithelial structures providing additional support for the epithelial and perhaps stem/progenitor cell origin of these cells (FIG. 20K). Moreover, several cells expressed Math1 indicating an early intestinal epithelial secretory lineage commitment (goblet, enteroendocrine, and Paneth cells) (Yang et al., 2001; Shroyer et al., 2005) and L-type fatty acid binding protein (L-FABP) (marker of enterocyte lineage) (Rubin et al., 1992) (FIGS. 20L, 20M and 24). These studies demonstrate that DCLK1 can be used as a cell surface marker to isolate stem cells from the normal mouse intestine and investigate their lineage determination and viability in vivo.

Discussion of Example 3

In this Example, it has been demonstrated that the novel stem/progenitor markers DCLK1 and LGR5 identify intestinal stem and progenitor cells, respectively. This distinction is primarily based on the proliferative status of the cells, because no in vivo genetic lineage tracing studies have yet been performed for DCLK1. The major distinguishing feature presented here is that DCLK1 identifies a slowly cycling or basally quiescent cell; whereas LGR5 identifies a more proliferative cell. It is important to note that these classifications do not necessarily address the question of multipotency, as it is clear that an early intestinal progenitor cell is capable of repopulating the crypt with each of the four cell types expressed in the intestine (Crossman et al., 1994). This Example demonstrates that there may be two different populations of stem cells in the gut. One population is at or near the traditional +4 position, and is restricted primarily to the niche and may have a functional role in gut homeostasis and injury response. The second population is interspersed between the Paneth cells (CBCs) and may be responsible for Paneth cell repopulation in response to bacterial mediated injury.

These results have been supported by the recent report by Sangiorgi and Capecchi (Sangiorgi et al., 2008) identifying Bmi1 as yet another novel ISC marker. In that report using a knock-in transgenic mouse model, they presented data demonstrating that Bmi1 labels ISCs predominantly at the +4 position of the crypt. The authors suggest that Bmi1 and LGR5 label different states of ISCs. Bmi1 labels the more quiescent ISCs, while LGR5 labels ISCs more prone to enter proliferation (Sangiorgi et al., 2008). The results of this Example are further supported by reports that the putative stem/progenitor cell markers DCLK1, LGR5 and Msi-1 (Quante et al., 2008; Samuel et al., 2009; Humphries et al., 2008) are all expressed in CBC cells (Barker et al., 2007; May et al., 2008; Potten, 2003). One exciting outcome of this Example is the use of FACS for isolation of cells expressing DCLK1. Although originally considered to be a cytoplasmic protein (Giannakis et al., 2006), it has been reported that DCLK1 is expressed in adult brain with two transmembrane domains (amino acids 534-559 and 568-585), making it a cell surface expressing protein with intra and extracellular domains (Sossey-Alaoui et al., 1999; Kim et al., 2003). In this Example, cell surface isolation experiments confirm that DCLK1 is indeed expressed on the cell surface. Accordingly, anti-DCLK1 antibody was conjugated with ALEXA FLUOR® 568 (Life Technologies Corp., Grand Island, N.Y.) for use in cell sorting experiments. This Example demonstrated that putative stem cells isolated from the normal mouse intestine by FACS form spheroids in suspension culture, and upon injection into the flanks of nude mice form early glandular epithelial structures. Moreover, these cells expressed Msi-1 (Sureban et al., 2008; Potten, 2003), Cytokeratin 14 (Moll et al., 2008; Purkis et al., 1990), Math1 (Yang et al., 2001; Shroyer et al., 2005) and L-FABP (Rubin et al., 1992), markers of intestinal epithelial lineage.

The data presented in this Example demonstrate that LGR5+ and DCLK1+ cells are distinctly different and may even have different functions. However, it is predicted that both of these cell types are likely to have full multipotency and have the potential to regenerate a fully functional gastrointestinal tract following injury. The present Example demonstrates that for the first time these critical cell types can be identified in situ based on the discovery of these two novel markers. FIG. 25 presents a model for the specific expression patterns of the putative markers DCLK1, Msi-1 and LGR5 in the intestinal crypts.

The importance of reliable markers for identifying both stem and progenitor cells goes well beyond their use as a tool for sorting. The unique expression of DCLK1 in quiescent ISCs raises the question of whether functional quiescence is a requirement for gut homeostasis, and what factors regulate these processes. Identification of DCLK1 and LGR5 expressing cells will enable for the first time the direct examination of the gene expression profiles and molecular signatures of stem and progenitor cells, respectively.

Example 4

MicroRNAs (miRNAs) are small, non-coding RNAs that regulate gene expression in animal and plant systems (Lee et al., 2001; Lagos-Quintana et al., 2001). miRNAs have emerged as important developmental regulators and control critical processes such as cell fate determination and cell death (Bartel, 2004). There is increasing evidence that several miRNAs are mutated or poorly expressed in human cancers and may act as tumor suppressors or oncogenes (McManus, 2003; Takamizawa et al., 2004). Gene expression is regulated by miRNAs through complementary elements in the 3' untranslated regions (3'UTRs) of their target messenger RNAs (mRNAs) (Vella et al., 2004). lethal-7 (let-7), a founding member of the miRNA family, is required for timing of cell fate determination in C. elegans (Reinhart, 2000). In humans, various let-7 genes have been reported to map to regions that are deleted in human cancers (Calin, 2004). In addition, let-7 is poorly expressed in lung cancers (Takamizawa, 2004), suggesting that let-7 miRNAs may be tumor suppressors. In support of this, overexpression of let-7 inhibited cell growth of a lung cancer cell line in vitro (Takamizawa, 2004).

Mature miRNAs are produced from primary miRNA transcripts (pri-miRNAs) through sequential cleavages by the Microprocessor complex, comprising the ribonuclease III Drosha component and the double-stranded RNA (dsRNA) binding protein DGCR8 (Gregory, 2004) and Dicer (Chendrimada et al., 2005). This coordinated enzyme complex results in the release of pri-miRNA and mature miRNA species. Posttranscriptional control of miRNA expression has been reported to occur in a tissue-specific (Obernosterer et al., 2006) and developmentally regulated fashion (Viswanathan et al., 2008; Thomson et al., 2006). In mouse embryonic stem (ES) cells and in mouse embryonal carcinoma (EC) cells, the magnitude of the Microprocessor processing block is greatest for members of the let-7 family of miRNAs; although it is quite possible that the processing of all miRNAs may be regulated at the Microprocessor step (Viswanathan et al., 2008; Thomson et al., 2006). It has been recently discovered that in many cancers, the miRNA profile is altered when compared to normal tissue (Calin et al., 2006). It is becoming increasingly recognized that most cancers have a stem-cell-like compartment that is responsible for inciting and sustaining tumorigenesis (Calin et al., 2006; Jones et al., 2007). One might hypothesize that miRNA profiles are altered in cancer stem cells (CSCs) within a particular tumor. Moreover, it is quite possible that such alterations are key factors in the initiation of the CSC. Recent evidence suggests that several miRNAs may be responsible for maintaining stem-cell-like characteristics (Bussing et al., 2008; Hatfield et al., 2005).

Furthermore, miRNA profiling of human and mouse ES cells reveals high levels of miRNAs expression, previously associated with oncogenesis and cell-cycle control (Suh et al., 2004; Calabrese et al., 2007). Moreover, lack of let-7 miRNA expression was observed as an indicator for "stemness" in epithelial progenitor cells. Recent studies have also demonstrated that let-7 expression is absent in certain tumor cell lines, and that re-introduction of let-7 into these cells causes differentiation and reduction in proliferation and tumor-forming ability (Giannakis et al., 2006; May et al., 2008; Dekaney et al., 2005). The regulatory mechanisms that control the maturation process of miRNA are unclear and the regulatory factors that control let-7 miRNA levels, particularly in epithelial stem/progenitor cells, are completely unknown. The study of epithelial stem cell biology has been hampered by the lack of reliable stem cell markers that distinctly define and distinguish between stem and progenitor cell populations. There has been an accelerated interest, however, in defining these populations, as it is becoming increasingly clear that many important diseases including cancers are likely driven by effects on stem and/or progenitor cells.

Example 1 demonstrated that the novel putative intestinal stem cell marker DCLK1, a microtubule associated kinase expressed in post mitotic neurons (Lin et al., 2000) and in the stomach (Giannakis et al., 2006), is expressed in the intestine, colon and $Apc^{Min/+}$ adenomas (May et al., 2008). Given the importance of stem cells in mucosal regeneration and neoplasia, it was sought to determine whether DCLK1 played a functional role in tumorigenesis and whether these effects were mediated through regulation of let-7a miRNA.

Materials and Methods of Example 4

Cell culture. HCT116, HCT116 $p21^{-/-}$ and SW480 human colon adenocarcinoma cell lines were obtained from the American Type Culture Collection (ATCC) and grown in Dulbecco's modified eagle's medium (DMEM) supplemented with 10% fetal bovine serum and 100 U/mL penicillin-streptomycin in a humidified chamber at 37° C. with 5% $CO_2$.

Silencer RNA. DCLK1 siRNA (si-DCLK1) sequence targeting the coding region of DCLK1 ((GGGAGUGA-GAACAAUCUAC (SEQ ID NO:3), wherein the DCLK1 sequence is found in Accession # NM_004734 (SEQ ID NO:1)) and scrambled control siRNAs (si-Scr) not matching any of the human genes were obtained (Ambion Inc., Austin, Tex.) and transfected using TRANSFECTOL™ transfection kit (Ambion Inc., Austin, Tex.).

Real-time reverse transcription-PCR analyses. Total RNA isolated either from cells or from human colon cancer cell tumor xenograft samples was subjected to reverse transcription with SUPERSCRIPT® II RNase H—Reverse Transcriptase and random hexanucleotide primers (Invitrogen, Carlsbad, Calif.). The cDNA was subsequently used to perform real-time PCR by SYBR® chemistry (SYBR® Green I; Molecular Probes Inc., Eugene, Oreg.) for specific transcripts using gene specific primers and Jumpstart Taq DNA polymerase (Sigma-Aldrich, St. Louis, Mo.). The crossing threshold value assessed by real-time PCR was noted for the transcripts and normalized with β-actin mRNA. The changes in mRNA were expressed as fold change relative to control with ±SEM value.

Human primers used are:

```
β-actin:
                                        (SEQ ID NO: 4)
  Forward: 5'-GGTGATCCACATCTGCTGGAA-3'

(SEQ ID NO: 5)
  Reverse: 5'-ATCATTGCTCCTCCTCAGGG-3'

DCLK1:
                                        (SEQ ID NO: 6)
  Forward: 5'-AGTCTTCCGATTCCGAGTTGAG-3'

(SEQ ID NO: 7)
  Reverse: 5'-CAGCAACCAGGAATGTATTGGA-3' c-Myc:
                                        (SEQ ID NO: 8)
  Forward: 5'-CACACATCAGCACAACTACGCA-3'

(SEQ ID NO: 9)
  Reverse: 5'-TTGACCCTCTTGGCAGCAG-3'.
```

Mouse primers used are:

```
DCLK1:
                                       (SEQ ID NO: 10)
  Forward: 5'-CAGCCTGGACGAGCTGGTGG-3'

(SEQ ID NO: 11)
  Reverse: 5'-TGACCAGTTGGGGTTCACAT-3'.
``` miRNA analysis. Total miRNA was isolated using mir-Vana™ miRNA isolation kit (Ambion Inc., Austin, Tex.). Total miRNA isolated either from cells or from human colon cancer cell tumor xenograft samples were subjected to reverse transcription with SUPERSCRIPT® II RNase H—Reverse Transcriptase and random hexanucleotide primers (Invitrogen, Carlsbad, Calif.). The cDNA was subsequently used to perform real-time PCR by SYBR® chemistry (SYBR® Green I; Molecular Probes Inc., Eugene, Oreg.) for pri-let-7a transcript using specific primers and Jumpstart Taq DNA polymerase (Sigma-Aldrich, St. Louis, Mo.). The crossing threshold value assessed by real-time PCR was noted for pri-let-7a miRNA and normalized with U6 pri-miRNA. The changes in pri-miRNA were expressed as fold change relative to control with ±SEM value. Primers used are:

pri-U6:
(SEQ ID NO: 12)
Forward: 5'-CTCGCTTCGGCAGCACA-3'

(SEQ ID NO: 13)
Reverse: 5'-AACGCTTCACGAATTTGCGT-3' pri-let-7a:
(SEQ ID NO: 14)
Forward: 5'-GAGGTAGTAGGTTGTATAGTTTAGAA-3'

(SEQ ID NO: 15)
Reverse: 5'-AAAGCTAGGAGGCTGTACA-3'.

Western Blot analysis. HCT116 and SW480 cells were cultured in a 6 well plates to 40% confluency and were transfected with si-DCLK1 or si-Scr for 72 hours. Cells or the tumor xenograft samples were lysed and the concentration of protein was determined by BCA protein assay kit (Pierce Biotechnology Inc., Rockford, Ill.). Forty µg of the protein was size separated in a 7.5-15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 hour and probed overnight with a rabbit anti-DCLK1 antibody (Abcam Inc., Cambridge, Mass.) or with rabbit anti-c-Myc antibody (Santa Cruz Biotechnology Inc., Santa Cruz, Calif.). Subsequently, the membrane was incubated with anti-rabbit or anti-goat IgG horseradish peroxidase-conjugated antibodies (Amersham-Pharmacia, Piscataway, N.J.) for 1 hour at room temperature. The 82 kDa DCLK1 and 49 kDa c-Myc proteins were detected using ECL Western Blotting detection reagents (Amersham-Pharmacia). Actin (43 kDa), used as loading control was identified using a goat polyclonal IgG (Santa Cruz Biotechnology Inc.).

Immunohistochemistry. Heat Induced Epitope Retrieval was performed on 4 µm formalin-fixed paraffin-embedded sections utilizing a pressurized Decloaking Chamber (Biocare Medical Inc., Concord, Calif.) in citrate buffer (pH 6.0) at 99° C. for 18 minutes. (a) Brightfield: Slides were incubated in 3% hydrogen peroxide, then normal serum and BSA at room temperature for 20 minutes. After incubation with primary antibody DCLK1 C-terminal (Abcam Inc., Cambridge, Mass.), anti-c-Myc (Santa Cruz Biotechnology, Inc.), L-FABP (Santa Cruz Biotechnology, Inc.), the slides were incubated in peroxidase-conjugated EnVision™+ polymer detection kit (Dako, Carpinteria, Calif.). Slides were developed with Diaminobenzidine (Sigma-Aldrich, St. Louis, Mo.). (b) Fluorescence: Slides were first incubated in Image-iT FX signal enhancer (Invitrogen, Carlsbad, Calif.), followed by normal serum and BSA at room temperature for 20 minutes. After incubation with primary antibody (L-FABP (Santa Cruz Biotechnology, Inc.)), slides were incubated in appropriate ALEXA FLUOR® conjugated secondary (488 (green); Life Technologies, Grand Island, N.Y.).

Microscopic Examination. Slides were examined utilizing the Nikon 80i microscope and DXM1200C camera for brightfield. Fluorescent images were taken with PlanFluoro objectives, utilizing CoolSNAP™ ES2 camera (Photometrics, Tucson, Ariz.). Images were captured utilizing NIS-Elements software (Nikon Inc., Melville, N.Y.).

Stem cell isolation. Based on protocols developed in intestinal stem cell biology (Dekaney et al., 2005; Grossmann et al., 2003), stem cells were isolated from mouse intestine. The intestine was chopped into small strips, washed and incubated with 1 mM DTT (Sigma-Aldrich, St. Louis, Mo.) for 30 minutes at room temperature. It was further incubated with 30 mmol/L EDTA (Sigma-Aldrich, St. Louis, Mo.) for 10 minutes at 37° C. The strips were shaken vigorously in fresh HBSS (Mediatech, Inc., Manassas, Va.) and filtered through 400 µm mesh (SPECTRUM® Laboratories, Inc., Rancho Dominguez, Calif.) to separate the detached intestinal crypt epithelial cells from the tissue. The filtrate was passed through 80 µm mesh (BD Biosciences, San Jose, Calif.) to retain the crypts and washed. The crypts were digested at 37° C. to create a single cell suspension.

FACS. The cells isolated from mouse intestine were incubated with 1:100 dilution of ALEXA FLUOR® 568 (Life Technologies Corp., Grand Island, N.Y.) conjugated DCLK1 antibody (Abcam Inc., Cambridge, Mass.) for 30 minutes. The cells were washed twice with HBSS containing 10% serum and sorted using Influx-V cell sorter (Cytopeia Inc., Seattle, Wash.). DCLK1 positively and negatively sorted cells were collected and subjected to total mRNA and miRNA isolation. mRNA was reverse transcribed and subjected to real-time RT-PCR for DCLK1. Total miRNA was subjected to real-time RT-PCR for pri-let-7a miRNA.

Xenograft tumor model. (a) Liposomal preparation: siRNA was administered into the xenografts after incorporation into 1,2-Dioleoyl-sn-Glycero-3-Phosphocholine (DOPC) (Avanti Polar Lipids, Alabaster, Ala.). DOPC and siRNA were mixed in the presence of excess tertiary butanol at a ratio of 1:10 (w/w) (siRNA/DOPC). TWEEN® 20 (Sigma-Aldrich, St. Louis, Mo.) was added to the mixture at a ratio of 1:19 TWEEN® 20:siRNA/DOPC. The mixture was vortexed and frozen in an acetone/dry ice bath and lyophilized. Before administration, the siRNA preparation was reconstituted in 0.9% sterile saline and injected at a dose of 50 µl (5 µM) per injection. (b) Tumor therapy: Female athymic nude mice (NCr-nu) were purchased from the National Cancer Institute-Frederick Cancer Research and Development Center (Frederick, Md.) and housed in specific pathogen-free conditions. They were cared for in accordance with guidelines set forth by the American Association for Accreditation of Laboratory Animal Care and the USPHS "Policy on Human Care and Use of Laboratory Animals," and all studies were approved and supervised by the Institutional Animal Care and Use Committee. HCT116 cells ($6 \times 10^6$) were injected subcutaneously into the flanks of 4-6 week-old female athymic nude mice (5 mice per group). Tumors were measured with calipers and the volume was calculated as (length×width$^2$)×0.5. The tumors reached 1000 mm$^3$ after 15 days of injection of cells. These tumors were injected with 50 µl (5 µM) of siRNA preparation on every third day from day 15 for a total of 5 doses.

Luciferase reporter gene assay. pLet7a-Luc reporter vector contains a let-7a miRNA specific binding site at the UTR of the firefly (*Photinus pyralis*) luciferase gene obtained from Signosis Inc (FIG. 26). HCT116 and SW480 cells were transfected with the pLet7a-Luc reporter vector, *Renilla luciferase* expressing plasmid pRL-TK (Promega Corp., Madison, Wis.) along with DCLK1 or scrambled siRNA using TRANSFECTOL™ transfection kit (Ambion Inc., Austin, Tex.). Luciferase activity was determined as per the manufacturer's instructions (Dual-Luciferase Reporter Assay System; Promega Corp.) using a MONOLIGHT™ 2010 luminometer (Analytical Luminescence Laboratory, San Diego, Calif.) as described earlier (Stadler et al., 2008; Sossey-Alaoui et al., 1999). The activity, normalized to *Renilla luciferase* activity, is presented as relative luciferase units relative to control with ±SEM values. Assays were performed in triplicate wells and experiments were repeated 3 times.

Statistical analysis. All the experiments were performed in triplicate. The data was analyzed by Student's t-test. Where indicated, the data is presented as mean±SEM. A p value of <0.01 was considered statistically significant.

Results of Example 4

Figure 8:
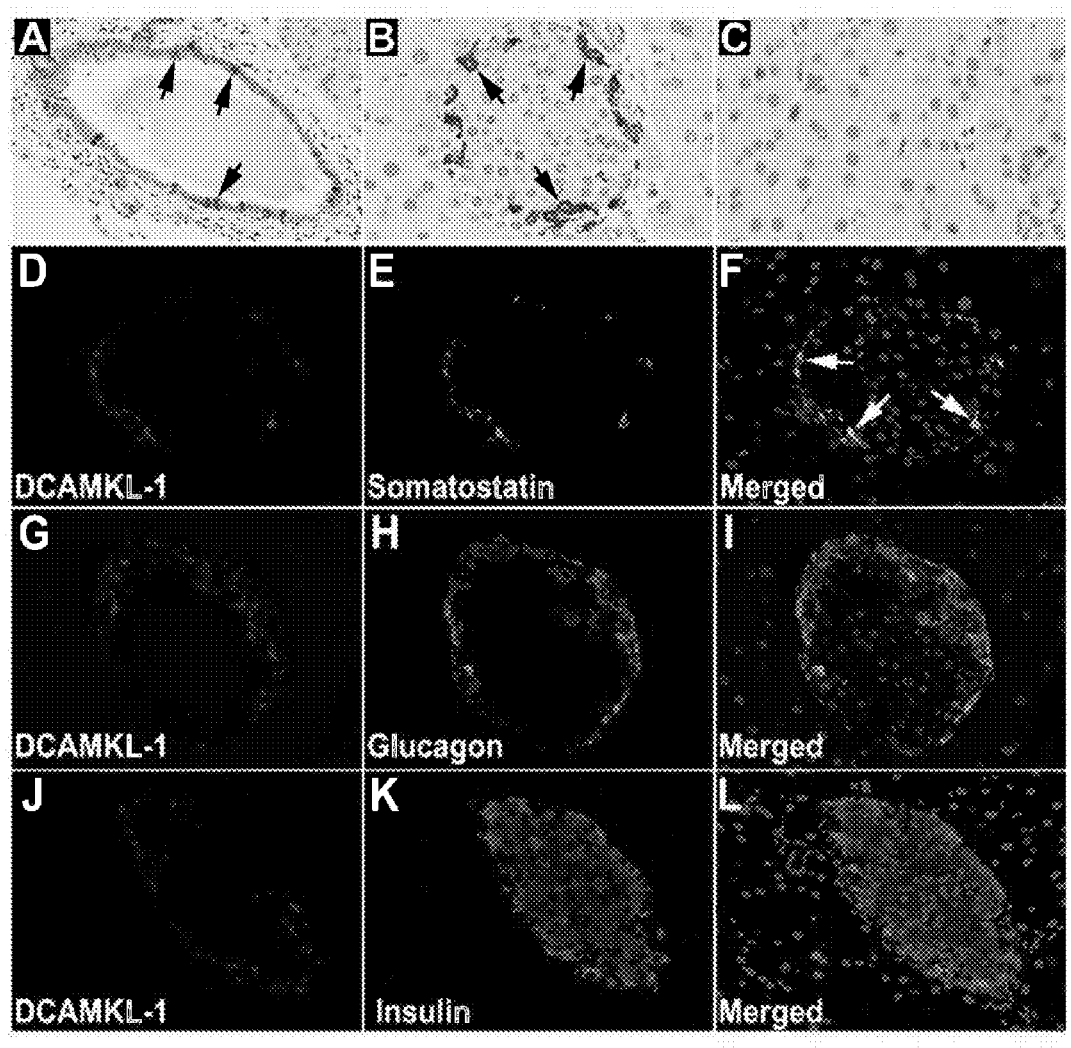

DCLK1 is overexpressed in cancer. To determine whether DCLK1 was expressed in human colorectal cancers, immunohistochemical analysis was performed on human cancer tissue microarrays (Tissue Array Network and National Cancer Institute—Tissue Array Research Program). Staining revealed increased DCLK1 protein (FIG. 27A; brown—indicated by black arrows) in human colorectal cancers specimens, compared to normal colonic mucosa. In tumors, the staining pattern was particularly impressive in the stroma surrounding malignant crypts (brown—indicated by blue arrow heads). Representative images of normal mucosa and two different human colorectal cancer specimens are shown in FIG. 27A. Similarly, DCLK1 expression was observed in a variety of human colon cancer cell lines (FIG. 27B). HCT116 and SW480 cells were transfected with DCLK1 and scrambled siRNA; then total RNA was isolated and subjected to real-time RT-PCR. A >70% reduction in DCLK1 mRNA expression was noted in DCLK1 siRNA (si-DCLK1) treated cells (FIGS. 27C and D). A reduction in DCLK1 protein was also observed following si-DCLK1 transfection (FIGS. 27C and D). Scrambled siRNA (si-Scr) did not affect the expression of DCLK1 mRNA or protein (FIGS. 27C and D).

siRNA mediated knockdown of DCLK1 leads to tumor growth arrest. Given the increased DCLK1 expression in human colorectal tumors (FIG. 27A) and in $Apc^{Min/+}$ adenomas (May et al., 2008), the inventors wanted to determine its role in tumor progression. Tumor xenografts were generated by injecting HCT116 cells ($6 \times 10^6$) subcutaneously into the flanks of athymic nude mice. After 15 days, si-DCLK1 and si-Scr were injected into the xenografts. Tumor volumes were measured using calipers at various time points before sacrifice and weights were determined after sacrifice (Sureban et al., 2008; Sureban et al., 2008A). Administration of si-DCLK1 resulted in a statistically significant reduction ($p<0.01$) in tumor size compared to the control or the si-Scr treated tumors (FIGS. 28A and 8). Thus inhibition of DCLK1 arrested HCT116 tumor xenograft growth. Total RNA isolated from these tumors was subjected to real-time RT-PCR and demonstrated a significant downregulation (55%) ($p<0.01$) of DCLK1 mRNA expression in the si-DCLK1-treated tumors compared to control and si-Scr treated tumors (FIG. 28C). This downregulation was associated with reduced expression of DCLK1 protein in those tumors by Western blot analyses (FIG. 28D).

Knockdown of DCLK1 induces pri-let-7a miRNA. To determine the role of DCLK1 mediated regulation of pri-let-7a miRNA, control and siRNA treated HCT116 tumor xenografts were analyzed for pri-miRNA expression by real-time RT-PCR. Compared to control and si-Scr treated tumors, there was a >3-fold increase in pri-let-7a miRNA expression in DCLK1 siRNA treated tumors (FIG. 29A). Next, the effects of siRNA-mediated knockdown of DCLK1 on pri-let-7a miRNA expression were analyzed in HCT116 and SW480 cells. Real-time RT-PCR analysis revealed a 4-fold increase in pri-let-7a miRNA, compared to controls (FIGS. 29B and C). These data demonstrate that DCLK1 negatively regulates pri-let-7a miRNA in human colon cancer cells.

DCLK1 negatively regulates let-7a miRNA. As stated earlier, lack of let-7 miRNA is an indicator of "stemness" in epithelial progenitor cells (Ibarra et al., 2007; Yu et al., 2007; Stadler et al., 2008). To determine whether pri-let-7a miRNA was expressed in stem cells, FACS based sorting was utilized to isolate DCLK1 positive and negative cells, which were analyzed for pri-let-7a miRNA. The antibody used for FACS was directed against the c-terminal extracellular domain of DCLK1 (Sossey-Alaoui et al., 1999; Kim et al., 2003) and conjugated to the ALEXA FLUOR® 568 fluorochrome (Life Technologies Corp., Grand Island, N.Y.). Following FACS, both sorted cell populations were examined by fluorescence microscopy. The positively sorted cells demonstrated the presence of DCLK1 antibody staining, whereas the negatively sorted cells did not (FIGS. 30A and B). Furthermore, DCLK1 positive cells did not express L-type fatty acid binding protein (L-FABP), a marker of enterocyte lineage known to be expressed in differentiated intestinal epithelia (Rizvi et al., 2005; Smith et al., 1996), indicating a less differentiated state (FIGS. 30C and E). In contrast, L-FABP was found to be expressed in DCLK1 negative cells (FIGS. 30D and F), indicating that these cells are more differentiated compared to DCLK1 positive cells.

Total miRNA isolated from DCLK1 positive and DCLK1 negative cells were subjected to pri-let-7a miRNA expression by real-time RT-PCR and normalized using pri-U6 miRNA. A 65% reduction in pri-let-7a miRNA was observed in DCLK1 positive sorted "stem" cells relative to DCLK1 negative cells (FIG. 31A). To confirm sorting specificity, total RNA isolated from the cells was subjected to real-time RT-PCR for DCLK1 mRNA expression (FIG. 31B). These data demonstrate that DCLK1 negatively regulates pri-let-7a miRNA in putative intestinal stem/progenitor cells.

To determine quantitatively the effect of siRNA-mediated knockdown of DCLK1 on let-7a miRNA, a luciferase reporter gene assay was performed. HCT116 and SW480 cells were transfected with a plasmid containing firefly luciferase gene with a complementary let-7a binding site at the UTR (FIG. 26). A dose dependent reduction in luciferase activity was observed following the knockdown of DCLK1 (FIGS. 31C and D). This demonstrates that DCLK1 may be a posttranscriptional regulator of let-7a miRNA downstream targets. However, other alternative mechanisms for DCLK1, such as acting as a transcriptional regulator of let-7a or as a posttranscriptional regulator of let-7a maturation, cannot be ruled out.

Knockdown of DCLK1 inhibits c-Myc. HCT116 tumor xenografts were evaluated for expression of the let-7a miRNA downstream oncogenic target c-Myc, following siRNA-mediated knockdown of DCLK1 as described earlier. A 45% reduction in c-Myc mRNA was observed in si-DCLK1 treated tumors compared to controls (FIG. 32A). An even more striking reduction of c-Myc protein was seen by Western blot and immunohistochemical analyses (FIGS. 32B and C) of siDCLK1 treated tumors. A significant reduction in c-Myc mRNA and protein was also observed in siDCLK1 treated HCT116 (FIGS. 32D and E) and SW480 cells (FIGS. 32D and F). These data suggest that knockdown of DCLK1 results in a reduced expression of c-Myc by a let-7a dependent mechanism.

Discussion of Example 4 miRNAs play important gene-regulatory roles by pairing to the mRNAs of protein-coding genes to direct their posttranscriptional repression (Kumar et al., 2007). The involvement of miRNAs in human cancer has been recently described (Calin et al., 2006) with several reports indicating that miRNAs might be used as future diagnostic and therapeutic targets (Tricoli et al., 2007). Furthermore, characteristic miRNA expression signatures in various cancers that can profoundly affect cancer cell behavior have been reported (Calin et al., 2006). miRNAs have been shown to play an important role in regulating stem cell self-renewal and differentiation by repressing the translation of selected mRNAs in stem cells and differentiating daughter cells. Let-7a is a tumor suppressor miRNA that is blocked posttranscriptionally in ES cells and in several human cancers (Thomson et al., 2006; Calin et al., 2006; Suh et al., 2004). The regulatory factors that control miRNA expression, maturation and function in adult stem cells and cancers are just beginning to be explored.

This Example demonstrates that the novel putative intestinal stem cell marker DCLK1 is a negative regulator of let-7a miRNA expression/function. Here it is demonstrated that DCLK1 expression is increased in human colorectal cancers compared to normal uninvolved tissues. This is the first demonstration of DCLK1 in human colorectal cancer. In addition to the increased epithelial expression of DCLK1 seen within the colorectal tumors examined, strong staining was also observed in the stroma surrounding malignant crypts. Given the importance of epithelial-mesenchymal cell interactions in cancer (Arias, 2001) and the role of the niche in epithelial stem cell fate (Rizvi et al., 2005), it is speculated that stromal DCLK1 may participate in tumor progression.

Using a tumor xenograft model generated from HCT116 human colorectal cancer cells, near complete tumor growth arrest was demonstrated following siRNA-mediated knockdown of DCLK1. These data strongly implicate a functional role for DCLK1 in the regulation of tumor growth. Given the potential roles of let-7a miRNA in the regulation of gene expression in stem cells and cancer, the tumor xenografts were assayed for pri-let-7a miRNA expression. A significant increase in pri-let-7a miRNA was found in the tumors following siRNA-mediated inhibition of DCLK1. These data confirm that pri-let-7a miRNA is indeed a tumor suppressor miRNA, which is regulated by DCLK1 in colorectal cancer cells.

Cellular transformation and tumorigenesis are driven by activation of oncogenes and/or inactivation of tumor suppressors. Oncogenic c-Myc overexpression is observed in many cancers along with enhanced cell proliferation (Smith et al., 1996). Furthermore, transcripts encoding both c-Myc and Kras are known to contain target sites for the let-7 miRNA in their 3'UTR (Kumar et al., 2007). Such findings led us to speculate that DCLK1 may affect c-Myc expression in colon cancer via a let-7a dependent mechanism. Indeed, a 45% reduction in c-Myc mRNA was found, as well as a significant decrease in protein levels in the tumors following the inhibition of DCLK1. These findings were confirmed in vitro in human colorectal cancer cell lines where knockdown of DCLK1 resulted in increased pri-let-7a miRNA, which corresponded with a significant reduction of c-Myc. These data taken together strongly suggests that DCLK1 negatively regulates the tumor suppressor miRNA let-7a resulting in reduced expression of its downstream target oncogene c-Myc.

In order to determine the effects of DCLK1 knockdown on let-7a miRNA-dependent gene silencing of let-7a downstream targets, a luciferase gene reporter assay containing a specific let-7a miRNA binding site at its 3'UTR was performed. A significant dose-dependent reduction in luciferase activity was found following knockdown of DCLK1. This provides an explanation and mechanism where inhibition of DCLK1 results in decreased c-Myc and possibly other let-7a downstream targets.

In this Example, it has been demonstrated that DCLK1, a protein expressed in both normal stem cells and in cancer, likely promotes tumorigenesis through the regulation of pri-let-7a miRNA and c-Myc. The presence of let-7a binding sites in the c-Myc 3'UTR leads us to speculate that DCLK1 is regulating c-Myc posttranscriptionally. However, other alternatives cannot be ruled out, such as direct transcriptional regulation. Nevertheless, the knockdown of DCLK1 resulted in a marked reduction in c-Myc mRNA and protein in vitro and in vivo. Moreover, several other oncogenes contain let-7a binding sites in their 3'UTRs, thus it is quite possible that DCLK1 may have similar effects on other oncogenic targets including Kras.

miRNAs are known to contribute to the preservation of 'stemness' and associated with self-renewal and differentiation in ES cells (Shcherbata et al., 2006). Previous studies have also shown an overall reduction in miRNA expression in embryonic and tissue stem cells (Croce et al., 2005). Intestinal epithelial cells were analyzed following FACS based sorting using DCLK1 for pri-let-7a miRNA. A marked reduction in pri-let-7a miRNA was observed in DCLK1 positively sorted "stem" cells relative to DCLK1 negative cells. These data demonstrate that intestinal stem cells, like ES cells, express low levels of let-7a.

The findings presented in this Example demonstrate that regulation of miRNAs represent an exciting new strategy to combat tumorigenesis, particularly in cancers originating from cancer stem cells.

Example 5

As shown in Examples 1-3, DCLK1 is a putative intestinal and pancreatic stem cell marker and is overexpressed in various cancers (colorectal, pancreatic, breast, liver, and prostate). Example 4 demonstrated that siRNA-mediated knockdown of DCLK1 in colorectal and pancreatic cancer cells results in tumor xenograft growth arrest, and that knockdown of DCLK1 induces tumor suppressor siRNA-mediated miRNA Let-7a and subsequent down regulation of oncogenes c-Myc and KRAS.

Knockdown of DCLK1 has been shown to induce miRNA miR-200a (an epithelial to mesenchymal transition (EMT) inhibitor) via down regulation of EMT transcription factors ZEB1, ZEB2, Snail, Slug and Twist (Sureban et al., 2011a and 2011b). siRNA-mediated knockdown of DCLK1 was also shown to induce miR-144 and downregulate its downstream target Notch-1. REG4 is overexpressed in various GI cancers (Bishnupuri et al., 2006; and Zenilman et al., 1997). REG 4 may play an important role in initiating colorectal adenoma, and it is a potential biomarker for early diagnosis of colorectal cancers.

In this Example, it is demonstrated that treatment with a monoclonal antibody against DCLK1 caused downregulation of multiple oncogenic pathways (e.g., c-Myc, KRAS, and Notch-1) in human pancreatic cancer cells. In addition, an upregulation of tumor suppressor microRNAs (let-7a, miR-200a, and miR-144) was observed following treatment of the human pancreatic cancer cells with the monoclonal antibody against DCLK1. Monoclonal antibody treatment against critical targets such as DCLK1 provides a novel approach to treat cancer through the regulation of endogenous tumor suppressor miRNAs.

Materials and Methods for Example 5

Ab484 (also referred to as Anti-Estrogen Receptor alpha antibody (1F3)) was purchased from Abcam Inc. (Cambridge, Mass.). AsPC1, human pancreatic cancer cell lines were treated with Ab484 (monoclonal antibody against DCLK1) (50 µg/mL) alone or in combination with Pep-799 (Neutralizing peptide or peptide used to raise the monoclonal antibody) (50 µg/mL) for 48 hours. Total RNA isolated from these treated cells was subjected to real-time RT-PCR for mRNA analysis using SYBR® green chemistry (Molecular Probes Inc., Eugene, Oreg.).

In the pancreatic cancer cell line AcPC1, the Ab-484 monoclonal antibody against DCAMKL1 caused down regulation of DCAMKL1 mRNA, c-Myc, KRAS, Notch-1, ZEB1, Msi-1, BMI1, and REG4, as shown in FIG. 33. In addition, Ab-484 caused upregulation of Let-7a miRNA, miR-144, and mIR-200a, as shown in FIG. 34.

Treatment with monoclonal antibody against DCLK1 resulted in downregulation of protooncogenes c-Myc and Notch-1 via let-7a and miR-144 miRNA-dependent mechanisms, respectively, in AsPC-1, a human pancreatic cancer cell line. Moreover, an upregulation of EMT inhibitor miR-200a and downregulation of the EMT-associated transcription factor ZEB1 was observed. These findings illustrate direct regulatory links between DCLK1, microRNAs, and EMT in pancreatic cancer and other cancers. Moreover, they demonstrate a functional role for DCAMKL-I in pancreatic cancer. Together, these results demonstrate that DCLK1 is a viable therapeutic target for eradicating solid tumor cancers.

Example 6

To produce another DCLK1 monoclonal antibody, peptides were generated against two regions of the C-terminus of DCLK1 Isoform: amino acids 700-729 (SEQ ID NO:20; also referred to herein as COARE-CT)) and amino acids 680-709 (SEQ ID NO:21; also referred to herein as COARE-709). FIG. 35 contains a sequence alignment showing the region of overlap between DCLK1 isoform 1 (amino acids 661-729 of SEQ ID NO:2) and both peptides. FIG. 35 also contains a 3D structure of the DCLK-short-β isoform showing peptide 700-729 in red, peptide 680-709 in blue, and the region of overlap in purple.

Screening of Sera: Mice were immunized with either peptide (COARE CT or 709), and the serum from the immunized mice was used to perform western blots using varying lysates, as shown in FIG. 36. Serum that was able to detect both DCLK1 isoform types was selected for hybridoma production. Following hybridoma production, cell culture supernatant from the hybridomas was screened against various lysates and shown to detect both DCLK1 long and short isoforms (FIG. 37). The best clones were selected for final antibody production and cell line maintenance. Hybridoma clone 4B5B3 cells were cultured and expanded into roller bottles with 2 liter hybridoma culturing medium without fetal bovine serum. Monoclonal Ab 4B5B3 was purified through a Protein G affinity column from the cultured medium. The effect of this mAb was then tested.

Figure 41:
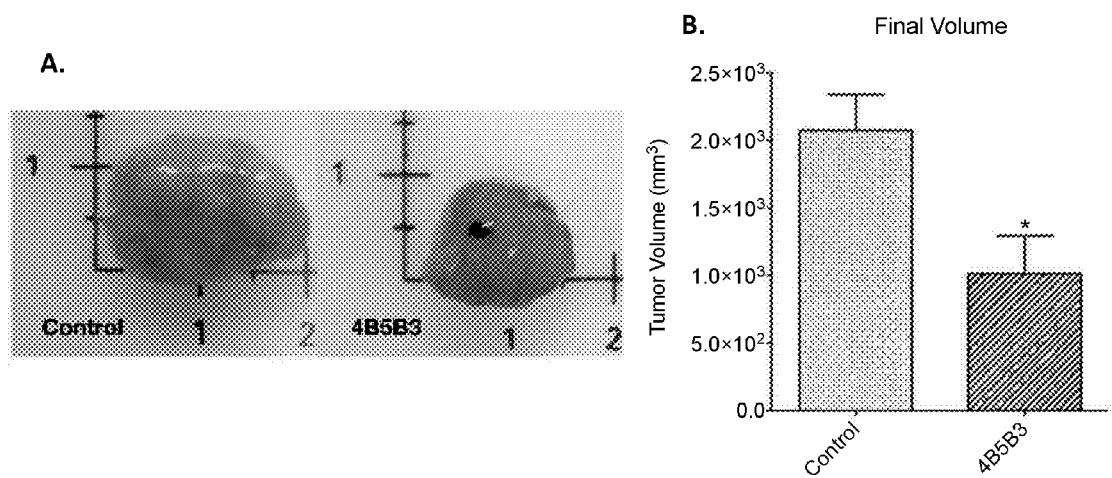

One DCLK1 mAb (4B5B3) was selected for determination of therapeutic effect and characterized in vitro and in vivo. FIGS. 38-39 illustrate the in vitro characterization of 4B5B3, while FIGS. 40-41 illustrate the in vivo characterization thereof. For in vitro characterization, $1 \times 10^5$ AsPC-1 pancreatic cancer cells were seeded into each well of a 6-well dish and allowed to attach overnight. The following day, cells were treated with vehicle (Mops Buffer) or 4B5B3 mAb (50 µg/ml). Twenty four hours post treatment, the cells were lysed with tri-reagent, total RNA was isolated, 1st strand cDNA was synthesized, and real-time RT-PCR was performed using β-actin (mRNA) or U6 (miRNA) for normalization. As shown in FIGS. 38 and 39, the 4B5B3 mAb demonstrated therapeutic effects in vitro, including downregulation of the key oncogenic factors NOTCH1, MYC, KRAS, as well as downregulation of prominent EMT factors (FIG. 38). Additionally, a significant 2-fold upregulation of tumor suppressor miRNA Let-7a was observed (p=0.0001).

For in vivo characterization of the 4B5B3 mAb, immunodeficient nude mice were injected in the flanks with $0.5 \times 10^6$ HCT116-DCLK1-GFP colon cancer cells, which overexpress DCLK1 and show increased proliferative and invasive properties in vitro. As soon as the tumors reached a volume of 100 mm$^3$, the mice were injected peritumorally with either 4B5B3 mAb (1 mg/kg) or vehicle once per week. Tumor measurements were taken approximately every 3rd day. At day 20, the mice were culled, tumors were excised and measured, and the data was compiled and analyzed by ANOVA. The 4B5B3 mAb significantly inhibited growth of the HCT116-DCLK1 tumor xenografts (p=0.049), as shown in FIG. 40. The 4B5B3 treated tumors also showed a significant decrease in final volume (p=0.0457), as shown in FIG. 41, and the volume difference was visible in the excised tumors; a 50% average reduction in excised tumor volume was found in the 4B5B3 treated mice (FIG. 41A). The representative images of FIG. 41A were chosen by selecting whichever tumor from each group was closest in volume to the average for that group. Thus, the 4B5B3 antibody has demonstrated therapeutic effects against colon and pancreatic cancer, and this characteristic will enhance the efficacy of ADCs generated with this antibody.

Example 7

In FIG. 42, AsPc1 cells were treated with Ab-484, a competitive DCLK1 peptide 799, or with both the antibody and the competitive peptide. The effect of the antibody and/or competitive peptide on mRNA expression levels of various genes was then determined and compared to control mRNA levels in the absence of antibody or peptide.

Several genes were down-regulated in the presence of Ab-484, including c-Myc, NOTCH1, REG4, ZEB1, and ZEB2. In addition, other genes were up-regulated by Ab-484, including let7a, miR200a, and miR144. Addition of the DCLK1 peptide 799 competed for antibody binding and abolished these effects; this demonstrates that this effect of upregulation of certain genes and down-regulation of others is specific for DCLK1.

Example 8

In this Example, the novel cancer stem cell line CSRD1 was developed. This cell line provides an invaluable tool in the study of cancer stem cell biology. CSRD1 cells share the molecular characteristics of human RSCs, grown in standard tissue culture, are resistant to standard therapy, and form tumors in isografts. Therefore, this cell line can be used to screen small-molecule drugs for their effect on tumor stem cells, and the most efficient can be conjugated to an anti-DCLK1 antibody, as described in detail in later Examples.

DCLK1 in mouse pancreatic ductal adenocarcinoma models: The endogenous pancreatic cancer mouse model P48$^{cre}$-LSL-Kras$^{G12D}$ develops PanIN lesions (similar to humans) after 10 weeks, and 70-85% develop carcinoma with metastasis at 9 months (Roa et al., in AACR 100$^{th}$ Annual Meeting 2009, Denver, Colo., 2009). Pancreatic tissues from 10 month old P48$^{cre}$-LSL-Kras$^{G12D}$ were immunostained for DCLK1. An increase in ductal expression of DCLK1 was observed in the PanIN lesions of the P48$^{cre}$-LSL-Kras$^{G12D}$ pancreatic cancer mouse model that correlated with progressive neoplastic changes (FIG. 43). These data demonstrate that DCLK1 upregulation following mutant Kras mediated tumorigenesis may represent a marker of neoplastic transformation. More recently, it has been demonstrated that introducing the Kras$^{G12D}$ mutation into DCLK1-expressing cells leads to rapid onset of PanIN lesions and PDAC in a mouse model (DCLK1-Cre-ERT; LSL-Kras$^{G12D}$), demonstrating that DCLK1 marks pancreatic cancer initiating cells.

DCLK1 in human pancreatic adenocarcinoma: In order to determine if DCLK1 was associated with human PDAC, tumor and matching normal tissue were obtained from patients undergoing resection at the University of Oklahoma Health Sciences Center (Oklahoma City, Okla.). Total RNA was isolated from the tissue samples, and real-time RT-PCR was performed to assess DCLK1 mRNA expression. DCLK1 levels were found to be significantly upregulated in tumors. Immunohistochemical staining of the tumor tissue was scored by a pathologist and revealed that DCLK1 ductal protein expression was significantly correlated with PanIN lesions in a stage-wise manner, while staining in normal tissue was sparse to non-existent (FIG. 44). Given these results, the effect of knocking down DCLK1 in AsPC-1 human pancreatic cancer cells was assessed. It was found that siRNA-mediated downregulation of DCLK1 results in significant downregulation of EMT genes ZEB1, ZEB2, SNAI1, SNAI2, and TWIST with a correlating increase in CDH1 (E-cadherin) expression. Moreover, both mRNA expression analysis and luciferase assays revealed that the oncogene KRAS was significantly downregulated, and tumor-suppressor miRNA Let-7a was significantly upregulated. These results demonstrate that targeting DCLK1+ cells with therapeutics will likely avoid damage to the normal pancreas, and that loss of DCLK1 expression promotes loss of EMT and oncogenic characteristics.

Characterization of the CSRD1 cell line: In order to generate a model tumor stem cell line, DCLK1 was overexpressed in NIH3T3 mouse embryonic fibroblast cells. Subsequently, the cell line was sorted by FACS using α-DCLK1 in order to obtain a purified DCLK1 overexpressing cell population (CSRD1). Overexpression of DCLK1 was confirmed by mRNA and protein analysis. These cells demonstrated significant upregulation of stemness factors Pou5f1 (Oct4), Nanog, Sox2, Myc, Lgr5, and Notch1 and loss of master tumor suppressor miRNA Let-7a (FIG. 45A). In order to assess the tumorigenic potential of the CSRD1 cell line, 2×10$^6$ CSRD1 or NIH3T3 (control) cells were injected subcutaneously into NOD/SCID mice. After 2 months, tumors formed in the CSRD1-injected mice (FIG. 45B) and grew rapidly such that they had to be euthanized within weeks to maintain compliance with the mouse protocol, which did not allow for growths larger than 20% of the size of the mouse. No tumors formed in the control mice. These results demonstrate that overexpression of DCLK1 promotes stemness and enables tumorigenesis in normal cell lines.

Example 9

The primary purpose of this Example is to develop novel antibody drug conjugate (ADC) platform technologies that directly target tumor stem cells (TSCs) within solid tumors. TSCs comprise a minority subpopulation of highly tumorigenic neoplastic cells within tumors and are relatively resistant to standard therapy. TSCs self-renew, differentiate, and regenerate the original tumor when implanted into immunodeficient mice. TSCs have been identified and isolated in a wide variety of cancers, including but not limited to, breast, pancreas, and colon. This Example is based on the identification that tumor stem/progenitor cells are a key subset of solid tumors in colorectal and pancreatic cancers, and the inventive concept(s) that targeted delivery of drug payloads to tumor stem cells is critical for tumor eradication and treatment of recurrent disease.

One major obstacle to enabling targeting of tumor stem cells in colorectal and pancreatic cancers has been the lack of a definitive marker which specifically identifies these cells. It has been demonstrated previously herein that doublecortin-like kinase 1 (DCLK1) is overexpressed in human and animal models of pancreatic and colorectal cancers, and can be used to isolate and characterize putative tumor stem cells. The identity of the DCLK1$^+$ cell as a specific tumor stem cell in colorectal cancer has been confirmed herein in the Apc$^{min/+}$ mouse model of intestinal neoplasia. Moreover, inducible deletion of this cellular population has been shown to result in loss of adenomas without any apparent damage to the normal intestine. New technologies that are able to shuttle cytotoxic agents directly to these DCLK1$^+$ TSCs have strong potential to improve cancer treatment. Thus, this Example is directed to (1) the utilization of a novel tumor stem cell model for in vitro and in vivo drug development; (2) the isolation of tumor stem cells within accepted mouse models of pancreatic and colorectal cancer; and (3) the targeting of model TSCs and isolated TSCs with this novel antibody drug conjugate technology. The purposes of this example are listed in the following paragraphs.

Purpose A: Screening of small-molecule drugs for induction of cell death using a novel tumor stem cell line, and preparation of TSC-specific antibody-drug conjugates from the most promising agents. A novel proprietary system has been developed that combines transformation of immortalized non-tumorigenic cell lines followed by FACS based sorting using the novel TSC marker DCLK1. These cells exhibit vastly increased expression of pluripotency factors, loss of tumor-suppressor miRNAs, and resistance to drug treatment. When injected into NOD/SCID mice, these cells, termed CSRD1, rapidly develop tumors. A screen for small-molecule drugs that demonstrate an ability to kill CSRD1 cells is performed, and the most efficient drugs are conjugated to an anti-DCLK1 antibody as described herein above, such as but not limited to, the 4B5B3 antibody that targets the extracellular C-terminus of the TSC-specific protein DCLK1. The resulting conjugates are tested in vitro and in vivo against CSRD1 cell lines and isografts.

Purpose B: Determining the efficacy of antibody-drug conjugate driven targeted depletion of TSCs, using cells derived from animal models of neoplasia. TSCs from mouse tumors are isolated using DCLK1-based FACS sorting, and the efficacy of prototype stem-cell targeted ADCs on individualized TSC derived tumors is determined in vitro and in vivo. Apc$^{min/+}$ mice, which spontaneously develop hundreds of intestinal adenomas by 20 weeks of age on a high fat diet, and Pdx$^{cre}$-LSL-Kras$^{G12D}$-P53$^{flox}$ (KPC) mice, which develop pancreatic adenocarcinoma with PanIN lesions consistent with human disease, are used. Candidate ADCs prepared in (A) are evaluated quantitatively on animal model TSC fate with in vivo isotransplantation assays. Candidate ADCs that demonstrate positive results in these assays are tested against the parent mouse line to assess general therapeutic efficacy.

The development of highly specific ADC platforms for anti-TSC based drug development provides agents that effectively delete, inactivate, or suppress tumor stem cell function. An improved mechanism to identify and perform preclinical testing of promising agents will accelerate the drug development process.

The idea of delivering drugs to tumor antigens with monoclonal antibodies (mAb's) has been around since the 1980s. However, until recently there has been little success in this field. Past clinical failures have resulted from the use of unstable linking molecules in conjugation and the targeting of antigens that were highly expressed not only in the tumor but also in healthy normal tissue. The purpose of this Example is to target a specific tumor stem cell with a novel proprietary monoclonal antibody conjugated to new or existing therapeutic cytotoxic payloads using a proprietary conjugation platform. Using this platform, new drugs are developed that overcome specific obstacles that have hindered effective solid tumor cancer therapies. Moreover, the specificity of TSC targeting avoids damage to local normal tissue while activating multiple anti-cancer pathways within the tumor itself. Internalization of cytotoxic payloads allows for the use of otherwise toxic agents that would be unsafe without this enhanced tumor stem cell targeting platform. Taken together, these characteristics demonstrate a therapeutic profile that includes enhanced efficacy, decreased side effects, and potentially the prevention of disease recurrence.

Although many ADCs are currently in clinical trials, only three have been approved by the FDA. Two of those drugs, ADCETRIS® (brentuximab vedotin, Seattle Genetics, Inc., Bothwell, Wash.) and MYLOTARG® (gemtuzumab ozogamicin, Wyeth LLC, Madison, N.J.) were developed to target cells expressing CD30 and CD33 antigens in blood cancers (acute myeloid leukemia and forms of lymphoma). Pfizer voluntarily removed MYLOTARG® from the market in response to the results of post-approval studies demonstrating no gain in life expectancy and increased risk of death. The latest advancement in ADC technology came from a partnership between pharmaceutical firms Immunogen and Genentech. In February 2013, their drug KADCYLA® (ado-trastuzumab emtansine, Genentech, Inc., San Francisco, Calif.) was approved for the treatment of metastatic HER2-positive breast cancer, making it the first ADC to be approved for the treatment of a solid tumor cancer. KADCYLA® is composed of therapeutic HER2 antibody TRASTUZUMAB® (Genentech, Inc., San Francisco, Calif.) and maytansinoid cytotoxin mertansine bound with the common linking reagent sulfosuccinimidyl-4-(N-maleimidomethyl)cyclohexane-1-carboxylate (SMCC). This simplistic yet elegant ADC has shown highly positive results in clinical trials of patients with HER2-positive breast cancer, including reducing cancer recurrence by 50% and mortality by 30%. These successful results can be attributed to targeting an antigen that is specifically upregulated in tumor tissue (HER2) and the use of a non-cleavable linker, both of which prevent off-target toxicity from unintended delivery of cytotoxin to normal cells.

Many major pharmaceutical and biotechnology companies are involved in the drug development process, as it is essential for the generation of new and improved therapies for diseases that afflict millions of people worldwide. Billions of dollars are invested every year to develop new drugs, but very few candidate drugs ever make it to clinical trials or to market. This emphasizes the need to develop early testing strategies that increase the likelihood that a compound will have efficacy at the later stages of the drug development process.

This Example provides a novel strategy of specifically targeting tumor stem cells that has several benefits over traditional anticancer drug development: (1) demonstration of in vitro screening assays that correlate with in vivo assays reduces the time and costs involved in identifying suitable compounds for targeting TSCs; (2) creation of a malleable targeted delivery platform allows pharmaceutical companies to deliver drugs directly to TSCs, thereby targeting the root cause and cellular processes that initiate and sustain tumor growth; and (3) the ability to rapidly synthesize novel ADCs that have therapeutic potential based on these screening and targeting technologies. In summary, the drug development process is a high-risk proposition and involves a huge investment of money and time. Traditionally, many compounds that are screened initially fail to make it to the next stage of development thereby increasing the cost. The creation of a novel proprietary targeting platform that provides payload flexibility and increases the likelihood of successful drug development ultimately reduces the cost, risk, and time required to create, test, and market lifesaving anti-cancer drugs.

There is a series of preliminary studies and literature data that support DCLK1 as a novel putative stem cell marker that can be used to develop a tumor stem cell targeting platform. These studies/data include the following observations. (1) DCLK1 cell surface expression allows for FACS based isolation and targeting of stem cells. (2) DCLK1 selectively marks tumor stem cells in $Apc^{min/+}$ adenomas. (3) Inducible ablation of $DCLK1^+$ cells in $Apc^{min/+}$ mice results in loss of adenomas. (4) DCLK1 is highly expressed in $Apc^{min/+}$ adenomas and colocalizes with Lgr5 and nuclear β-catenin. (5) DCLK1 is expressed at low levels in the normal intestine. (6) $DCLK1^+$ cells isolated from $Apc^{min/+}$ adenomas form spheroids and demonstrate increased stemness. (7) DCLK1 expression is increased in human colon cancer. (8) Overexpression of DCLK1 increases HCT116 colon cancer cell proliferation and invasion. (9) siRNA mediated knockdown of DCLK1 results in HCT116 colon cancer tumor growth arrest. (10) Introduction of the $Kras^{G12D}$ mutation into $DCLK1^+$ cells initiates pancreatic cancer in mice. (11) DCLK1 is upregulated in the $P48^{Cre}$-LSL-$Kras^{G12D}$ pancreatic cancer mouse model. (12) DCLK1 expression correlates to PanIN progression. (13) DCLK1 expression is increased in human PDAC tissue. (14) DCLK1 expression is low in the normal pancreas. (15) Overexpression of DCLK1 in non-tumorigenic cell lines (CSRDs) results in molecular changes consistent with TSCs. (16) CSRD1 cells injected into nude mice form aggressive tumors. (17) Monoclonal antibody 46563 against the C-terminus of DCLK1 limits HCT116 tumor xenograft growth.

Most current anti-cancer therapies are directed towards rapidly dividing cells. Stem cells however, for the most part are not rapidly dividing and in many cases are quiescent. Thus, most standard chemotherapy agents will not be sufficient to kill these cells, which may explain why current treatments do not cure cancer or prevent recurrence. Agents that target tumor stem cells may have significant therapeutic efficacy because they should leave the normal tissues surrounding the tumor and the rest of the body relatively unharmed. The addition of a TSC-specific targeting antibody should contribute further towards negating off-target toxicity.

The identification of a marker that is expressed primarily in quiescent cells within the normal gastrointestinal tract and overexpressed in tumors allows definitive targeting of stem cells. The recent study demonstrating that the $DCLK1^+$ cell lineage is responsible for the formation of adenomas and that ablation of this cell population results in loss of adenomas with no apparent negative effects on the normal intestine supports this targeting strategy in colon cancer.

Furthermore, the highly increased expression of DCLK1 protein in human colon and pancreatic cancers enhances the targeting specificity of this platform in general. The generation of the tumorigenic CSRD1 cell line that recapitulates the molecular characteristics of human TSCs provides a unique platform for screening therapeutics. Development of ADCs that can eradicate or inactivate TSCs provides a novel therapeutic approach to cancer therapy either as standalone agents or in conjunction with traditional therapies.

In order to meet Purpose 1 of this Example and screen for compounds that can eradicate TSCs, a structured, low-throughput approach is employed. A drug library of approximately 1500 bioactive compounds (Selleck Chemicals, Houston, Tex.) is purchased. This library is chemically diverse and includes known and novel cytotoxins, chemotherapeutics, epigenetic modulators, natural products, and inhibitors, all of which are bioactive and demonstrate cell permeability. The assay has three primary stages: (1) live/dead viability assays; (2) MTT proliferation assays; and (3) further molecular and morphological characterization.

In stage 1, CSRD1 cells are plated in 96-well plates at 5000 cells/well and allowed to attach overnight. The cells are then treated with various concentrations of drug. The low threshold of the screening is set at 1 nM concentration of drug, and the high threshold is set at 10 µM. Because the use of targeted delivery is particularly desired, the primary focus is on hits that affect cell viability at very low concentrations (i.e. 1-100 nM). After the cells have been exposed to drug for 24 hours, live/dead assays are performed on a microplate reader using LIVE/DEAD® cytotoxicity/viability reagents (Life Technologies Corp., Grand Island, N.Y.). These reagents allow quantification of live and dead cells at differing fluorescent wavelengths. After the first round of live/dead assays, the hits are selected, and the assays are performed with triplicate measurements to ensure that the results are accurate. In stage 2, hits that are confirmed from stage 1 are used for MTT proliferation assays as follows using a commercial kit (R&D Systems, Inc., Minneapolis, Minn.). 5000 CSRD1 cells/well are seeded into 96-well plates and allowed to attach overnight. Serially diluted concentrations of the drug of interest are added to the wells. After the cells have been exposed to drug for 24 hours, MTT is added, and the cells are incubated and then solubilized per manufacturer instructions. The absorbance at 550 nm is determined using a microplate reader, and the percent viability is calculated relative to vehicle controls. In stage 3, hits that were significant in the initial MTT assays are further assessed. $1 \times 10^5$ CSRD1 cells/well are seeded into 6-well plates and treated with the optimal drug concentration as determined from the MTT assays. These treated cells are then subjected to annexin V apoptosis assay, live-cell imaging, real-time RT-PCR, and western blot as needed. Many drugs in the small-molecule library are already very well characterized (for example but not limited to, paclitaxel). For these drugs, resources are not wasted on characterization; instead comparative studies are pursued using cancer cell lines. Briefly, 5000 HeLa cervical cancer, HCT116 colon cancer, AsPC-1 pancreatic cancer, MDA-MB-231 triple-negative breast cancer, and CSRD1 cells are seeded into 96-well plates and treated with the optimal concentration of drug determined previously by MTT. MTT assays are performed on these cells as described above in order to obtain a resistance profile for the compound of interest in CSRD1 cells. The optimal compounds cause CSRD1 cell death as well as they do in the other cancer lines that are screened against.

In order to meet Purpose 2 of this Example, novel ADCs are synthesized by conjugating molecules with therapeutic potential to an anti-DCLK1 monoclonal antibody (such as but not limited to, 4B5B3). The lead compounds found in Purpose 1 are conjugated to an antibody targeting the extracellular c-terminus of DCLK1 produced as described herein above. In order to accomplish this, small-molecule linking reagents are used. In general, non-cleavable, bifunctional linking reagents are used as much as possible because of the increase in therapeutic specificity seen with ADCs prepared with these reagents. However, in some situations cleavable linkers are used due to the structure of the small molecule drug and the limited commercial availability of linking reagents. In order to demonstrate the experimental architecture of this stage, a general synthetic framework with two example compounds is given below.

The first example is directed to the conjugation of Paclitaxel to monoclonal antibody 4B5B3; this example is particularly applicable to hydroxyl containing therapeutics. The architecture of this conjugation is depicted in FIG. 46. First, a 10-fold molar excess of p-Maleimidophenyl isocyanate (PMPI; Thermo Fisher Scientific, Waltham, Mass.) relative to free hydroxyl groups is added to dry DMSO containing Paclitaxel, mixed, and incubated at room temperature for 1 hour. 4B5B3 cysteine groups are activated by incubation in 3.25 molar-excess DTT in PBS for 1.5 hour. Excess DTT is removed by size-specific dialysis (10 kDa pore size). Activated 4B5B3 is added to sterile water, and the pH is adjusted to 6.5 by dropwise addition of HCl. The carbamate-linked compound from step (a) is added in 10-fold molar excess to the reaction mixture and incubated overnight at 4° C. Finally, excess reagents are removed by dialysis as in step (b), and the drug-to-antibody ratio (DAR) is determined by UV/Vis spectroscopy.

In a second example, Sorafenib is conjugated to monoclonal antibody 4B5B3; this example is particularly applicable to amine (1° and 2°) containing therapeutics. A 10-fold molar excess of Succinimidyl-4-(N-maleimidomethyl)cyclohexane-1-carboxylate (SMCC; Thermo Fisher Scientific, Waltham, Mass.) relative to amine groups is added to sterile PBS containing Sorafenib, mixed, and incubated at room temperature for 1 hour. 4B5B3 cysteine groups are activated by incubation in 3.25 molar-excess DTT in PBS for 1.5 hours. Excess DTT is removed by size-specific dialysis (10 kDa pore size). Activated 4B5B3 is added to the reaction mixture from step (a) and incubated at 37° C. for 30 minutes and held at 4° C. overnight. Finally, excess reagents are removed by dialysis as in step (b) and DAR determined by UV/Vis spectroscopy.

The therapeutic efficacy of ADCs synthesized as described above are then tested in the CSRD1 TSC line in vitro and in vivo. ADCs synthesized as described above are tested against the CSRD1 cell line in standard culture conditions. Cells are treated with equivalent amounts of vehicle, small-molecule alone, antibody alone, or ADC. Assays are conducted as needed to compare the efficacy of the ADC, but in general, MTT proliferation assay is used for the initial testing. Similar toxicity in monolayer culture for ADCs compared to small-molecule alone is expected.

To determine whether ADCs regulate tumor invasion, an in vitro assay of tumor invasion is performed with a MATRIGEL® invasion chamber (BD Biosciences, San Jose, Calif.). BD MATRIGEL® Matrix includes collagen IV, laminin, entactin, heparan sulfate, and proteoglycan and provides a biologically active basement membrane model for in vitro invasion assays. These microporous membranes create an in vitro model to mimic the metastatic process of tumor cells in vivo. Briefly, MATRIGEL® filter inserts for 24 well plates with a pore size of 8 µM are seeded with 2.5×10$^4$ CSRD1 cells and inserted into a well. Serum-free media with appropriate dosage of ADC (based on the MTT proliferation assay) is added to the top of the chamber, and standard media containing 10% FBS is added to the bottom chamber as chemo-attractant. The cells are incubated for 24 hours. Cells on top of the insert are scraped off, and those at the bottom of the insert are fixed and stained with a Kwik-Diff™ staining kit (Thermo Fisher Scientific, Inc., Waltham, Mass.). The number of positive cells in the membrane is counted by light microscopy. ADCs that can limit invasion in this assay are considered candidate ADCs to test further for potential against invasive malignancies.

ADCs that perform well in in vitro testing are subjected to in vivo assays using CSRD1 isografts. Briefly, CSRD1 cells (5×10$^5$) are injected into the flanks of athymic nude mice. Mice are monitored weekly for the formation of tumors. When tumors reach a volume of 100 mm$^3$, these mice are injected intraperitoneally (ip) with ADC, 4B5B3 alone, small-molecule alone, or vehicle. The injections are performed once per week, the tumor volume measured every other day using calipers, and the mice monitored for signs of toxicity. If significant signs of toxicity are observed, the experiment is discontinued and the dosage reassessed. If signs of toxicity are not present or limited, the experiment runs until the vehicle control tumors reach a volume of 2×10$^3$ mm$^3$. At this point, mice are culled and final tumor volumes and weights measured. Tumor tissue, serum, and organs are collected and stored at −80° C. for further analysis. Analyses that may be conducted include, but are not limited to, real time RT-PCR, western blots, and immunohistochemistry.

Example 10

In this Example, an antibody-drug conjugate targeting extracellular DCLK1 is constructed that includes: (a) at least one general cytotoxic agent; (b) at least one bifunctional or multifunctional linking molecule and/or peptide that is bound to the cytotoxic agent(s); and (c) at least one antibody and/or peptide targeting extracellular DCLK1 protein that is bound to the cytotoxin-modified linking molecule and/or peptide.

In this Example, the cytotoxic drug Paclitaxel is reacted with an isocyanate moiety of the linking molecule N-(para-maleimidophenyl)isocyanate (PMPI) to form a carbamate linkage between the two molecules. The maleimide moiety of this product is subsequently reacted with a DCLK1 monoclonal antibody (such as the monoclonal antibodies described herein above in Examples 5-7) to form a thioether linkage between the modified cytotoxin and the antibody to yield the final product (FIG. 46).

The antibody-drug conjugate is utilized to target DCLK1-expressing cancer cells for destruction. One benefit of this method is that targeting DCLK1$^+$ cells leads to the destruction of cancer stem cells (CSCs) and progenitors, thus resulting in reduction and/or ablation of tumors, blockage of epithelial-mesenchymal transition, and/or the prevention of relapse and metastasis. DCLK1 is expressed in circulating tumor cells (CTCs); therefore, this method will capture and destroy metastatic cells in circulation bound for attachment to sites away from the primary tumor. Additionally, DCLK1 is overexpressed or mutated in many cancers, and therefore this method leads to the destruction of cancerous cells in general, regardless of their CSC or CTC characteristics. Another benefit of the use of this antibody-drug conjugate is that targeting DCLK1-expressing cells specifically for chemotherapy results in reduced side effects compared to therapy with the cytotoxic compound alone.

Example 11

In this Example, the efficacy of antibody-drug conjugate driven targeted depletion of TSCs is determined using cells derived from animal models of neoplasia. The Apc$^{min/+}$ mouse is a well-characterized model of intestinal neoplasia. The Pdx$^{Cre}$-LSL-Kras$^{G12D}$-P53$^{flox}$ (KPC) mouse accurately mimics human PDAC and is the most-oft studied and best characterized mouse model of this disease. The DCLK1$^+$ cell has been shown to specifically mark TSCs in Apc$^{min/+}$ mice, and inducible ablation of this cell reverts disease in this mouse model without negative effect on normal tissue (Nakanishi et al., Nature Genetics (2012) 45:98-103). In the pancreas, the introduction of the Kras$^{G12D}$ mutation into DCLK1$^+$ cells is capable of initiating PDAC (Westphalen et al. (2012) Gastroenterology, S-50), and DCLK1 is highly expressed in PDAC but shows low expression in the normal pancreas, demonstrating that the DCLK1$^+$ cell may also be a TSC marker in PDAC. ADCs developed as described in Examples 8-9 are tested against isografts generated from DCLK1$^+$ spheroids transplanted into athymic nude mice. ADCs that prove successful are further tested in the parent mouse lines (Apc$^{min/+}$ or KPC).

Isolation of DCLK1$^+$ and DCLK1$^-$ cells from Apc$^{min/+}$ and KPC tumors. DCLK1$^+$ tumor stem cells are isolated from Apc$^{min/+}$ mouse intestinal adenomas and KPC pancreatic tumors using anti-Dclk1 antibody. Briefly, the tumors are rapidly dissected, removed, and washed with cold HBSS. The dissected tissues are incubated with 1 mM DTT for 30 minutes at room temperature and then washed and incubated with 30 mM EDTA in HBSS (without Ca$^{2+}$ and Mg$^{2+}$) for 10 minutes at 37° C. The tumors are washed gently with cold HBSS and transferred to fresh HBSS, shaken vigorously 5 to 10 times and filtered through a 400 µM mesh to separate detached epithelial cells from the tissue. The filtrate are further filtered through a 40 µM mesh and washed three times with HBSS. The epithelial cells retained on the mesh are incubated with trypsin at 37° C. and pipetted up and down to create a single cell suspension. Staining is performed with ALEXA FLUOR® 488 or 568 (Life Technologies Corp., Grand Island, N.Y.) conjugated anti-DCLK1 antibody, and cell sorting is performed using Influx-V cell sorter (Cytopeia Inc., Seattle, Wash.). Both DCLK1$^+$ and DCLK1$^-$ cells isolated from intestinal and pancreatic tumors are plated and allowed to form spheroids in suspension culture for 21 days.

Testing of ADCs in vivo against DCLK1$^+$ isografts from Apc$^{min/+}$ and KPC tumors. Mechanically dissociated cells (1×10$^3$) from the spheroids generated as described in Examples 8-9 are injected subcutaneously into the flanks of athymic nude mice and monitored for the appearance of nodules. Nodules are measured with calipers, and the volume is calculated. When the nodules reach a size of 100 mm$^3$, the nude mice are injected ip with ADCs and control compounds. Dosage and injections schedules are determined based on the results of the isograft assays performed as described in Examples 8-9. Tumor volumes are measured every other day, and animals are sacrificed after vehicle controls reach a volume of 1000-2000 mm$^3$, depending on the length of the experiment and rate of isograft growth. After an endpoint is reached, mice are culled, and final tumor volumes and weights are measured. Tumor tissue, serum, and organs are collected and stored at −80° C. for further analysis. Analyses that may be conducted include quantitative real time RT-PCR, western blots, and immunohistochemistry.

Testing of ADCs in vivo in Apc$^{min/+}$ and KPC mice. Apc$^{min/+}$ mice rapidly develop intestinal adenomas, and KPC mice develop PanIN lesions by 6 weeks of age (Morton et al. (2010) PNAS 107:246-251). Apc$^{min/+}$ and KPC mice are treated with drugs that demonstrated efficacy as described in Examples 8-9. Both Apc$^{min/+}$ and KPC mice are injected with ADC, anti-DCLK1 antibody alone, drug alone, or vehicle starting at six weeks of age. The dosing schedule is determined based on the previous results with the drug, and mice are culled after 6-8 weeks of drug treatment. Serum, tumor tissue, and organs are collected for further analysis and stored at −80° C. Hematoxylin and eosin (H&E) staining is performed on the tumorous tissue, and immunohistochemistry (IHC) for DCLK1 and any other proteins of interest is performed. H&E and IHC slides are characterized, staged, and assessed for staining intensity by a pathologist. A statistically significant decrease in size or loss of polyps/tumors is considered an experimental success. If significant therapeutic effects are detected by histology, mRNA and protein analyses of relevant factors is performed based on the disease model (i.e. Apc, WNT-signaling factors, Notch pathway genes, Kras, EMT factors, etc.).

This Example, in combination with the other examples (and particularly, Examples 8-9), allows for the synthesis and assessment of compounds constructed in accordance with the presently disclosed and claimed inventive concept(s) that cause tumor/adenoma regression in the isografts and animal models. These compounds directly demonstrate the potency of this targeting platform.

Thus, in accordance with the presently disclosed and claimed inventive concept(s), there have been provided specific DCLK1 binding agents, and methods of use thereof, that fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

REFERENCES

The following references, to the extent that they provide exemplary procedural or other details supplementary to those set forth herein, are specifically incorporated herein by reference.

Abraham et al. Am J Pathol (2004) 164:817-830.
Al-Hajj et al. Proc Natl Acad Sci USA (2003) 100:3983-3988.
Arias A M. Cell (2001) 105:425-31.
Bao et al. Nature (2006) 444:756-760.
Bao et al. Cancer Res (2006) 66:7843-7848.
Barker et al. Nature (2007) 449:1003-1007.
Bartel D P. Cell (2004) 116:281-97.
Becker et al. Scientific World Journal (2008) 8:1168-1176.
Bishnupuri et al. Gastroenterology (2006) 130:137-49.
Bjerknes et al. Gastroenterology (1999) 116:7-14.
Bjerknes et al. Am J Physiol Gastrointest Liver Physiol (2005) 289:G381-387.
Bjerknes et al. The Am J of Anatomy (1981) 160:77-91.
Bjerknes et al. The Am J of Anatomy (1981) 160:93-103.
Bonnet et al. Nat Med (1997) 3:730-737.
Brummelkamp et al. Science (2002) 296:550-553.
Bussing et al. Trends Mol Med (2008) 14:400-409.
Calabrese et al. Proc Natl Acad Sci USA (2007) 104:18097-18102.
Calin et al. Nat Rev Cancer (2006) 6:857-866.
Calin G A. Proc Natl Acad Sci USA (2004) 101:2999-3004.
Chendrimada et al. Nature (2005) 436:740-4.
Cheng et al. The Am J of Anatomy (1974) 141:537-561.
Cheng et al. The Am J of Anatomy (1974) 141:461-479.
Cheshier et al. Proc Natl Acad Sci USA (1999) 96:3120-3125.
Clarke A R. Oncogene (2006) 25:7512-7521.
Clevers H. Cancer Cell (2004) 5:5-6.
Clevers H. Cell (2006) 127:469-480.
Cohn et al. The J of Cell Biol (1992) 119:27-44.
Cohn et al. J Clin Invest (1997) 99:1367-1379.
Corpet et al. Eur J Cancer (2005) 41:1911-1922.
Cotsarelis et al. Cell (1990) 61:1329-1337.
Croce et al. Cell (2005) 122:6-7.
de Lau et al. Front Biosci (2007) 12:471-491.
Crossman et al. J Cell Biol (1994) 126:1547-1564.
Dekaney et al. Gastroenterology (2005) 129:1567-1580.
Diehn et al. J Natl Cancer Inst (2006) 98:1755-1757.
Dontu et al. Genes Dev (2003) 17:1253-1270.
Fearon et al. Cell (1990) 61:759-767.
Frye et al. Development (Cambridge, England) (2003) 130:2793-2808.
Giannakis et al. Proc of the Natl Academy of Sci of the USA (2008) 105:4358-4363.
Giannakis et al. J Biol Chem (2006) 281:11292-11300.
Gordon et al. Curr Opin Cell Biol. (1994) 6:795-803.
Gregory R I. Nature (2004) 432:235-240.
Grossmann et al. EP J of Cell Biol (2003) 82:262-270.
Gu et al. Development (2002) 129:2447-2457.
Guweidhi et al. Carcinogenesis (2004) 25:1575-1585.
Hatfield et al. Nature (2005) 435:974-978.
Hauft et al. The J of Cell Biol (1992) 117:825-839.
Hingorani et al. Cancer Cell (2003) 3:414-417.
Houchen et al. Am J Physiol Gastrointest Liver Physiol (2000) 279:G858-865.
Hoyer et al. Acta Oncol (2006) 45:823-830.
Humphries et al. Nature reviews (2008) 8:415-424.
Ibarra et al. Genes Dev (2007) 21:3238-3243.
Ishizuka et al. Nucleic Acids Res (2003) 31:6198-6205.
Jackson et al. Genes Dev (2001) 15:3243-3248.
Jensen et al. Diabetes (2000) 49:163-176.
Johansson et al. Dev Cell (2007) 12:457-465.
Jones et al. Cell (2007) 128:683-692.
Karam et al. The Anatomical Record (1993) 236:259-279.
Kayahara et al. FEBS Lett (2003) 535:131-135.
Kim et al. Nat Struct Biol (2003) 10:324-333.
Kumar et al. Nat Genet (2007) 39:673-677.
Lagos-Quintana et al. Science (2001) 294:853-858.
Lechner et al. Biochem Biophys Res Commun (2002) 293:670-674.
Lee et al. Science (2001) 294:862-864.
Lee et al. Nat Biotechnol (2002) 20:500-505.
Li et al. Cancer Res (2007) 67:1030-1037.
Lin et al. J Neurosci (2000) 20:9152-9161.
Logsdon et al. Cancer Res (2003) 63:2649-2657.
Marshman et al. Bioessays (2002) 24:91-98.
Masters et al. Mol Pharmacol (2001) 60:1325-1331.
May et al. Stem Cells (2008) 26:630-637.
McClanahan et al. Cancer Biol & Ther (2006) 5:419-426.
McManus Mont. Semin Cancer Biol (2003) 13:253-258.
Merritt et al. Cancer Res (1994) 54:614-617.

Mickisch et al. J Urol (1993) 149:174-178.
Miyagashi et al. Nat Biotechnol (2002) 20:497-500.
Moll et al. Histochem Cell Biol (2008) 129:705-733.
Niemeyer et al. Exp Hematol (2001) 29:686-693.
Obernosterer et al. Rna (2006) 12:1161-7; Diabetes (2001) 50:521-533.
Paddison et al. Proc Natl Acad Sci USA (2002) 99:1443-1448.
Phillips et al. J Natl Cancer Inst (2006) 98:1777-1785.
Polakis P. Genes Dev (2000) 14:1837-1851.
Pollack et al. Dig Dis Sci (1990) 35:749-758.
Poste et al. Invasion Metastasis (1982) 2:137-176.
Potten et al. Cell Prolif (2003) 36:115-129.
Potten et al. Intl J Exp Pathol (1997) 78:219-243.
Potten et al. Differentiation (2003) 71:28-41.
Potten et al. J of Theo Biol (1987) 127:381-391.
Potten et al. Development (Cambridge, England) (1990) 110:1001-1020.
Potten et al. Intl J Radiat Biol (1994) 65:71-78.
Potten et al. J Cell Sci (2002) 115:2381-2388.
Potten et al. Int J of Radiat Biol (1988) 54:1041-1051.
Potten C S. Int J Radiat Biol 1990; 58:925-973.
Powell et al. Nature (1992) 359:235-237.
Purkis et al. J of Cell Sci (1990) 97 (Pt 1):39-50.
Quante et al. Physiology (Bethesda) (2008) 23:350-359.
Radford et al. Cell Prolif (2006) 39:403-414.
Radtke et al. Science (2005) 307:1904-1909.
Reinhart B. Nature (2000) 403:901-906.
Reya et al. Nature (2001) 414:105-111.
Riehl et al. Gastroenterology (2000) 118:1106-1116.
Rizvi et al. Stem Cells (2005) 23:150-65.
Rubin et al. The J of Biol Chem (1992) 267:15122-15133.
Samuel et al. Am J Physiol Cell Physiol (2009) 296:C296-305.
Sancho et al. Curr Opin Cell Biol (2003) 15:763-770.
Sangiorgi et al. Nat Genet (2008) 40:915-920.
Sansom et al. J Biol Chem (2005) 280:28463-28467.
Schmidt et al. Cell (1985) 40:425-429.
Schwitzgebel et al. Development (2000) 127:3533-3542.
Shcherbata et al. Cell Cycle (2006) 5:172-175.
Shroyer et al. Genes & Development (2005) 19:2412-2417.
Shu et al. Neuron (2006a) 49:25-39.
Shu et al. J Biol Chem (2006b) 281:11292-11300.
Singh et al. Oncogene (2004) 23:7267-7273.
Singh et al. Cancer Res (2003) 63:5821-5828.
Singh et al. Nature (2004) 432:396-401.
Smith et al. Clin Cancer Res (1996) 2:1049-1053.
Sossey-Alaoui et al. Genomics (1999) 56:121-126.
Stadler et al. Cell (2008) 132:563-566.
Suh et al. Dev Biol (2004) 270:488-498.
Sui et al. Proc Natl Acad Sci USA (2002) 99:5515-5520.
Sureban et al. Gastroenterology (2008) 134:1448-1458.e1442.
Sureban et al. Oncogene (2008) 27:4544-4556.
Sureban et al. J Nanobiotechnology (2011) September 19; 9:40
Sureban et al. Cancer Res. (2011) March 15; 71(6):2328-38.
Takamizawa et al. Cancer Res (2004) 64:3753-3756.
Tamaki et al. J Neurosci Res (2002) 69:976-986.
Tang et al. Faseb J (2007).
Tessner et al. Gastroenterology (1998) 115:874-882.
Theodosiou et al. Dev Biol (2003) 259:258-271.
Thomson et al. Genes Dev (2006) 20:2202-2207.
Tricoli et al. Cancer Res (2007) 67:4553-4555.
Turley et al. Nat Clin Pract Oncol (2008) 5:280-290.
Vella et al. Genes Dev (2004) 18:132-137.
Viswanathan et al. Science (2008) 320:97-100.
Winton et al. Proc Biol Sci (1990) 241:13-18.
Withers et al. Int J Radiat Biol Relat Stud Phys Chem Med (1970) 17:261-267.
Wright NA. Int J Exp Pathol (2000) 81:117-143.
Xu et al. Cell (2008) 132:197-207.
Yang et al. Science (2001) 294:2155-2158.
Yu et al. Cell (2007) 131:1109-1123.
Zenilman et al. J Gastrointest Surg (1997) 1:194-201.
Zhang et al. CN Medical J (2003) 116: 918-922.
Zhang et al. Nature (2003) 425:836-841.
Zulewski et al. Diabetes (2001) 50:521-533.

What is claimed is:

1. A method of inhibiting activity of DCLK1 protein in a subject, comprising the step of:
   administering to a subject an effective amount of a pharmaceutical composition comprising a monoclonal antibody against DCLK1, thereby specifically inhibiting the activity of DCLK1 in DCLK1-expressing cells, wherein the monoclonal antibody specifically binds to at least one of:
   an epitope of DCLK1 represented by SEQ ID NO:20; and
   an epitope of DCLK1 represented by SEQ ID NO:21.

2. The method of claim 1, wherein the pharmaceutical composition further comprises a delivery agent.

3. The method of claim 2, wherein the delivery agent comprises a liposome.

4. The method of claim 1, wherein the pharmaceutical composition is further defined as comprising an antibody-drug conjugate, wherein the monoclonal antibody against DCLK1 is conjugated to a cytotoxic agent.

5. A method of inhibiting tumor growth, comprising the step of:
   contacting a DCLK1-expressing tumor with a monoclonal antibody against DCLK1, thereby specifically inhibiting activity of DCLK1 in the DCLK1-expressing tumor and thus inhibiting growth of the DCLK1-expressing tumor, wherein the monoclonal antibody specifically binds to at least one of:
   an epitope of DCLK1 represented by SEQ ID NO:20; and
   an epitope of DCLK1 represented by SEQ ID NO:21.

6. The method of claim 5, wherein the inhibition of activity of DCLK1 in the DCLK1-expressing tumor results in at least one of a decrease in cancer cell proliferation, apoptosis, $G_2/M$ arrest, mitotic catastrophe, a decrease in at least one of mRNA stability and mRNA translation for at least one of c-Myc, KRAS, and combinations thereof, and an increase in miRNA expression.

7. The method of claim 5, wherein the monoclonal antibody is provided in the form of an antibody-drug conjugate, wherein the monoclonal antibody against DCLK1 is conjugated to a cytotoxic agent.

8. A method of inhibiting tumor growth in a DCLK1-expressing colon or pancreatic tumor in a subject, comprising the steps of:

administering an effective amount of a pharmaceutical composition to the subject, wherein the pharmaceutical composition comprises a monoclonal antibody against DCLK1, thereby specifically inhibiting the activity of DCLK1 in the DCLK1-expressing colon or pancreatic tumor and thus inhibiting growth of the DCLK1-expressing colon or pancreatic tumor, wherein the monoclonal antibody specifically binds to at least one of:

an epitope of DCLK1 represented by SEQ ID NO:20; and an epitope of DCLK1 represented by SEQ ID NO:21.

9. The method of claim 8, wherein the inhibition of activity of DCLK1 results in at least one of a decrease in cancer cell proliferation, apoptosis, $G_2$/M arrest, mitotic catastrophe, a decrease in at least one of mRNA stability and mRNA translation for at least one of c-Myc, KRAS, and combinations thereof, and an increase in miRNA expression.

10. The method of claim 8, wherein the pharmaceutical composition further comprises a delivery agent.

11. The method of claim 10, wherein the delivery agent comprises a liposome.

12. The method of claim 8, wherein the pharmaceutical composition further comprises at least one additional chemotherapeutic agent.

13. The method of claim 8, wherein the pharmaceutical composition is further defined as comprising an antibody-drug conjugate, wherein the monoclonal antibody against DCLK1 is conjugated to a cytotoxic agent.

14. A method of treating and/or decreasing the occurrence of DCLK1-expressing colonic and/or pancreatic neoplastic cells in a patient in need of such therapy, comprising the step of:

administering an effective amount of an antibody-drug conjugate to the patient, wherein the antibody-drug conjugate comprises a monoclonal antibody against DCLK1 conjugated to a cytotoxic agent, whereby DCLK1-expressing colonic and/or pancreatic neoplastic cells in the patient are depleted, and wherein the monoclonal antibody specifically binds to at least one of:

an epitope of DCLK1 represented by SEQ ID NO:20; and an epitope of DCLK1 represented by SEQ ID NO:21.

* * * * *

UNITED STATES PATENT AND TRADEMARK OFFICE
CERTIFICATE OF CORRECTION

PATENT NO. : 9,663,585 B2  Page 1 of 1
APPLICATION NO. : 14/073169
DATED : May 30, 2017
INVENTOR(S) : Courtney Houchen et al.

It is certified that error appears in the above-identified patent and that said Letters Patent is hereby corrected as shown below:

In the Specification

Column 8, Line 48: After "Msi-1," delete "(1):" and replace with -- (L): --
Column 11, Line 19: Delete "P48$^{cre}$" and replace with -- P48$^{Cre}$ --
Column 27, Line 67: Delete "PlanAPO" and replace with -- PlanAPO --
Column 33, Line 52: Delete "Pdx48$^{cre}$" and replace with -- Pdx48$^{Cre}$ --
Column 40, Line 17: Delete "(LRCS)" and replace with -- (LRCs) --
Column 55, Line 24: Delete "DCAMKL-I" and replace with -- DCAMKL-1 --
Column 56, Line 61: Delete "P48$^{cre}$" and replace with -- P48$^{Cre}$ --
Column 56, Line 65: Delete "P48$^{cre}$" and replace with -- P48$^{Cre}$ --
Column 57, Line 1: Delete "P48$^{cre}$" and replace with -- P48$^{Cre}$ --
Column 60, Line 46: Delete "46563" and replace with -- 4B5B3 --
Column 66, Line 66: After "McManus" delete "Mont." and replace with -- MT. --

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 22

<210> SEQ ID NO 1
<211> LENGTH: 8082
<212> TYPE: RNA
<213> ORGANISM: Homo sapiens

<400> SEQUENCE: 1
uuucaaugag gacgggccga ggcacauccc ugcacuagug gccgcaaccg aggcgccgcg      60
cuccagcagc ugcugccgcc cagcccggcc ccgccgccgc ccccagccc ugcagccccg     120 cagccccggc cgcgcccagc ccggcgagga cagcaccagg aggcggcccc cagcgcggcc     180
acaaagaccc ccggcggcgu cucuccgcgg accguccua cuugaagucc aucauguccu     240
ucggcagaga cauggagcug gagcacuucg acgagcggga uaaggcgcag agauacagcc     300
gagggucgcg ggugaacggc cugccgagcc cgacgcacag cgcccacugc agcuucuacc     360
gcacccgcac gcugcagacg cucagcuccg agaagaaggc caagaaaguu cguuucuauc     420
gaaacggaga ucgauacuuc aaagggauug uguaugccau cucccagac cgguccgau     480 cuuugaggcc ccugcuggcu gauuugaccc gaacucuguc ggauaacgug aauuugcccc     540
agggagugag aacaaucuac accauugaug ggcucaagaa gauuccagc cuggaccaac     600
```

```
uggugaagg agagaguuau guaugugcu ccauagagcc cuucaagaaa cuggaguaca    660
ccaagaaugu gaaccccaac uggucggugu acgucaagac caccucggcu ucucgggcag    720
ugucuucacu ggccacugcc aaaggaagcc cuucagaggu gcgagagaau aaggauuuca    780
uucggcccaa gcuggucacc aucaucgaau guggcgugaa gccacggaaa gcugucagga    840
uucugcugaa caagaaaacg gcucauuccu ugagcaggu ccaccgau aucaccgaug    900 ccaucaagcu ggacucggga guggugaaac gccuguacac guuggaugg aaacagguga    960 ugugccuuca ggacuuuuuu ggugaugaug acauuuuuau ugcaugugga ccggagaagu    1020
uccguuacca ggaugauuuc uugcuagaug aaagugaaug ucgaguggua aaguccacuu    1080
cuuacaccaa aauagcuuca ucaucccgca ggagcaccac caagagccca ggaccgucca    1140
ggcguagcaa ucccccugcc uccaccagcu caguuaaugg aacccccuggu agucagcucu    1200 cuacuccgcg cucaggcaag ucgccaagcc caucaccac cagcccagga agccugcgga    1260
agcagaggag cucucagcau ggcggcuccu cuacgucacu ugcguccacc aaagucugca    1320
gcucgaugga ugagaacgau ggcccuggag aagaagucgc ggaggaaggc uuccagauuc    1380
cagcuacaau aacagaacga uauaaagucg gaagaacaau aggagaugga aauuuugcug    1440
uugucaagga uguguagaa agaucgacug cuagagagua ugcucugaaa auuaucaaga    1500
aaagcaaaug ucgaggcaaa gagcacauga uccagaauga agucuauau uuaagaagag    1560 ugaagcaucc caauaucguu cuucugauug aggagaugga ugugccaacu gaacuguauc    1620 uugcaugga auuaguaaag gggggagacc uuuuugaugc cauuacuucc acuaacaaau    1680
acaccgagag agacgccagu gggaugcugu acaaccuagc cagcgccauc aaauaccugc    1740
auagccugaa caucguccac cgugauauca gccagagaa ccugcgggug uaugagcacc    1800
aagauggcag caaaucacug aagcugggug acuuuggacu ggccaccauu guagacggcc    1860
cccuguacac agucugugc accccaacau acguggcucc agaaaucauu gcagagacug    1920
gauacggccu caaggugga aucugggcag caggguauu cacuuauauc cugcugugug    1980
guuucccucc auccgugga aguggugau accaggaggu gcuuuugau cagauuuga    2040 uggggcaggu ggacuuuccu ucuccauacu gggauaaugu uccgauucu gcaaaggagc    2100 ucauuaccau gaugcuguug gucgauguag aucagcgauu ucugcguu caaguacuug    2160 agcaucccug gguuaaugau gauggccucc cagaaaauga acaucagcug ucaguagcug    2220
gaaagauaaa gaagcauuuc aacacaggcc ccaagccgaa uagcacagca gcuggaguuu    2280 cugcauagc acuggaccac ggguuuacca ucaagagauc agggucuuug gacuacuacc    2340
agcaaccagg aauguauugg auaagaccac cgcucuugau aaggagaggc agguuuccg    2400 acgaagacgc aaccaggaug ugaggagccg guacaaggcg cagccagcuc ucccgaacu    2460 caacucggaa ucggaagacu acuccccaag cuccuccgag acuguucgcu ccccuaacuc    2520
gcccuuuuaa uaagacccuu uuacucaaag uccuagcuua accccuugag acucugagau    2580
uuuuuccccc caaauuugug uaaaacaguu ucaucugauc uaucuagcgc ucaaugcuug    2640
aauggcagaa cugaaagugu uucaggauu cuuuguagcg guuccccuuu acugaauaag    2700
augacacgug ugauuguga agauggauau uugcugcuaa uagagccuc aaaggguuaa    2760 ggccaauuug caauuuuuu uuaaacuuag aagcaaugaa uguuucauc agucaagcua    2820 ggaucugcag uauguaauau agcacuuguu aaccccucga gugcauagaa uuuauugag    2880 aauucuuguu ugggaauuuu ucaggccuuu ggauguauac acacauguuu cuugauuuua    2940
```

| | | | | | |
|---|---|---|---|---|---|
|cugcagauca|aggggguguug|uuagaugcug|aaauguccag|aaaagaagga|cauuuagaau| 3000
|gauaucuugu|uugaccuuuu|cuguggguuu|agaacguggc|agguuuauaa|cuucgacaca| 3060
|cgcacgguuc|uuucuucuuc|acaauccuau|ucagaaacag|auuuuuuuu|ucauuagaga| 3120
|uaugacuguc|aguugcagug|aguucugcau|cccaagugga|gggaauuggg|uuuguggcaa| 3180
|agagcuugac|ccaggaaaua|gauggugccc|cccaaauugu|cuccacauga|agauguacug| 3240
|augacgcccc|agaaaugcug|cuuccauauc|agcugcugcu|agcgccagcg|cagacucuca| 3300
|gggagucacc|acagcuuguc|uugugcuugg|ugagugaggg|ucucucuacu|cagugucaga| 3360
|caucuacagg|aaagaaacaa|cugguggaaa|agagcaauaa|auugcccggu|gcucugcagg| 3420
|gcuggaauuu|caaacagaaa|gagggaauaa|gauccuguga|uuuucucac|cugcuuuucc| 3480
|acgcacugug|ucaucacug|ugcaaucuac|aucuaguaug|aaauccacac|auaggagagc| 3540
|ugggcacaa|gggacugga|ggcaguugcu|uugcaagaug|gcugaggaga|aagcacacug| 3600
|ggaacacaau|ccagaauguu|cuaacaauaa|guuucagug|aauaaaccac|uggcaagaca| 3660
|auuccaugug|caccuuuagg|uuaccauauau|agucccuag|gaagaucagg|augaaagacc| 3720
|uagaugauac|cccugaggau|aaaaccucca|uccccuaaaa|ugauuuuuu|uaaauaccac| 3780
|ugucuuuagc|ugccaggag|ucagagugu|uuuucuguc|uuugggccaa|guccugucug| 3840
|agaccuguau|uuucacucuu|guuaccaaau|cuaucccccu|agugcagugu|cuccaggccu| 3900
|gaguuucuuc|uggaacagau|uccauuuuag|aaugggauu|cacagguucu|gugcaucacc| 3960
|acagugcuca|gagaggauuc|uccugggugu|gcuuagaggc|aggugcccaa|cucaaaugua| 4020
|uucccaaggu|uugcugggcu|cugggauccca|cgagacaacc|agagagggau|aucucaugaa| 4080
|auuugcaucu|ggugcugaa|caguaccuau|guucucuguu|uugaauauac|uuuaauaccu| 4140
|gagaguuuua|aaauuuguga|acaacguuuc|uauaguccuu|uauuucaaa|ugcacauuga| 4200
|ucuucacuug|cugcauuuuu|acuucaac|ccugaaacua|uggucuacau|uaauauggau| 4260
|uuuuaaauca|caugucauua|cuuuugcaac|accaucacca|aaauuuuug|ucuuuuaca| 4320
|uuuagguuca|ucucguggu|cugugugu|cugacauguu|aaaagcauau|cguuuauuga| 4380
|gguuuuuuc|cccccuuuu|agagcauccg|gaaugauaa|cacgcaaaau|cacaaaguag| 4440
|cauaaaucag|uaaauuaguu|gaguguuuu|ugggggggag|gugggggua|gggcacaga| 4500
|acaccagaaa|gaguguuggu|guguaggag|auuccauauu|aaugaggaac|acgaacuag| 4560
|uuggaaauua|cugcuuucuc|uagaaauaua|aagcaaagca|cuauuccaag|gcuauggagu| 4620
|agcucuacag|ccuggccuca|acucuaaaag|ugugaagaau|gcaaugggca|gagaccuacc| 4680
|ugcaguggac|ugucauuuc|cuucuuucu|cugaauuacu|gcuuuucug|ugggcauuaa| 4740
|cuauauugcu|acagcaucua|guguacgag|ccugcggugc|auggcucagg|ccuuucccca| 4800
|ucgacgucua|gggggacucu|ggaccgugug|aagcuagggg|guguuucuca|gcacacugca| 4860
|gaagggcagc|ucagaagaau|gcagggccca|ucagcaugg|ggaucccagc|acaucacugu| 4920
|agaauuugag|ugaucuaugc|ugaauaaaca|guggaaugug|accagucaag|uagaaaucuu| 4980
|gaguaaucag|auggaaugca|aucuuucuaa|cauuaagcua|ccaagauccu|gaaugucaga| 5040
|gauguacuca|gaggguuaac|agacaagcac|aaggcaugcu|gacuacauug|uguauccag| 5100
|auugcuuugc|uuuuagccag|ugcuuucaa|uuuuuuucuc|gacauucuug|ggauaguuca| 5160
|aguuugaaau|aauuaagugg|ugguguucuu|uaaggaauuu|cuauaaccaa|auugaucuua| 5220
|uuuuugauuu|cacuuaucau|agaacaaaua|uguaucauua|uggcaguugua|ucuauguaau| 5280
|uaucaauuua|aucaucacca|ccggugunuc|cauauuuuu|cccaaguauu|uaauauagcu| 5340

```
cucuuauggu gguggccugg ugauggggac cgucuuucuu uuacugacac augaccaauc    5400
auaugguauu uucaagggaa uuuuaagauu caucuuuuca guuugauagu agacuaguua    5460
aggaagaacu cuuucauuac uugcaucgug uaaaucaucu cuguagacau guguucauau    5520
uaaugaacac auuuuuucuc aacauuguag cagaaaucau uuuauucguc augaucaaug    5580
aauaugugau uugcuccaga ucguuagaag gaaaaguaag auuucaguca ucaaaaaugu    5640
uuuuaccgua gcccucaucu aacuuacacg uggugcauau uaaaauaagc agagaaaaaa    5700
aaaugugaau aaacuacuga aaacacuugg uguuugugu caaugagac cuccugcaa      5760 ccugcuccc augguggca guuacaggc ccaucagaua uuguugaaag aaagcaauau       5820
auccaugaau gaaggcuaaa auugcaaucc uuuacccuuu gaggcauauu cagu ugaaa    5880 acaaaagaa aagaaaauuu ggcuagagg ucacagagc ucccauauga ccaagucuca       5940
agcacauuaa aucaugguug uuuacuggcc aagggcgucc acuagacaac ucuaucccuu    6000
gcgcugaagc ucaaucgugc ugagggagag cuuucuuaau auuacugugu ugcucuuagc    6060
ccuucucugg guuaggaucu gucagcauuu cuaugauaaa cuccuauucu caaagguuuu    6120
uaauuugacc auaaaaaugu gccccaggcu gaaguuugcu auacagggcu guaccaaaga    6180
gugaagguuu acuccuucu cuuccaacu ucuuccccau ucccaagga aaagaacaac       6240 aaaaaaaucu gguauggucc cuccuuaaua ugauuucag aauuuuggaa agcaccaaga     6300
uccaagaugg uaguuuuaau guaguuacuc auucgcacac auuuuuaaa uuuaaugggu     6360 caccuggcau auauuugaga uaacauaucu uuucuauaau uuguaagcua uaauuuuuu     6420 uaacugcuac augauauuu uuuuugccca agauuuuaa aagacuugaa guuggucagu      6480
ucaaaacuca gauuuuucua cacauugucu gccauguccca uuaggaguuu ggggaaaaua   6540
cucucacaca gacccuuacu uugcaugcag uuuagagggu aagaucgug cuucuuugg     6600 ggauaaagau uuccuacuu aauugucaaa uuucauggag ccauucuagu cuguggga       6660 aaauagugau uaaaagcacu uccaaaauua acauuuuug acaauucaga augaaaaga      6720 agcaggggaa aauaauacac uuacucuuu ucuugcuuaa aggcaaacaa aucaaugaaa     6780
cuugaggaca cacuaaacau uugauaacug caaaugugcu uuaaaauug guucaauggu    6840 gcuuacacau gaaacggaaa caaauggggu uccuaggacg ucagaaggaa ucuuuaguuu    6900
guauguaauu acacacuaga ggaggaggug cuuuuaagcc agucuuuau uuuuaaucau    6960 cucaaauaug caaccauaca ugcaguaaca uuaaggggucg uaaacuggug ggaaacagga   7020
acuucagugg agaggcuuaa augccucugg uuagaguggg gguuuugu uguuguuua       7080 uuguggguu caacacugc gcaucauuuc ugugaucaag uuucuaacug gcauguguuu      7140
ugaucaugag guuuaccaua ucuugcccau acagacaaau gagagaucua guucauuu      7200 guucccuaaa gaaagaacac ucucuaaaau uaaaucauac cuguaaauuu cuucagcauu    7260
uguuucuguu caaugaaauu gagacccuua auguugcuuu aauguaaaau ugaauauuuu    7320
gucugugaua acuuuaaua auuuaaagua agaauaguu cuaaagucuu cacguugcu       7380 acuaagagaa aauagaauuu uaaggugau gauaaagaug cuauaaugc aguucacucc      7440 aguccaauca aauguaguaa gaaaaaagucc uugaauaguu cucuagggac aauuucucac   7500
uugccauuga cauuaaucuu uggu guauuc ucagaaaaaa uaaaaagaaa uugaaacugg   7560
uccaagguua uagucauauc cucgauaacu uugaaaaaa aauuuuauua ggaaauuaau     7620
acuagccuuu uucauucugg cugaaagaaa auuauuaaag gauuaguuga gugugaaauu    7680
```

```
caacaguauu uugcucauac auacuaaaaa ggugcguagg gacuuggcgc auuuaaacaa      7740
guuucugaaa gguuucaauu ugacucaaga aaaaaauuca auauuucuuu ugaaaauacu      7800
gaauuuauca cuugcugcau ggaucagaug gcauagguua aucuuugauu uucagaaucc      7860
uaaugaaaua acuuucaaac aauuugguuc cuuaauuaaa ggugaauga gauccaauuu       7920 uuccccuaa uccuucaguu uaagcugaua caugagguu aauguggaau gaaaucaucu         7980
gugauauauu auguucauuu aucaacugag cuuuuugau guugccuguu uuuauguaaa        8040
acauguucuu aaaguuaaua aaauaauagu acuuggugua aa                         8082
```

<210> SEQ ID NO 2
<211> LENGTH: 729
<212> TYPE: PRT
<213> ORGANISM: Homo sapiens

<400> SEQUENCE: 2

```
Met Ser Phe Gly Arg Asp Met Glu Leu Glu His Phe Asp Glu Arg Asp
1               5                   10                  15

Lys Ala Gln Arg Tyr Ser Arg Gly Ser Arg Val Asn Gly Leu Pro Ser
                20                  25                  30

Pro Thr His Ser Ala His Cys Ser Phe Tyr Arg Thr Arg Thr Leu Gln
            35                  40                  45

Thr Leu Ser Ser Glu Lys Lys Ala Lys Lys Val Arg Phe Tyr Arg Asn
    50                  55                  60

Gly Asp Arg Tyr Phe Lys Gly Ile Val Tyr Ala Ile Ser Pro Asp Arg
65                  70                  75                  80

Phe Arg Ser Phe Glu Ala Leu Leu Ala Asp Leu Thr Arg Thr Leu Ser
                85                  90                  95

Asp Asn Val Asn Leu Pro Gln Gly Val Arg Thr Ile Tyr Thr Ile Asp
            100                 105                 110

Gly Leu Lys Lys Ile Ser Ser Leu Asp Gln Leu Val Glu Gly Glu Ser
        115                 120                 125

Tyr Val Cys Gly Ser Ile Glu Pro Phe Lys Lys Leu Glu Tyr Thr Lys
130                 135                 140

Asn Val Asn Pro Asn Trp Ser Val Asn Val Lys Thr Thr Ser Ala Ser
145                 150                 155                 160

Arg Ala Val Ser Ser Leu Ala Thr Ala Lys Gly Ser Pro Ser Glu Val
                165                 170                 175

Arg Glu Asn Lys Asp Phe Ile Arg Pro Lys Leu Val Thr Ile Ile Arg
            180                 185                 190

Ser Gly Val Lys Pro Arg Lys Ala Val Arg Ile Leu Leu Asn Lys Lys
        195                 200                 205

Thr Ala His Ser Phe Glu Gln Val Leu Thr Asp Ile Thr Asp Ala Ile
    210                 215                 220

Lys Leu Asp Ser Gly Val Val Lys Arg Leu Tyr Thr Leu Asp Gly Lys
225                 230                 235                 240

Gln Val Met Cys Leu Gln Asp Phe Phe Gly Asp Asp Ile Phe Ile
                245                 250                 255

Ala Cys Gly Pro Glu Lys Phe Arg Tyr Gln Asp Asp Phe Leu Leu Asp
            260                 265                 270

Glu Ser Glu Cys Arg Val Val Lys Ser Thr Ser Tyr Thr Lys Ile Ala
        275                 280                 285

Ser Ser Ser Arg Arg Ser Thr Thr Lys Ser Pro Gly Pro Ser Arg Arg
    290                 295                 300
```

```
Ser Lys Ser Pro Ala Ser Thr Ser Val Asn Gly Thr Pro Gly Ser
305                 310                 315                 320

Gln Leu Ser Thr Pro Arg Ser Gly Lys Ser Pro Ser Pro Ser Thr
            325                 330                 335

Ser Pro Gly Ser Leu Arg Lys Gln Arg Ser Ser Gln His Gly Gly Ser
                340                 345                 350

Ser Thr Ser Leu Ala Ser Thr Lys Val Cys Ser Ser Met Asp Glu Asn
            355                 360                 365

Asp Gly Pro Gly Glu Glu Val Ser Glu Gly Phe Gln Ile Pro Ala
370                 375                 380

Thr Ile Thr Glu Arg Tyr Lys Val Gly Arg Thr Ile Gly Asp Gly Asn
385                 390                 395                 400

Phe Ala Val Val Lys Glu Cys Val Glu Arg Ser Thr Ala Arg Glu Tyr
                405                 410                 415

Ala Leu Lys Ile Ile Lys Lys Ser Lys Cys Arg Gly Lys Glu His Met
                420                 425                 430

Ile Gln Asn Glu Val Ser Ile Leu Arg Arg Val Lys His Pro Asn Ile
            435                 440                 445

Val Leu Leu Ile Glu Glu Met Asp Val Pro Thr Glu Leu Tyr Leu Val
450                 455                 460

Met Glu Leu Val Lys Gly Gly Asp Leu Phe Asp Ala Ile Thr Ser Thr
465                 470                 475                 480

Asn Lys Tyr Thr Glu Arg Asp Ala Ser Gly Met Leu Tyr Asn Leu Ala
                485                 490                 495

Ser Ala Ile Lys Tyr Leu His Ser Leu Asn Ile Val His Arg Asp Ile
            500                 505                 510

Lys Pro Glu Asn Leu Leu Val Tyr Glu His Gln Asp Gly Ser Lys Ser
            515                 520                 525

Leu Lys Leu Gly Asp Phe Gly Leu Ala Thr Ile Val Asp Gly Pro Leu
530                 535                 540

Tyr Thr Val Cys Gly Thr Pro Thr Tyr Val Ala Pro Glu Ile Ile Ala
545                 550                 555                 560

Glu Thr Gly Tyr Gly Leu Lys Val Asp Ile Trp Ala Ala Gly Val Ile
                565                 570                 575

Thr Tyr Ile Leu Leu Cys Gly Phe Pro Pro Phe Arg Gly Ser Gly Asp
            580                 585                 590

Asp Gln Glu Val Leu Phe Asp Gln Ile Leu Met Gly Gln Val Asp Phe
            595                 600                 605

Pro Ser Pro Tyr Trp Asp Asn Val Ser Asp Ser Ala Lys Glu Leu Ile
610                 615                 620

Thr Met Met Leu Leu Val Asp Val Asp Gln Arg Phe Ser Ala Val Gln
625                 630                 635                 640

Val Leu Glu His Pro Trp Val Asn Asp Asp Gly Leu Pro Glu Asn Glu
                645                 650                 655

His Gln Leu Ser Val Ala Gly Lys Ile Lys Lys His Phe Asn Thr Gly
            660                 665                 670

Pro Lys Pro Asn Ser Thr Ala Ala Gly Val Ser Val Ile Ala Leu Asp
            675                 680                 685

His Gly Phe Thr Ile Lys Arg Ser Gly Ser Leu Asp Tyr Tyr Gln Gln
            690                 695                 700

Pro Gly Met Tyr Trp Ile Arg Pro Pro Leu Leu Ile Arg Arg Gly Arg
705                 710                 715                 720

Phe Ser Asp Glu Asp Ala Thr Arg Met
```

-continued

```
                725
```

<210> SEQ ID NO 3
<211> LENGTH: 19
<212> TYPE: RNA
<213> ORGANISM: Homo sapiens

<400> SEQUENCE: 3
gggagugaga acaaucuac                                              19

<210> SEQ ID NO 4
<211> LENGTH: 21
<212> TYPE: DNA
<213> ORGANISM: Homo sapiens

<400> SEQUENCE: 4
ggtgatccac atctgctgga a                                           21

<210> SEQ ID NO 5
<211> LENGTH: 20
<212> TYPE: DNA
<213> ORGANISM: Homo sapiens

<400> SEQUENCE: 5
atcattgctc ctcctcaggg                                             20

<210> SEQ ID NO 6
<211> LENGTH: 22
<212> TYPE: DNA
<213> ORGANISM: Homo sapiens

<400> SEQUENCE: 6
agtcttccga ttccgagttg ag                                          22

<210> SEQ ID NO 7
<211> LENGTH: 22
<212> TYPE: DNA
<213> ORGANISM: Homo sapiens

<400> SEQUENCE: 7
cagcaaccag gaatgtattg ga                                          22

<210> SEQ ID NO 8
<211> LENGTH: 22
<212> TYPE: DNA
<213> ORGANISM: Homo sapiens

<400> SEQUENCE: 8
cacacatcag cacaactacg ca                                          22

<210> SEQ ID NO 9
<211> LENGTH: 19
<212> TYPE: DNA
<213> ORGANISM: Homo sapiens

<400> SEQUENCE: 9
ttgaccctct tggcagcag                                              19

<210> SEQ ID NO 10
<211> LENGTH: 20
<212> TYPE: DNA
<213> ORGANISM: Mus musculus

<400> SEQUENCE: 10

```
cagcctggac gagctggtgg                                               20

<210> SEQ ID NO 11
<211> LENGTH: 20
<212> TYPE: DNA
<213> ORGANISM: Mus musculus

<400> SEQUENCE: 11
tgaccagttg gggttcacat                                               20

<210> SEQ ID NO 12
<211> LENGTH: 17
<212> TYPE: DNA
<213> ORGANISM: Homo sapiens

<400> SEQUENCE: 12
ctcgcttcgg cagcaca                                                  17

<210> SEQ ID NO 13
<211> LENGTH: 20
<212> TYPE: DNA
<213> ORGANISM: Homo sapiens

<400> SEQUENCE: 13
aacgcttcac gaatttgcgt                                               20

<210> SEQ ID NO 14
<211> LENGTH: 26
<212> TYPE: DNA
<213> ORGANISM: Homo sapiens

<400> SEQUENCE: 14
gaggtagtag gttgtatagt ttagaa                                        26

<210> SEQ ID NO 15
<211> LENGTH: 19
<212> TYPE: DNA
<213> ORGANISM: Homo sapiens

<400> SEQUENCE: 15
aaagctagga ggctgtaca                                                19

<210> SEQ ID NO 16
<211> LENGTH: 81
<212> TYPE: PRT
<213> ORGANISM: Homo sapiens

<400> SEQUENCE: 16
```

Asp Asp Gly Leu Pro Glu Asn Glu His Gln Leu Ser Val Ala Gly Lys
1               5                   10                  15

Ile Lys Lys His Phe Asn Thr Gly Pro Lys Pro Asn Ser Thr Ala Ala
            20                  25                  30

Gly Val Ser Val Ile Ala Leu Asp His Gly Phe Thr Ile Lys Arg Ser
        35                  40                  45

Gly Ser Leu Asp Tyr Tyr Gln Gln Pro Gly Met Tyr Trp Ile Arg Pro
    50                  55                  60

Pro Leu Leu Ile Arg Arg Gly Arg Phe Ser Asp Glu Asp Ala Thr Arg
65                  70                  75                  80

Met

<210> SEQ ID NO 17
<211> LENGTH: 92
<212> TYPE: PRT
<213> ORGANISM: Homo sapiens

<400> SEQUENCE: 17

Asp Asp Gly Leu Pro Glu Asn Glu His Gln Leu Ser Val Ala Gly Lys
1               5                   10                  15

Ile Lys Lys His Phe Asn Thr Gly Pro Lys Pro Asn Ser Thr Ala Ala
            20                  25                  30

Gly Val Ser Val Ile Ala Thr Thr Ala Leu Asp Lys Glu Arg Gln Val
        35                  40                  45

Phe Arg Arg Arg Arg Asn Gln Asp Val Arg Ser Arg Tyr Lys Ala Gln
    50                  55                  60

Pro Ala Pro Pro Glu Leu Asn Ser Glu Ser Glu Asp Tyr Ser Pro Ser
65                  70                  75                  80

Ser Ser Glu Thr Val Arg Ser Pro Asn Ser Pro Phe
                85                  90

<210> SEQ ID NO 18
<211> LENGTH: 81
<212> TYPE: PRT
<213> ORGANISM: Homo sapiens

<400> SEQUENCE: 18

Asp Asp Gly Leu Pro Glu Asn Glu His Gln Leu Ser Val Ala Gly Lys
1               5                   10                  15

Ile Lys Lys His Phe Asn Thr Gly Pro Lys Pro Asn Ser Thr Ala Ala
            20                  25                  30

Gly Val Ser Val Ile Ala Leu Asp His Gly Phe Thr Ile Lys Arg Ser
        35                  40                  45

Gly Ser Leu Asp Tyr Tyr Gln Gln Pro Gly Met Tyr Trp Ile Arg Pro
    50                  55                  60

Pro Leu Leu Ile Arg Arg Gly Arg Phe Ser Asp Glu Asp Ala Thr Arg
65                  70                  75                  80

Met

<210> SEQ ID NO 19
<211> LENGTH: 71
<212> TYPE: PRT
<213> ORGANISM: Homo sapiens

<400> SEQUENCE: 19

Asp Asp Gly Leu Pro Glu Asn Glu His Gln Leu Ser Val Ala Gly Lys
1               5                   10                  15

Ile Lys Lys His Phe Asn Thr Gly Pro Lys Pro Asn Ser Thr Ala Ala
            20                  25                  30

Gly Val Ser Val Ile Ala Thr Thr Ala Leu Asp Lys Glu Arg Gln Val
        35                  40                  45

Phe Arg Arg Arg Arg Asn Gln Asp Val Arg Ser Arg Tyr Lys Ala Gln
    50                  55                  60

Pro Ala Pro Pro Glu Leu Asn
65                  70

<210> SEQ ID NO 20
<211> LENGTH: 30
<212> TYPE: PRT
<213> ORGANISM: Homo sapiens

```
<400> SEQUENCE: 20

Asp Tyr Tyr Gln Gln Pro Gly Met Tyr Trp Ile Arg Pro Pro Leu Leu
1               5                   10                  15

Ile Arg Arg Gly Arg Phe Ser Asp Glu Asp Ala Thr Arg Met
                20                  25                  30

<210> SEQ ID NO 21
<211> LENGTH: 30
<212> TYPE: PRT
<213> ORGANISM: Homo sapiens

<400> SEQUENCE: 21

Ala Gly Val Ser Val Ile Ala Leu Asp His Gly Phe Thr Ile Lys Arg
1               5                   10                  15

Ser Gly Ser Leu Asp Tyr Tyr Gln Gln Pro Gly Met Tyr Trp
                20                  25                  30

<210> SEQ ID NO 22
<211> LENGTH: 174
<212> TYPE: DNA
<213> ORGANISM: Artificial sequence
<220> FEATURE:
<223> OTHER INFORMATION: pLet7a-Luc Reporter Vector (Product No.
      LR-0037; Signosis, Inc., Santa Clara, CA)
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (84)..(85)
<223> OTHER INFORMATION: n is a, c, g, or t
<220> FEATURE:
<221> NAME/KEY: misc_feature
<222> LOCATION: (108)..(109)
<223> OTHER INFORMATION: n is a, c, g, or t

<400> SEQUENCE: 22
agaaaaatca gagagatcct cataannagg ccaagaaggg cggaaagtcc aaattgctcg      60
agtgatgaaa gctgcgcact agtnnaacta tacaacctac tacctcanna agcttaataa     120
aggatctttt attttcattg gatctgtgtg ttggtttttt gtatgcggcc gcta           174
```